US009357941B2

(12) United States Patent
Simon

(10) Patent No.: US 9,357,941 B2
(45) Date of Patent: Jun. 7, 2016

(54) BRAIN-COMPUTER INTERFACE TEST BATTERY FOR THE PHYSIOLOGICAL ASSESSMENT OF NERVOUS SYSTEM HEALTH

(75) Inventor: Adam Jay Simon, Yardley, PA (US)

(73) Assignee: Cerora, Inc., Bethlehem, PA (US)

(*) Notice: Subject to any disclaimer, the term of this patent is extended or adjusted under 35 U.S.C. 154(b) by 0 days.

(21) Appl. No.: 13/327,034

(22) Filed: Dec. 15, 2011

(65) Prior Publication Data

US 2012/0150545 A1    Jun. 14, 2012

Related U.S. Application Data

(62) Division of application No. PCT/US2010/038560, filed on Jun. 14, 2010.

(60) Provisional application No. 61/186,901, filed on Jun. 15, 2009, provisional application No. 61/291,830, filed on Dec. 31, 2009.

(51) Int. Cl.
*A61B 5/00* (2006.01)
*A61B 5/0476* (2006.01)
(Continued)

(52) U.S. Cl.
CPC ............ *A61B 5/0476* (2013.01); *A61B 5/0484* (2013.01); *A61B 5/162* (2013.01); *A61B 5/6804* (2013.01); *A61B 5/6814* (2013.01); *A61B 5/4011* (2013.01); *A61B 5/4023* (2013.01); *A61B 5/411* (2013.01); *A61B 5/726* (2013.01); *A61B 5/7257* (2013.01)

(58) Field of Classification Search
CPC .. A61B 5/162; A61B 5/4088; A63B 69/0053; A63F 9/0096

USPC .......................................... 600/544; 704/270
See application file for complete search history.

(56) References Cited

U.S. PATENT DOCUMENTS

2004/0152995 A1* 8/2004 Cox et al. ...................... 600/544
2005/0172021 A1* 8/2005 Brown .......................... 709/224

FOREIGN PATENT DOCUMENTS

WO    WO 2010/147913 A1    12/2010

OTHER PUBLICATIONS

Schachinger, et al. "Cognitive and psychomotor function in hypoglycemia: response error patterns and retest reliability". Pharmacology, Biochemistry and Behavior 75 (2003) 915-920.*

(Continued)

*Primary Examiner* — Christian Jang
(74) *Attorney, Agent, or Firm* — Baker & Hostetler LLP

(57) ABSTRACT

A battery of three or more sensory and cognitive challenge tasks actively or dynamically challenge the brain to monitor its state for assessment of injury, disease, or compound effect, among others. The system analyzes and assesses a personalized biometric brain health signature by integrating the use of electroencephalography (EEG), somato-sensory, neuropsychological, and/or cognitive stimulation, and novel signal processing and display. The system also provides for early detection of dementia, including Alzheimer's disease (AD), vascular dementia (VAD), mixed dementia (AD and VAD), MCI, and other dementia-type disorders, as well as brain injury states such as mild Traumatic Brain Injury and can provide some or all of the following improvements over conventional systems and methods, including: (1) Increased sensitivity, specificity, and overall accuracy; (2) early detection of disease and injury; and (3) enhanced portability with remote data acquisition capability.

11 Claims, 33 Drawing Sheets

(51) Int. Cl.
*A61B 5/16* (2006.01)
*A61B 5/0484* (2006.01)

(56) References Cited

OTHER PUBLICATIONS

Tombaugh, Tom N. "A comprehensive review of the Paced Auditory Serial Addition Test (PASAT)". Archives of Clinical Neuropsychology 21 (2006) 53-76.*
Bishop, "Neurocognitive Mechanisms of Anxiety: An Integrative Account", Trends Cogn. Sci., Jul. 2007, 11(7), 307-316.
Burykh, "Interaction of Hypocapnia, Hypoxia, Brain Blood Flow and Brain Electrical Activity in Voluntary Hyperventilation in Humans", Neurosci. Behav. Physiol., Sep. 2008, 38(7), 647-659.
Cai et al., "A Model for Binaural Response Properties of Inferior-Colliculus Neurons, A Model with Interaural Time Difference-Sensitive Excitatory and Inhibitory Inputs", J. Acoust. Soc. Am., Jan. 1998, 103(1), 475-493.
Craig et al., "Functional Imaging of an Illusion of Pain", Nature, Nov. 1996, 384(6606), 258-260.
Craig et al., "The Thermal Grill Illusion: Unmasking the Burn of Cold Pain", Science, Jul. 1994, 265(5169), 252-255.
Croy et al., "PTSD, But Not Childhood Maltreatment, Modifies Responses to Unpleasant Odors", Int. J. Psychophysoil, Mar. 2010, 75(3), 326-331.
Dmitrieva et al., "The EEG Correlates of Delayed Mental Development in Adolescents", Database Medline US National Library of Medicine, 2005, Database Accession No. NLM16252384.
EEGLab, www.sccn.ucsd.edu/eeglab, accessed Jul. 30, 2012, 6 pages.
Fink, "Remembering the Lost Neuroscience of Pharmaco-EEG", Acta Psychiatr. Scand., Mar. 2010, 121(3), 161-173.
Gevins et al., "Tracking the Cognitive Pharmacodynamics of Psychoactive Substances with Combinations of Behavioral and Neurophysiological Measures", Neuropsychopharmacology, Official Publication of the American College of Neuropsychopharmacology, Jan. 2002, 26(1), 27-39.
Hardware by Compumedics Neuroscan, www.com.Qumedics.com, accessed Jul. 30, 2012, 2 pages.
Keck et al., "Challenge Studies in Anxiety Disorders", Handbook Exp. Pharmacal, 2005, 169, 449-468.
Monkul et al., "History of Suffocation, State-Trait Anxiety and Anxiety Sensitivity in Predicting 35% Carbon Dioxide-Induced Panic", Psychiatry Res., Sep. 2010, 179(2), 194-197.
Lopes et al., "Carbon Dioxide-Induced Panic Attacks and Quantitative Electroencephalogram in Panic Disorder Patients", World J. Bio. Psychiatry, Mar. 2010, 11(2 Pt 2), 357-363.
Oster, "Auditory Beats in the Brain", Scientific American, Oct. 1973, 229, 94-102.
Paiva et al., "New Vistas for Alpha-Frequency Band Oscillations", Trends Neurosci., Apr. 2007, 30(4), 150-158.
Shinichi et al., "Multi-Aspect ERP Data Analysis for Understanding Human Calculation Related Information Processing Mechanism", Web Intelligence and International Agent Technology Workshops, 2006/IEEE/WIC/ACM International Conference on IEEE, PI, Dec. 1, 2006, 481-485.
Single Electrode EEG Headsets, such as the MindSet Pro by NeuroSky, www.neurosky.com, accessed Jul. 30, 2012, 4 pages.
Tombaugh, "A Comprehensive Review of the Paced Auditory Serial Addition Test (PASAT)", Arch. Clin. Neuropsychol, Jan. 2006, 21(1), 53-76.
VIASYS Healthcare's Nicolet, www.viasyshealthcare.com, accessed Jul. 30, 2012, 1 page This webpage comes up as www.carefusion.com.
Voipio et al., "Millivolt-scale DC Shifts in the Human Scalp EEG: Evidence for a Nonneuronal Generator", J. Neurophysiol, 2003, 89(4), 2208-2214, First published Dec. 11, 2002.

* cited by examiner

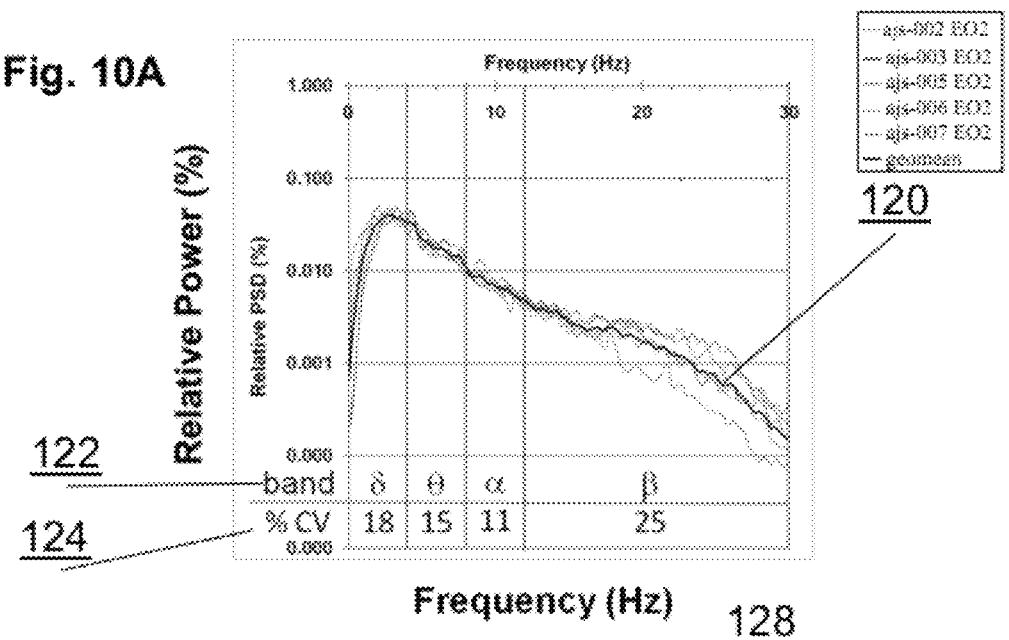
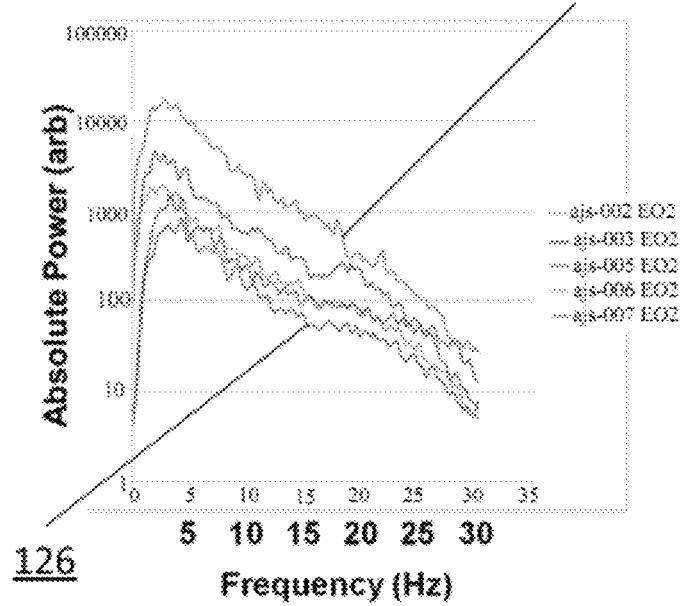

Fig. 12A 44 year old male
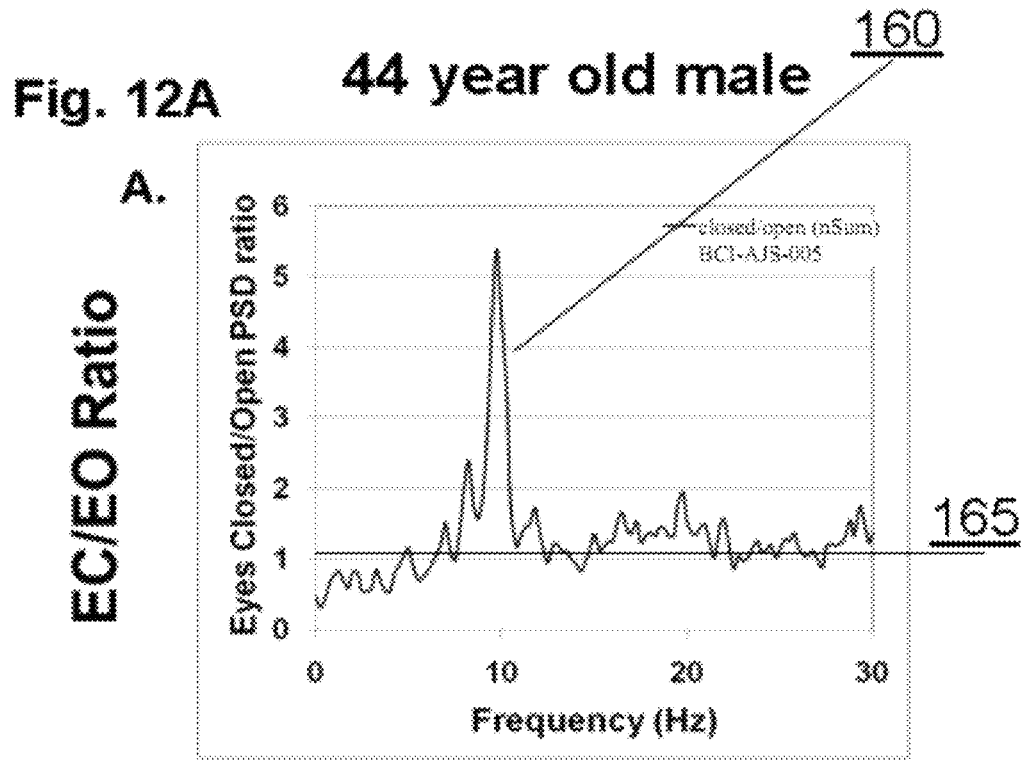
Fig. 12B 48 year old male
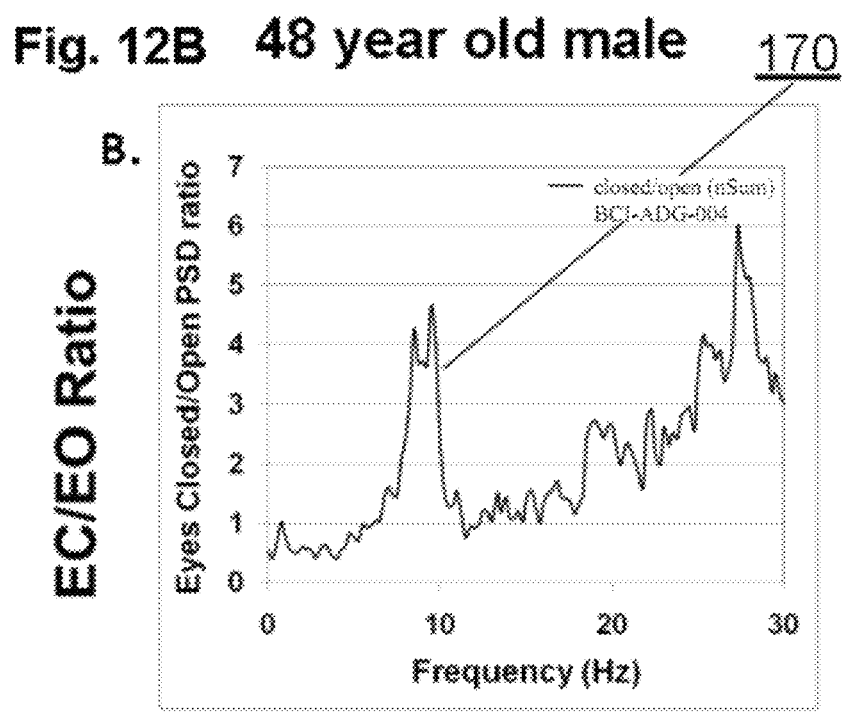

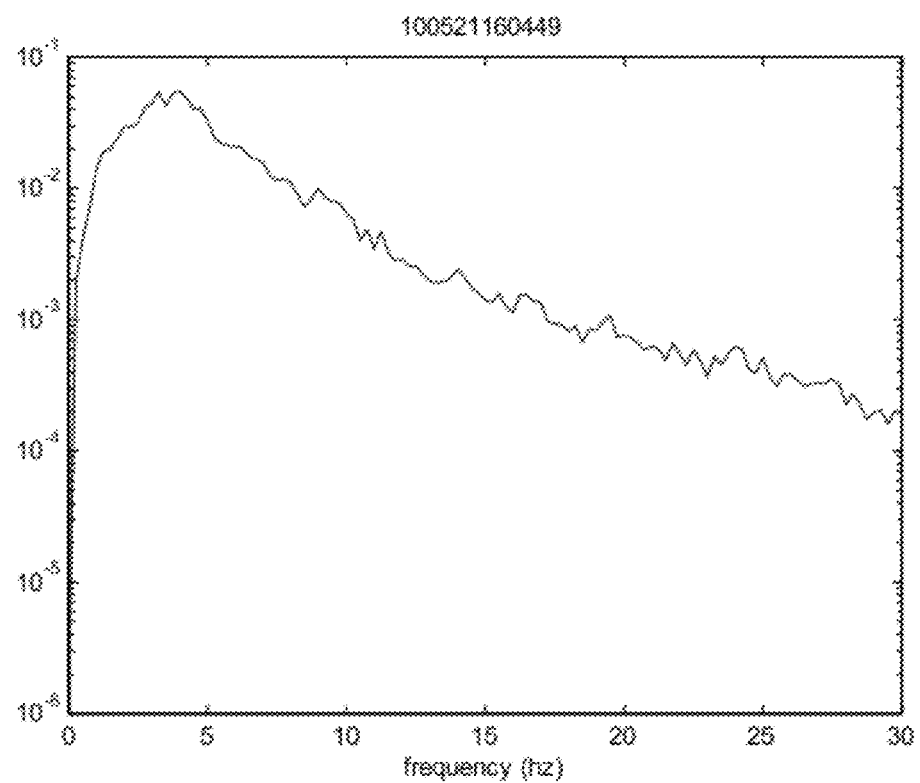
Fig. 18   CogScope™ EEG

Fig. 19 CogState™ Attention task data

365　　　　　366　367　　　　　　　368

Fig. 20 Synchronized CogState & fEEG data

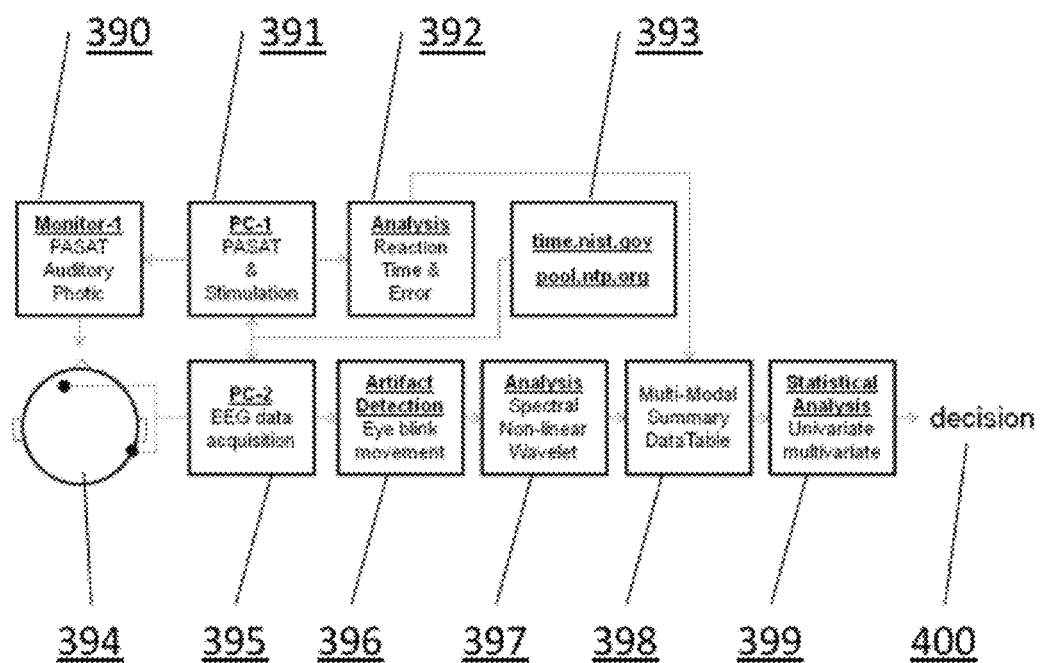
Fig. 21 PasatScope™ setup

Fig. 22   PASAT EEG data vs Resting EO
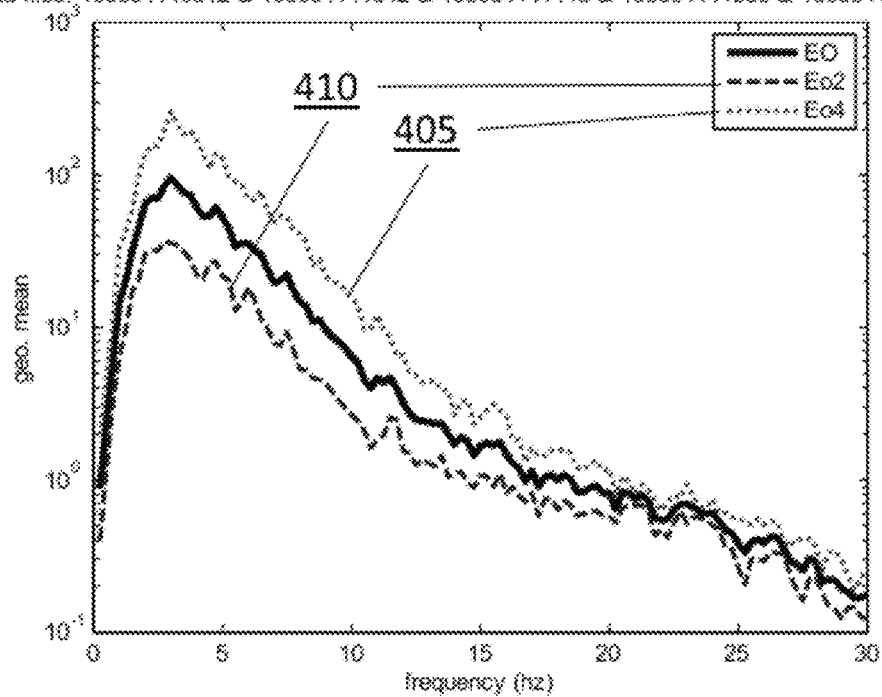

Fig. 23 Standard PASAT scoring
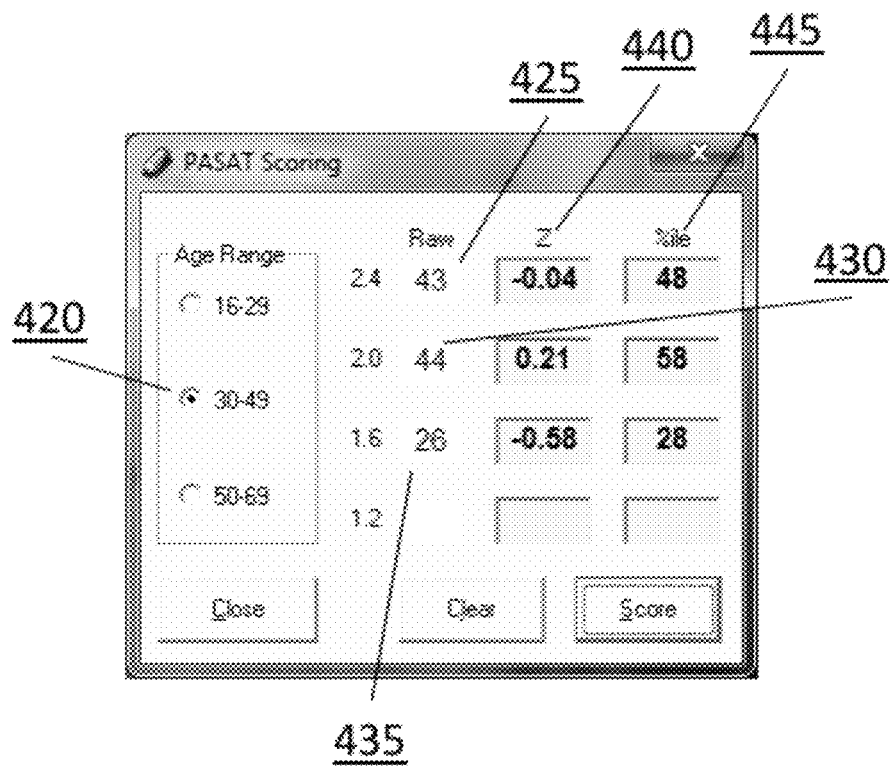

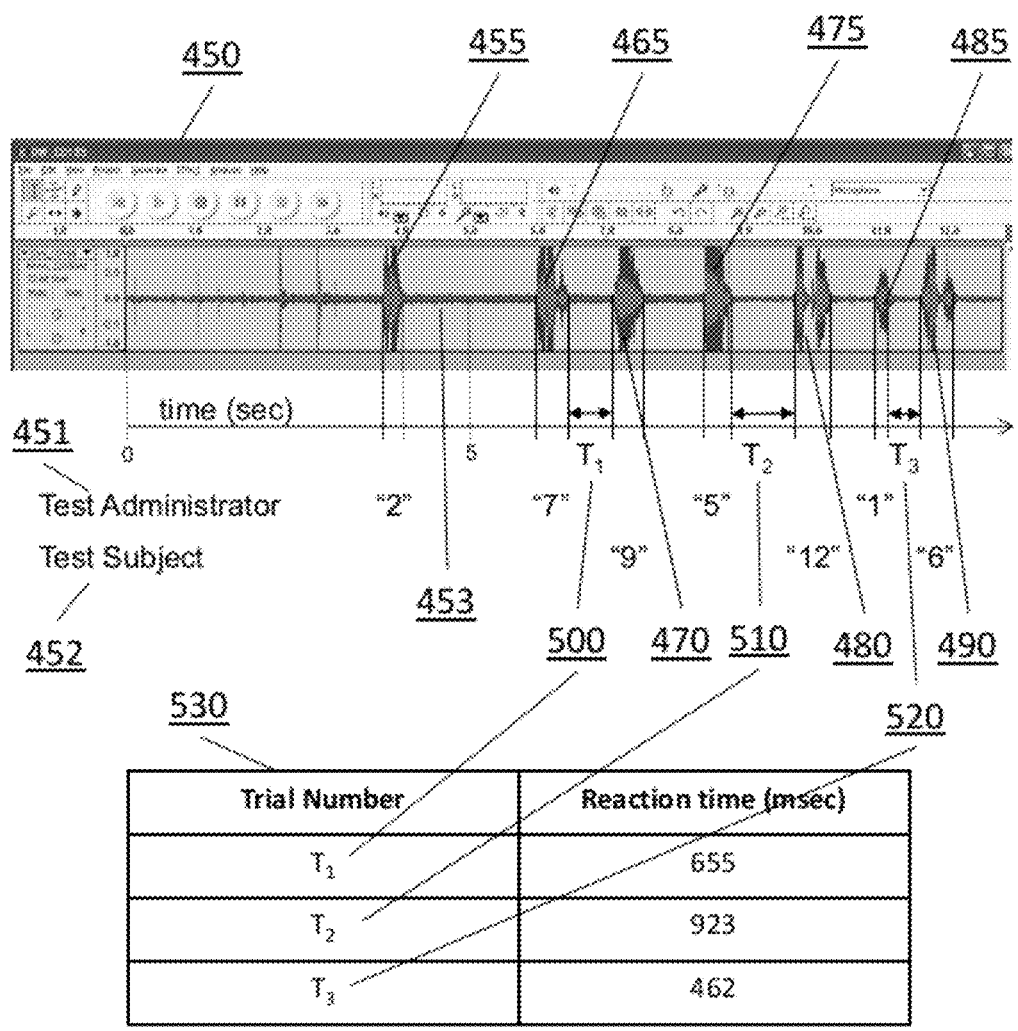

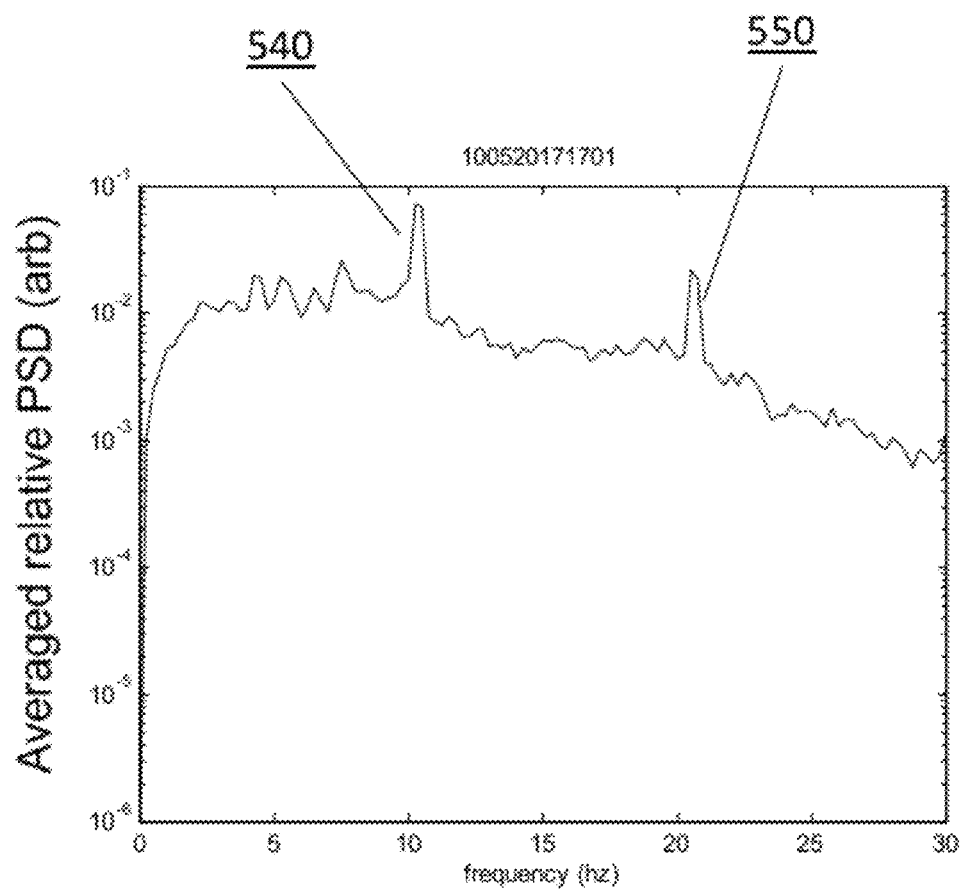
Fig. 25  Photic Stim at 10 Hz

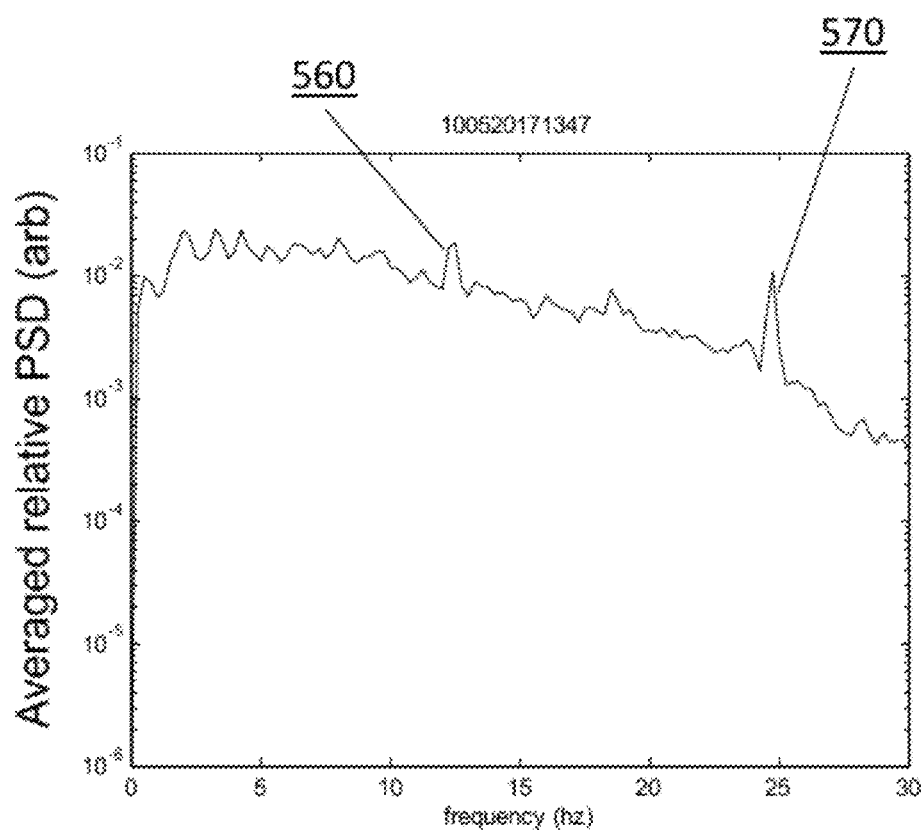
Fig. 26 Photic Stim at 12 Hz

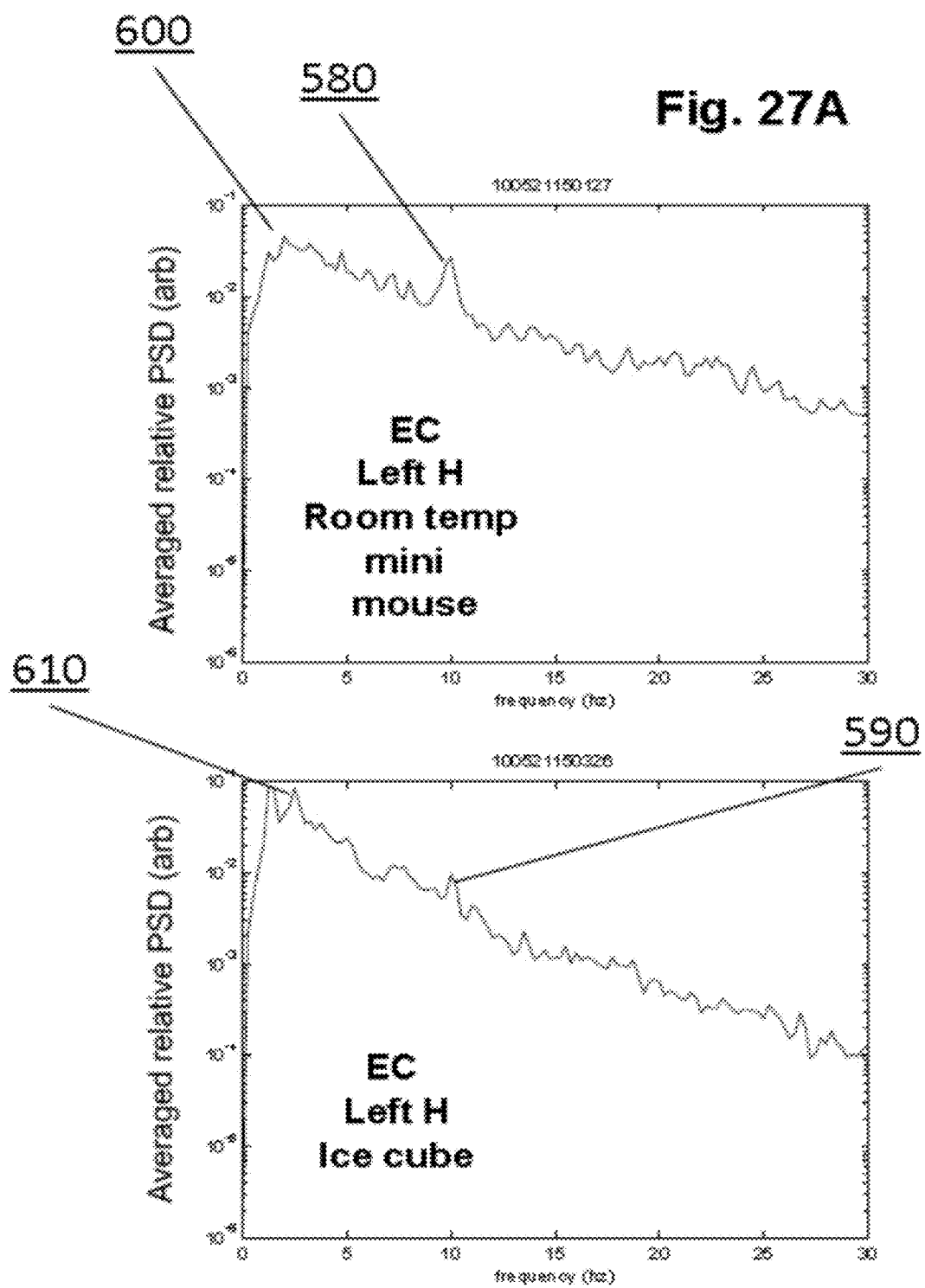

Fig. 29A    EO pre KLON pill
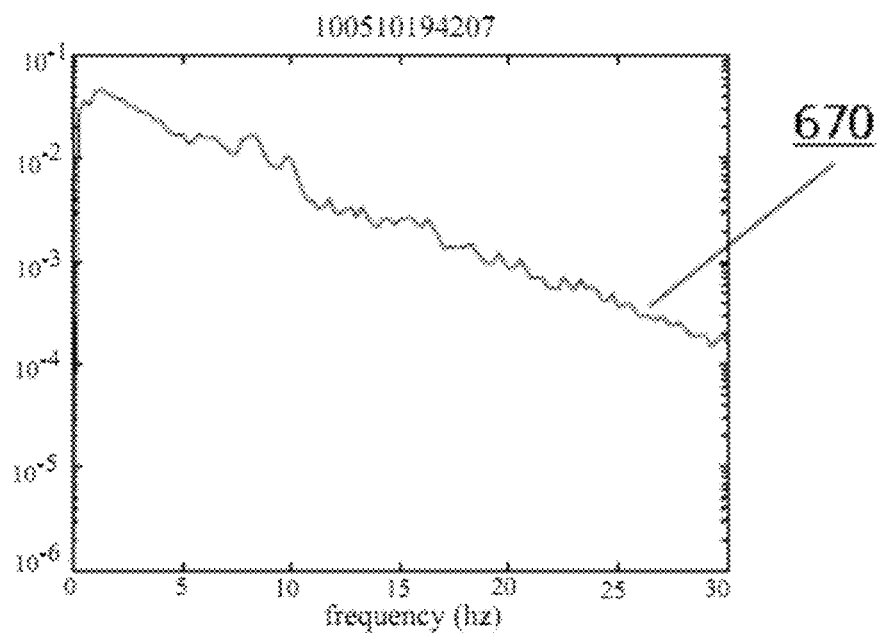
Fig. 29B    EO 80min post KLON pill
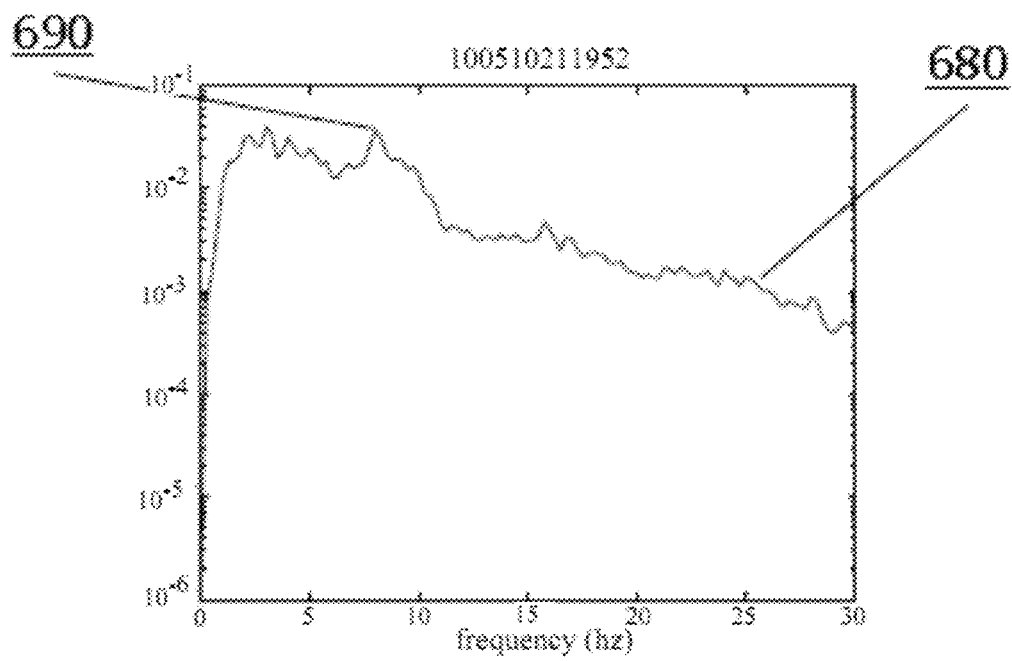

BRAIN-COMPUTER INTERFACE TEST BATTERY FOR THE PHYSIOLOGICAL ASSESSMENT OF NERVOUS SYSTEM HEALTH

CROSS REFERENCE TO RELATED APPLICATION

This application is a Divisional of PCT/US2010/038560 filed Jun. 14, 2010, which claims benefit of U.S. Provisional Application No. 61/186,901 filed Jun. 15, 2009 and U.S. Provisional Application No. 61/291,830 filed Dec. 31, 2009. The contents of these applications are hereby incorporated by reference in their entireties.

TECHNICAL FIELD

The invention relates to diagnosis and analysis of brain health through the creation of a personalized biometric brain health signature.

BACKGROUND

Normal functioning of the brain and nervous system is critical to a healthy, enjoyable and productive life. Disorders of the brain and nervous system are among the most dreaded of diseases. Many neurological disorders such as stroke, Alzheimer's dementia, and Parkinson's disease are insidious and progressive, becoming more common with increasing age. Others such as schizophrenia, depression, multiple sclerosis and epilepsy arise at younger age and can persist and progress throughout an individual's lifetime. Sudden catastrophic injuries to the nervous system, such as trauma, infections, and intoxications can also affect any individual of any age at any time.

Most nervous system dysfunction arises from complex interactions between an individual's genotype, environment and personal habits and thus often presents in highly personalized ways. However, despite the emerging importance of preventative health care, convenient means for objectively assessing the health of one's own nervous system have not been widely available. Therefore, new ways to monitor the personalized health status of the brain and nervous system are needed for normal health surveillance, early diagnosis of dysfunction, tracking of disease progression and the discovery and optimization of treatments and new therapies.

Unlike cardiovascular and metabolic disorders, where personalized health monitoring biomarkers such as blood pressure, cholesterol, and blood glucose have long become household terms, no such convenient biomarkers of brain and nervous system health exist. Quantitative neurophysiological assessment approaches such as positron emission tomography (PET), functional magnetic resonance imaging (fMRI) and neuropsychiatric or cognition testing involve significant operator expertise, inpatient or clinic based testing and significant time and expense. One potential technique that may be adapted to serve a broader role as a facile biomarker of nervous system function is electroencephalography (EEG), which measures the brain's ability to generate and transmit electrical signals. However, formal lab based EEG approaches typically require significant operator training, cumbersome equipment, and are used primarily to test for epilepsy.

Alternate and innovative biomarker approaches are needed to provide quantitative measurements of personal brain health that could greatly improve the prevention, diagnosis and treatment of neurological and psychiatric disorders.

SUMMARY

According to one aspect of the invention, the systems and methods relate to assessing the brain health of a subject by applying at least one portable EEG electrode to the scalp; recording EEG signals in various brain states such as: resting states, while experiencing various standardized sensory inputs, while completing cognitive tasks, and while undergoing various other challenges, like a respiratory $CO_2$ challenge; transferring the data directly to an electronic device, such as a cell phone, a PDA or a computer; and processing the signal to create a personalized physiological brain health biometric signature to, for a non-limiting example, monitor disease progression, optimize treatment and therapy, and/or to provide biofeedback therapy. Moreover, the invention pertains to devices that include both stimulation and recording means within the same headset, including recording sensors and electronics as well as auditory, photic, and other sensory stimulation capability.

According to another aspect of the invention, a method is provided to monitor the brain and nervous system of a subject comprising applying at least one EEG electrode to the scalp of the subject; recording EEG signal data generated by the subject while in at least three of the following states, resting state, sensory and cognitive challenge state(s); transferring the EEG signal data to a microprocessor; and processing the EEG signal data to create a personalized biometric brain health signature.

According to another aspect of the invention, a method is provided to monitor the brain and nervous system of a subject comprising, applying at least one EEG electrode to the scalp of the subject; recording EEG signal data generated by the subject while the subject is in a resting state; displaying both neutral and traumatic images to the subject; recording EEG signal data generated by the subject during the displaying of both neutral and traumatic images; transferring the EEG signal data to a microprocessor; and processing the EEG signal data to create a personalized biometric brain health signature.

According to another aspect, the invention includes an alpha rhythm monitor process comprising of applying at least one EEG electrode to the scalp of the subject; recording EEG signal data including the alpha rhythm in a resting, eyes-closed state; perturbing the subject with a stimulus; recording EEG signal data, including alpha rhythm, generated by the subject during the perturbing; and comparing the alpha rhythm in the resting, eyes-closed state to the alpha rhythm generated by the subject during the perturbing to assess the integrity of the neural circuits conveying the perturbing stimulus.

According to another aspect, the invention includes a stimulus force F monitor process comprising applying at least one EEG electrode to a scalp of the subject; perturbing the subject with a first stimulus having a frequency F; recording EEG signal data generated by the subject during the perturbing with the first stimulus; perturbing the subject with a second stimulus; recording EEG signal data generated by the subject during the perturbing with the second stimulus; and comparing the EEG signal data corresponding to the first stimulus to the EEG signal data corresponding to the second stimulus to probe the integrity of the neural circuits conveying the first and second stimulus information.

According to another aspect, the invention includes a method of determining an effect of a medical therapy on a subject, comprising: applying at least one EEG electrode to the scalp of the subject; recording EEG data generated by the subject while exposed to a test battery of more than three sensory and cognitive challenge tasks at a time T1 prior to the administration of the therapy; administering the therapy to the subject; recording EEG data generated by the subject while exposed to the test battery at a time T2 after the administrating of the therapy; and comparing the EEG data recorded at time T1 to the EEG data recorded at time T2.

According to another aspect, the invention further includes a method to monitor the brain and nervous system of a subject comprising: applying at least one EEG electrode to the scalp of the subject; recording EEG signal data while the subject is performing a cognitive task; recording data pertaining to the performance of the cognitive task by the subject; transferring the EEG signal data and the cognitive performance data to a microprocessor; and processing the EEG signal data, including reaction time and accuracy data, and the cognitive performance data to create a multimodal, multi-variate personalized biometric brain health signature.

According to another aspect, the invention comprises an apparatus for determining a biometric signature of a brain or nervous system of a subject comprising: at least one EEG sensor; at least one reference sensor; a first electronics system coupled to record EEG sensor signal data from the at least one EEG sensor; a second electronics system adapted to present and coordinate sensory and cognitive stimuli to the subject simultaneously with the recording of the EEG signal data; and a third electronics system coupled to receive and process the EEG signal data and performance data of the subject corresponding to the sensory and cognitive stimuli to create a biometric brain health signature for the subject.

According to another aspect, the invention also comprises means to measure quantitatively an alpha rhythm of the brain and nervous system of the subject; means to perturb the subject with sensory and cognitive challenges; and means to measure quantitatively an effect on the subject's alpha rhythm due to the perturbation.

According to another aspect, the invention includes means to measure a baseline resting state EEG power spectral density of the subject; means to perturb the brain and nervous system of the subject with at least one of sensory and cognitive challenge perturbation, the perturbation having a frequency F; means to measure the response of at least one of the subject's brain and nervous system to the perturbation at each of Frequency F, a sub-harmonic of Frequency F and a super-harmonic of Frequency F; and means to compare the responses at F, the sub-harmonic of F, and the super-harmonic of F to each other.

According to another aspect, the invention includes at least one EEG sensor; at least one reference sensor; a first electronics system coupled to record EEG sensor signals from the EEG sensor; a second electronics system adapted to present and record data pertaining to the performance of cognitive tasks by the subject; and a third electronics system adapted to combine the data pertaining to the performance of the cognitive tasks by the subject and the EEG data to create multi-modal biometric classifiers.

Finally, according to another aspect, the invention includes a headset device for delivering both stimulation and challenge while recording EEG comprising: at least one EEG sensor; at least one reference sensor; a first electronics system coupled to record EEG sensor signals from the EEG sensor; and a second electronics system adapted to present and coordinate sensory and cognitive stimuli simultaneous with the recording of the EEG signal data.

BRIEF DESCRIPTION OF THE DRAWINGS

Embodiments of the invention can be better understood with reference to the following drawings.

FIG. 10A is a graph showing interday variability over five days of relative PSD traces, with an inset indicating the coefficients of variation in several spectral sub-bands.

FIG. 10B is a graph showing interday variability over five days of absolute PSD traces.

FIG. 12A is a graph showing a bin-wise ratio of an Eyes Closed (EC) divided by Eyes Open (EO) PSD in a volunteer.

FIG. 12B is a graph showing a bin-wise ratio of an Eyes Closed (EC) divided by Eyes Open (EO) PSD in a volunteer.

FIG. 18 is a graph showing a time averaged relative PSD recorded while a subject performed the computerized cognition Cog State™ Identification task ("Is it Red?") in the Cog State™ Research test battery.

FIG. 19 is a data table showing the raw data from the computerized cognition test including the reaction time of a subject performing the Cog State™ Identification task of the Cog State™ research battery.

FIG. 20 is a summary data table from the simultaneous recording of cognition data from the Cog State™ Identification task including reaction time and accuracy and functional EEG including spectral sub-band, non-linear dynamical, and wavelet biometrics.

FIG. 21 is a block diagram illustrating a system capable of simultaneous PASAT™ cognitive testing and auditory/visual stimulation with functional EEG data stream recording on two synchronized computers.

FIG. 22 is a graph showing the time averaged relative PSD from a 105 second EEG recording collected during the PASAT™ test at speed 2.4.

FIG. 23 is a screenshot of the PASAT™ scoring function in the University of Victoria Neuropsychology Department's computerized PASAT™ software.

FIG. 24 is a screenshot of a time series of the recorded audio file of both the administrator and test subject's responses during the PASAT™ test, with reaction time data indicated and extracted in the table below.

FIG. 25 is a graph showing calculated time averaged relative PSD of a subject undergoing photic stimulation with LED goggles at 10 Hz in an Eyes Closed state, showing both the primary driving frequency F as well as the harmonic at 2F.

FIG. 26 is a graph showing calculated time averaged relative PSD of a subject undergoing photic stimulation with LED goggles at 12 Hz in an Eyes Closed state, showing both the primary driving frequency F as well as the harmonic at 2F.

FIG. 27A is a graph showing the calculated time averaged relative PSD for a subject holding a room temperature computer mouse as a sensory challenge control.

FIG. 27B is a graph showing the calculated time averaged relative PSD for a subject holding an ice cube for 60 seconds as a sensory challenge assessing pain circuits, much like the thermal grill.

FIG. 29A is a graph of an Eyes Open resting state shortly before a 0.5 mg dose of GA8A_A receptor agonist clonazepam was taken.

FIG. 29B is a graph of an Eyes Open resting state 80 minutes after a 0.5 mg dose of GA8A_A receptor agonist clonazepam was taken, showing elevated spectral beta in the post dose PSD.

DETAILED DESCRIPTION OF ILLUSTRATIVE EMBODIMENTS

Definitions

Figure 1:
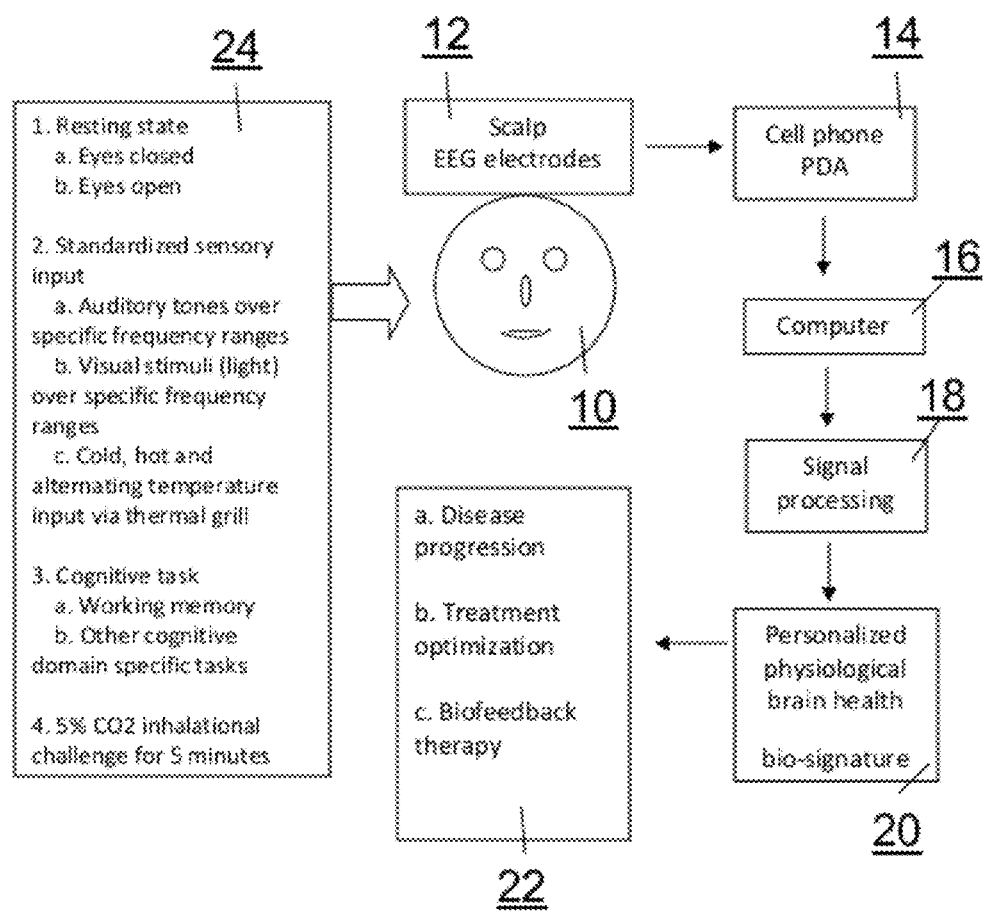
FIG. 1 is a schematic diagram illustrating the three fundamental blocks of the systems and methods of the present invention.

By "electrode to the scalp" we mean to include, without limitation, those electrodes requiring gel, dry electrode sensors, contactless sensors and any other means of measuring the electrical potential or apparent electrical induced potential by electromagnetic means.

By "monitor the brain and nervous system" we mean to include, without limitation, surveillance of normal health and aging, the early detection and monitoring of brain dysfunction, monitoring of brain injury and recovery, monitoring disease onset, progression and response to therapy, for the discovery and optimization of treatment and drug therapies, including without limitation, monitoring investigational compounds and registered pharmaceutical agents, as well as the monitoring of illegal substances and their presence or influence on an individual while driving, playing sports, or engaged in other regulated behaviors.

A "medical therapy" as used herein is intended to encompass any form of therapy with potential medical effect, including, without limitation, any pharmaceutical agent or treatment, compounds, biologics, medical device therapy, exercise, biofeedback or combinations thereof.

By "EEG data" we mean to include without limitation the raw time series, any spectral properties determined after Fourier transformation, any nonlinear properties after non-linear analysis, any wavelet properties, any summary biometric variables and any combinations thereof.

A "sensory and cognitive challenge" as used herein is intended to encompass any form of sensory stimuli (to the five senses), cognitive challenges (to the mind), and other challenges (like a respiratory $CO_2$ challenge, virtual reality balance challenge, hammer to knee reflex challenge).

A "sensory and cognitive challenge state" as used herein is intended to encompass any state of the brain and nervous system during the exposure to the sensory and cognitive challenge.

An "electronic system" as used herein is intended to encompass, without limitation, hardware, software, firmware, analog circuits, DC coupled or AC coupled circuits, digital circuits, FPGA, ASICS, visual displays, audio transducers, temperature transducers, olfactory and odor generators, or any combination of the above.

By "spectral bands" we mean without limitation the generally accepted definitions in the standard literature conventions such that the bands of the PSD are often separated into the Delta band ($f<4$ Hz), the Theta band ($4<f<7$ Hz), the Alpha band ($8<f<12$ Hz), the Beta band ($12<f<30$ Hz), and the Gamma band ($30<f<100$ Hz). The exact boundaries of these bands are subject to some interpretation and are not considered hard and fast to all practitioners in the field.

Systems and methods for analyzing and assessing brain health signatures and cognitive status.

The systems and methods of the present invention comprise devices and methods relating to a brain-computer interface (BCI) which apply EEG (electroencephalograph) electrodes to a subject and monitor the minute electrical signals from the brain non-invasively to create a personalized biometric brain health signature. The components of the system fall generally into one of three main categories, including but not limited to, (i) the hardware and devices to record the EEG signals and apply various external perturbations to stimulate, activate or drive the central nervous system, (ii) the test battery and paradigms to challenge the brain during the EEG recording session, including the combinations of resting states (e.g. Eyes Closed) with dynamic or stimulated states, and (iii) the post-EEG signal processing and derived classifiers, either in real-time via fast electronics or via offline analysis once the analog signals have been digitized into bytes by an Analog to Digital Converter and stored on a mass storage device like a hard drive or USB flash drive.

The systems and methods of the present invention focus on various BCI test batteries of physiological function using the computer in two ways (see FIG. 1): (i) to receive EEG data from a scalp electrode device 12 and (ii) to also deliver much of the test battery 24 to the subject. We currently envision the EEG means of detection as a scalp EEG received by a computer 16 but the computer will also deliver the test and analyze the results. It will receive the EEG data and apply an algorithm 18 to define normal baseline functioning in an individual and to check for deterioration in brain health. For any individual 10, the systems and methods of the present invention could be added as a quantitative assessment of brain health. For instance, if someone progressively becomes demented, or sustains head injury, the pathophysiological brain changes could be assessed serially by applying the BCI test battery. In more specific diseases, this can be used in a customized way to track disease progression and treatment efficacy in disorders such as Alzheimer's disease, Schizophrenia, Depression, Anxiety, Bipolar illness, and pain disorders. In general, the utility of the present invention has general use as a wellness check. Additionally, the present invention can be used for at least three distinct applications as a person acquires a disease, including: (i) tracking disease progression, (ii) guiding treatment and therapy (e.g. dose, timing, types of medicines), and (iii) as therapy via biofeedback, providing a means for someone doing mental exercises to try to adjust the EEG signature back to normal.

FIG. 1 illustrates the systems and methods of the present invention, including the scalp electrodes 12 on subject 10, the cell phone or PDA 14, the computer 16, signal processing 18, personalized physiological brain health biometric signature 20, for use in monitoring disease progression, treatment optimization, and biofeedback box 22. The test battery is illustrated in the box 24 to the left.

Figure 2:
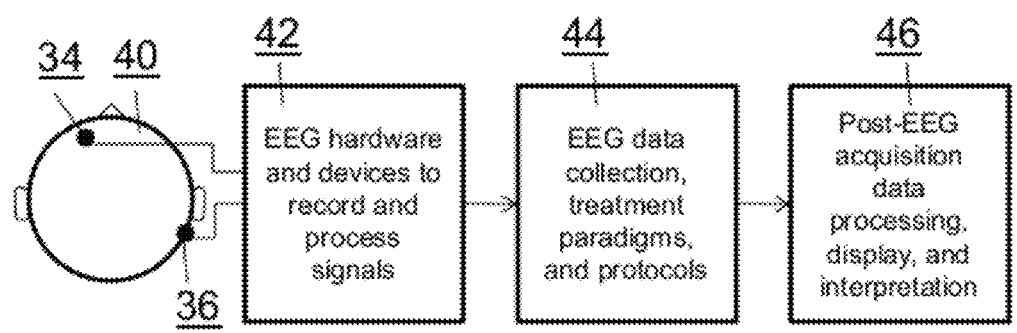
FIG. 2 illustrates an alternate schematic of the overall system for the creation and use of a personalized biometric brain health signature.

FIG. 2 illustrates the three main sets of elements of the systems and methods of the present invention, where the acquisition hardware 42 is connected to human subject 40 via electrode 34 relative to reference electrode 36. There can be another ground electrode, not shown in the figures to enable subtraction of any DC offset potential to create a true AC signal for electronic amplification purposes. The data collection test battery or paradigm is represented by 44, and the post-signal processing and data analysis is represented by 46.

More particularly, FIG. 2 illustrates an alternate schematic of the overall system for the creation and use of a personalized biometric brain health signature. Electrode 34 and counter-electrode 36 sit on scalp 40, the electrical potentials are recorded and processed in the EEG hardware 42, then collected during the treatment paradigm 44 for post-processing, display and interpretation 46. The electrodes or sensors 34 and 36 can be AC coupled to the amplifier or alternatively DC coupled to the amplifier.

It is evident that concealing a single dry electrode and reference and ground electrodes in a baseball cap or hat would lead to a concealed means to record EEG data in a more public setting without attracting attention to the user. Military and sports helmets could have the EEG electrodes embedded into them with miniaturized electronics modules transmitting the EEG data in real-time wireless interface (like Bluetooth™ or Wi-Fi) to nearby receivers for analysis, storage, and post-acquisition processing. Sweatbands and auditory, visual combinations like virtual reality goggles are also contemplated for different embodiments of the present invention.

Figure 3:
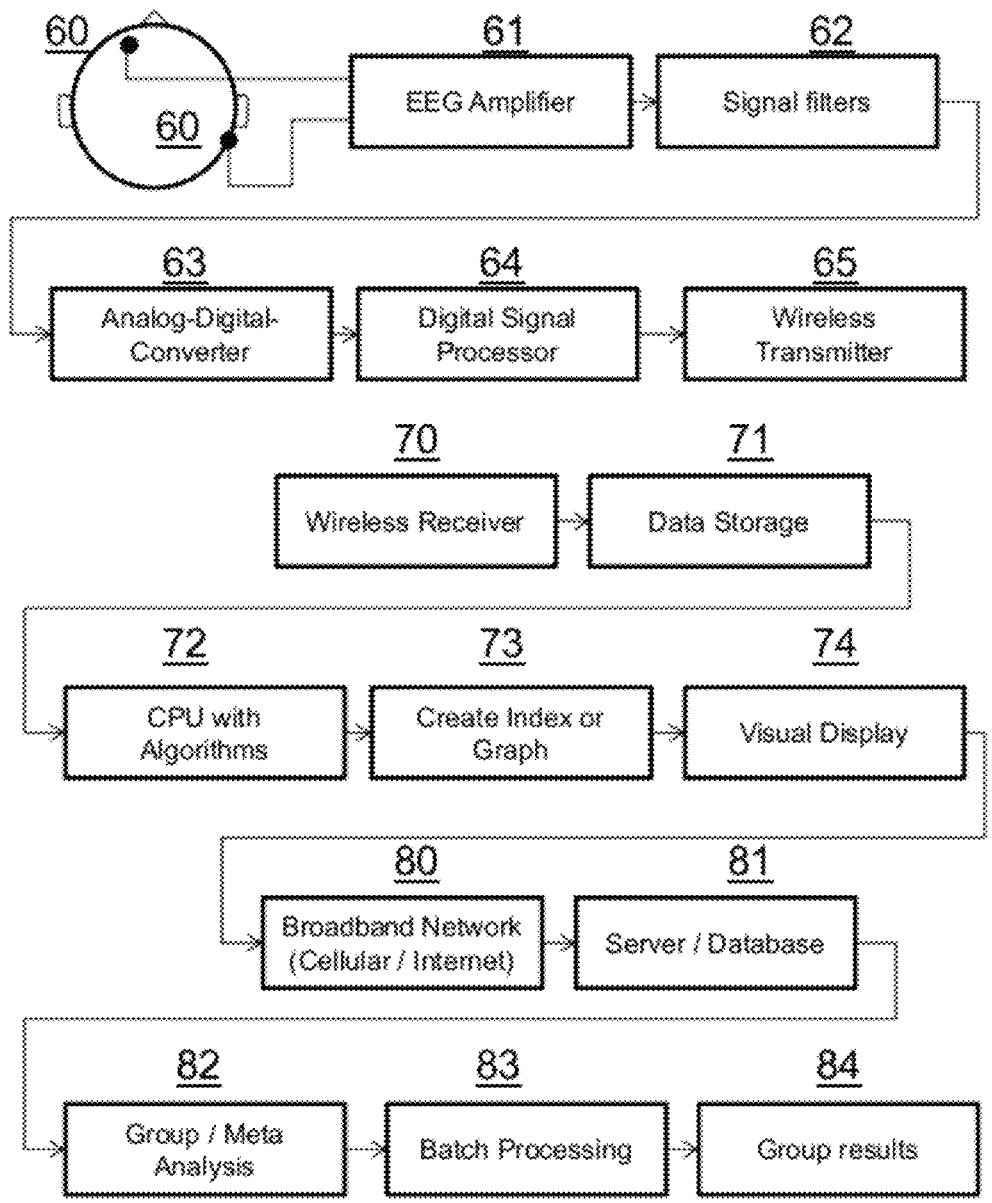
FIG. 3 illustrates an alternate and refined breakdown of the components of the overall systems and methods of the present invention.

FIG. 3 illustrates an alternate and refined breakdown of the components of the overall systems and methods of the present invention. The signals from electrodes 60 are fed to the EEG amplifier 61, then pass through signal filters 62 to analog-to-digital converter 63 to a digital signal processor 64 to a wireless transmitter 65. The wireless data stream is received in wireless receiver 70, sent to data storage 71 for computation in CPU 72 with associated algorithms where index or graph 73 is created and displayed on visual display 74. From there, a broadband network 80 moves the data to a database on a server 81 for group/meta analysis 82 in batch processing 83 for production of group results 84.

What is the brain-computer interface?

The brain-computer interface is the means of measuring brain cortical electrical activity with a variety of EEG techniques known in the art, including but not limited to, 25 the 10-20 international system, or more customized electrode arrays which may include only a few regional electrodes or even a single strategically placed electrode. The detector can also include a magneto encephalogram (MEG).

Figure 4:
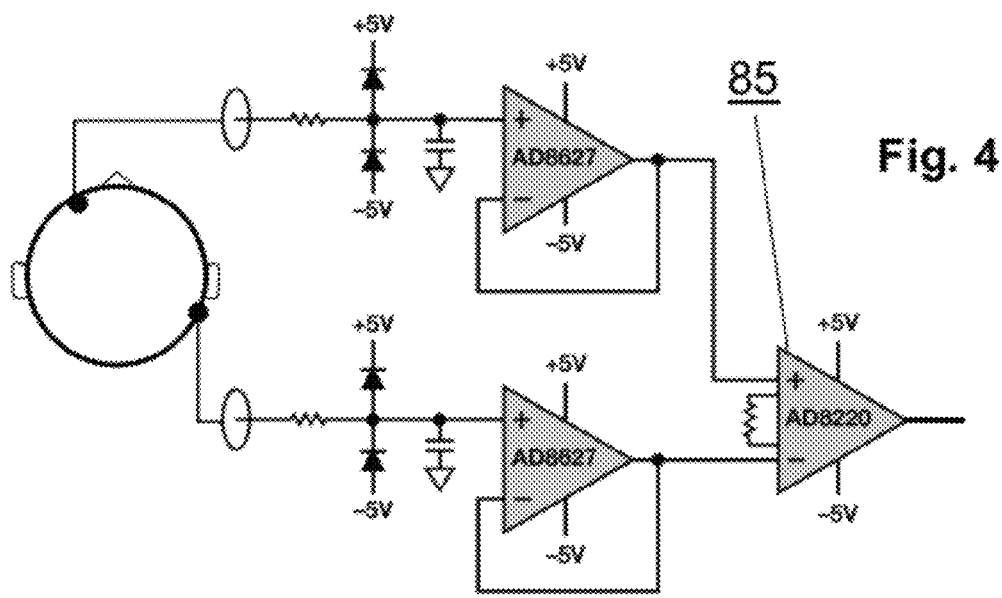
FIG. 4 illustrates an electrical circuit suitable to record from one reference or two differential electrodes.

FIG. 4 illustrates an electrical circuit suitable to record from one reference or two differential electrodes (courtesy of Analog Devices bio signal technical note). This is a detailed example of EEG amplifier 61 of FIG. 3 and a part of block 42 of FIG. 2.

Figure 5:
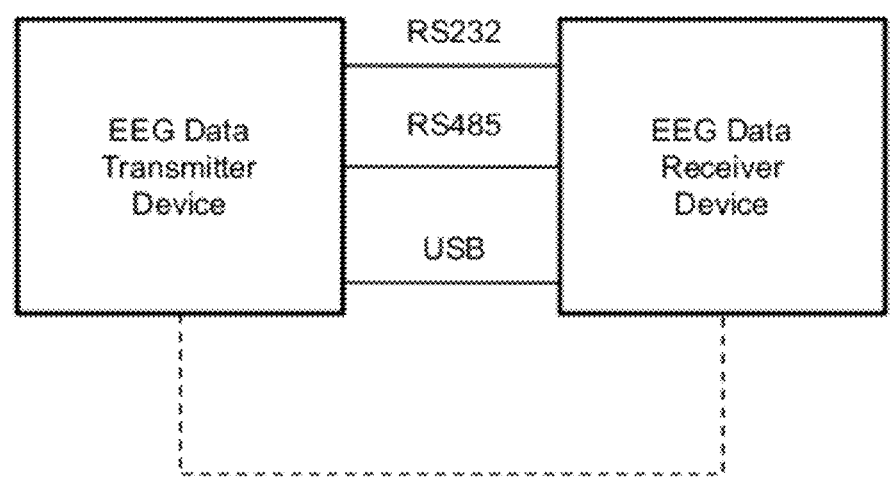
FIG. 5 is a block diagram showing various non-limiting digital transmission protocols that can be implemented to move the digital EEG data from the data transmitter to the data receiver.

FIG. 5 illustrates a block diagram of various digital transmission protocols that can be implemented to move the digital EEG data from the data transmitter to the data receiver, including wired connections (e.g. RS232, RS485, USB) as well as wireless means (e.g. Bluetooth, ZigBee, Wi-Fi, Wi-Max).

The interface of the EEG detection device with the computer can be facilitated through a standard wired or wireless interface (e.g. Bluetooth™ or Wi-Fi) or alternatively, a wireless protocol to use a smart phone or PDA (e.g. iPhone™ or BlackBerry™ device having a Bluetooth™ interface) as the intermediary in the process. The functional EEG signals will be detected as voltage as a function of time under either resting conditions or during applications of the various cognitive and sensory test battery maneuvers. The voltage time series can be transformed and plotted via Fast Fourier Transform (FFT) for spectral analysis and construction of the power spectral density (PSD), where these spectral signatures under baseline as well as under the various test battery conditions, constitute a functional bio-signature of a given individual's brain and nervous system. The power spectral signatures can be subjected to multi-parametric analysis, looking at relationships between two electrodes or coherence between signatures amongst two or more electrodes. The relationship between distinct frequency bands can also be utilized (e.g., alpha to theta ratio).

Figure 6A:
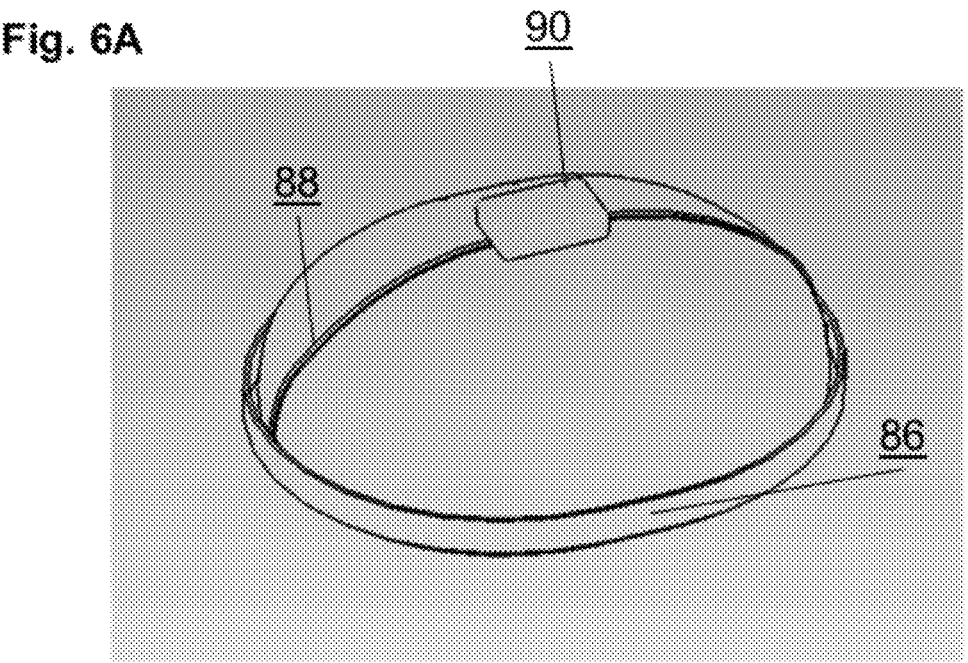
FIG. 6A is a perspective view of an EEG headset embodiment to collect the EEG electrical signals within the interior of a baseball cap or military helmet.
Figure 6B:
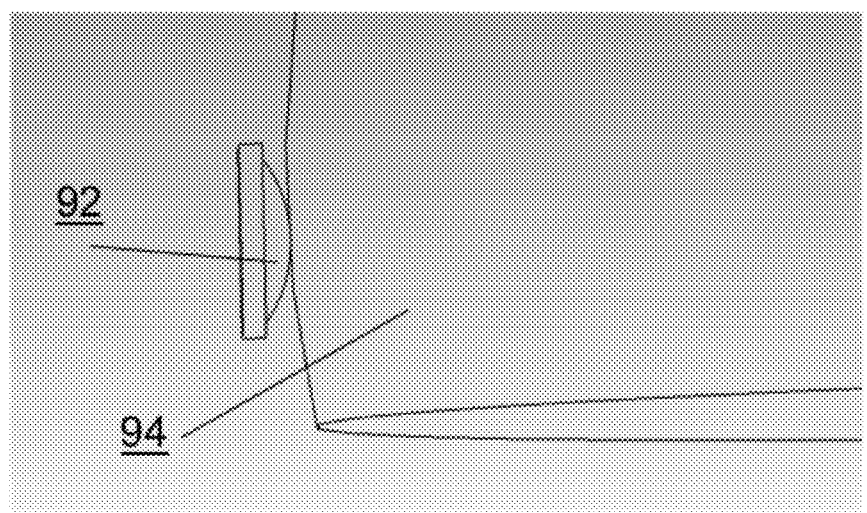
FIG. 6B is a close-up view of the dry EEG sensor portion of the EEG headset showing the electrode within the headband touching the scalp.

FIG. 6A illustrates an alternative EEG headset embodiment to collect the EEG electrical signals within the interior of a baseball cap or military helmet, where an electronics headband 86 contains various electrodes that contact the scalp and send wired signals along support 88 to electronics module 90 which includes the components necessary to amplify, filter, digitize, process and wirelessly transmit the signals according to the present invention specifications. FIG. 6B illustrates a magnified view of the alternative EEG headset embodiment to collect the EEG electrical signals, showing electrode 92 within the headband 86 touching the scalp 94.

Figure 7A:
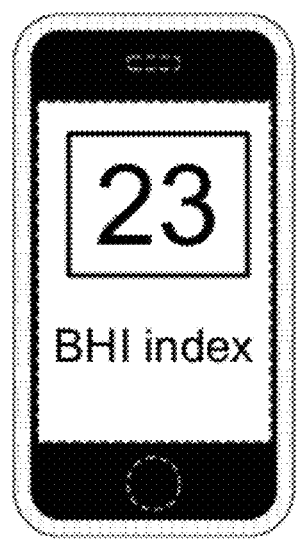
FIG. 7A illustrates an example client data receiver in the form of an Apple™ iPhone™.
Figure 7B:
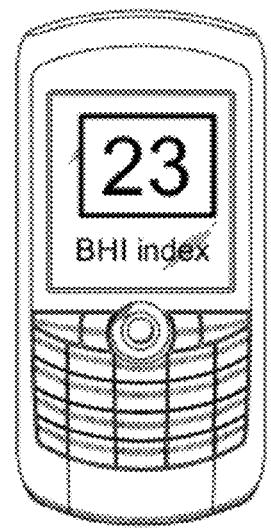
FIG. 7B illustrates an example client data receiver in the form of a Research in Motion™ BlackBerry™ smart phone or Nokia™ N95 data-capable smart phone.
Figure 7C:
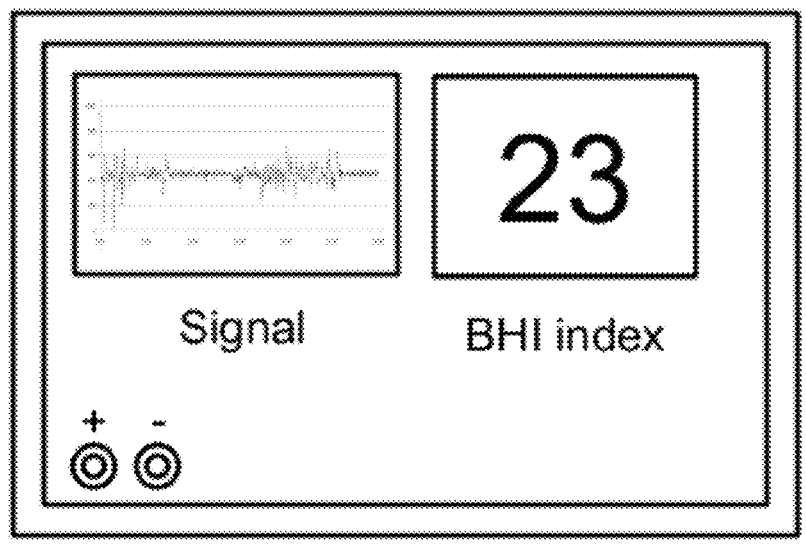
FIG. 7C illustrates an example client data receiver, custom designed for bench top or trolley cart use in a hospital or clinical setting.

As mentioned earlier, the receiving electronics can be in many forms including cell phone, PDA, PC or other device with microprocessor, such as a car. FIG. 7A illustrates an example client data receiver in the form of an Apple iPhone. FIG. 7B illustrates an example client data receiver in the form of a Research in Motion BlackBerry smart phone or Nokia N95 data capable smart phone. FIG. 7C illustrates an example client data receiver custom designed for bench top or trolley cart use in a hospital or clinical setting.

Figure 8:
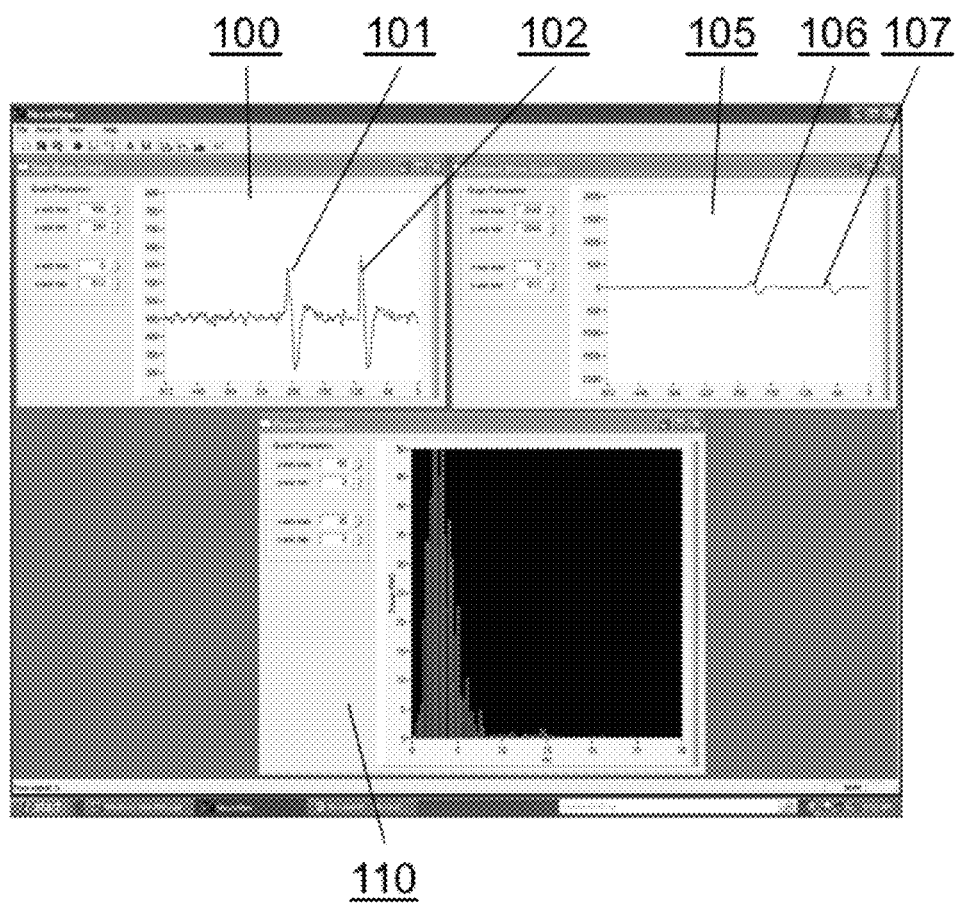
FIG. 8 is an example screenshot from a personal computer collecting single dry electrode EEG raw, filtered, and PSD data from within Neuroview™ software.

A preferred embodiment of the present invention is in the form of a personal computer running software designed to receive the EEG data through either a wired or wireless interface as exemplified in FIG. 5 above. FIG. 8 presents an example screens hot from a personal computer collecting single dry electrode EEG raw 100, filtered 105, and PSD 110 data recording at 128 samples/sec using a single dry electrode from a NeuroSky™ MindSet™ Pro headset using NeuroView™ software. One can further see two eye blinks indicated by 101 and 102 in the raw data panel 100. Notice these are not as easily visible in the filtered data window 105, but still appear as 106 and 107 respectively.

Spontaneous blinking is driven by a known brain circuit involving the basal ganglia and abnormal blink rates occur in neurological diseases related to dopaminergic transmission impairments, such as attention deficit hyperactivity disorder (ADHD), Schizophrenia, and Parkinson's disease (Esteban et al., 2004). This fact highlights just one non-limiting way in which the present invention can be used to assess specific brain circuits in health and disease. Quantification of blink rates via the myoelectric response at forehead scalp sensors is part of the systems and methods of the present invention.

Figure 9A:
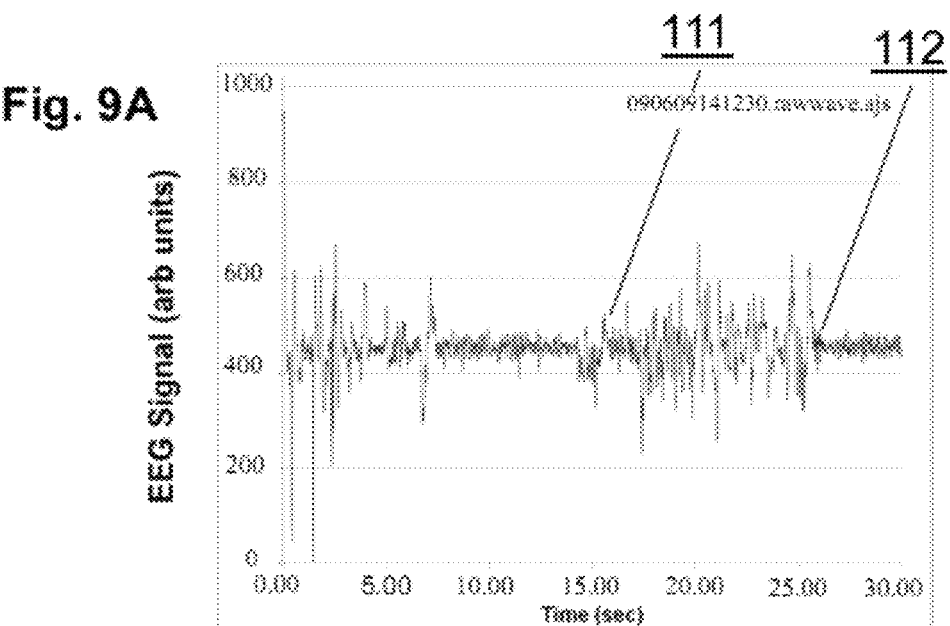
FIG. 9A is a graph showing a 30-second segment of raw EEG recording.

FIG. 9A presents a 30 second segment of raw EEG recording at 128 samples/sec using a single dry electrode Neuro-Sky™ Mind Set Pro headset using NeuroView™ software. Notice the y-axis scales from 0 to 1023 reflecting the 12-bit Analog-to-Digital Converter output in its uncalibrated format. After approximately 15 seconds, one can see a burst of activity at 111 where the amplitude of the EEG fluctuates with greater amplitude. It becomes quiet again at 112 near 27 seconds into the trace.

Figure 9B:
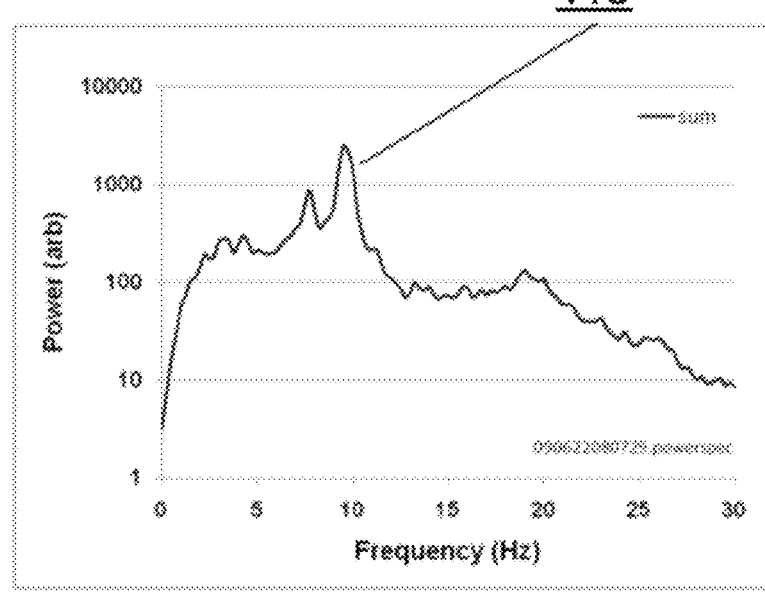
FIG. 9B is a graph showing a Fast Fourier Transformed (FFT) Power Spectral Density (PSD) trace calculated from a raw EEG signal collected in an Eyes Closed state.

FIG. 9B presents a Fast Fourier Transformed (FFT) Power Spectral Density (PSD) of a raw EEG signal collected for 3 minutes in a resting eyes closed state from electrode position Fp1. The absolute power is shown on the y-axis in a logarithm plot over several decades in arbitrary units with frequency bins from 0 to 30 Hz along the x-axis. One can quickly note the prominent peak 115 at 10 Hz in this subject, reflective of a pronounced alpha rhythm, first observed by Hans Berger in 1928. The alpha rhythm Eyes Closed state represents a state of alertness and readiness to receive input. It is remarkable to see this prominent feature from a single lead headset off a forehead position like Fp1, since alpha is typically observed in full electrode montages from the occiput of the head.

It will be noted that the systems and methods of the present invention consist of single electrode or sensor systems as just described above. Alternate embodiments of the invention include systems and methods that have two recording electrodes, enabling inter electrode measurements like synchronicity, concordance, and coherence to be calculated. Fp1 is a convenient location for a single electrode; however, the present invention also contemplates other positions on the scalp, including 01 or Oz over the occipital region of the brain.

FIG. 10A presents an analysis of the relative interday variability in a single 44 year old male participant. Five relative Power Spectral Density (PSD) traces from five independent days are plotted along with the geometric mean (black bold line, with the relative power shown on the y-axis in percentage of power with frequency bins from 0 to 30 Hz along the x-axis) showing excellent relative power variability from day to day. In the inset at the bottom of the figure, one can see the percent coefficient of variation (% CV) shown for the four major spectral bands of delta, theta, alpha and beta, all with % CV less than or equal to 25%.

FIG. 10B presents an analysis of the absolute interday variability in a single 44 year old male participant. Five absolute Power Spectral Density (PSD) traces from five independent days are plotted (with the absolute power shown on the y-axis in arbitrary units with frequency bins from 0 to 30 Hz along the x-axis) showing reasonably large interday absolute variability.

Figure 10C:
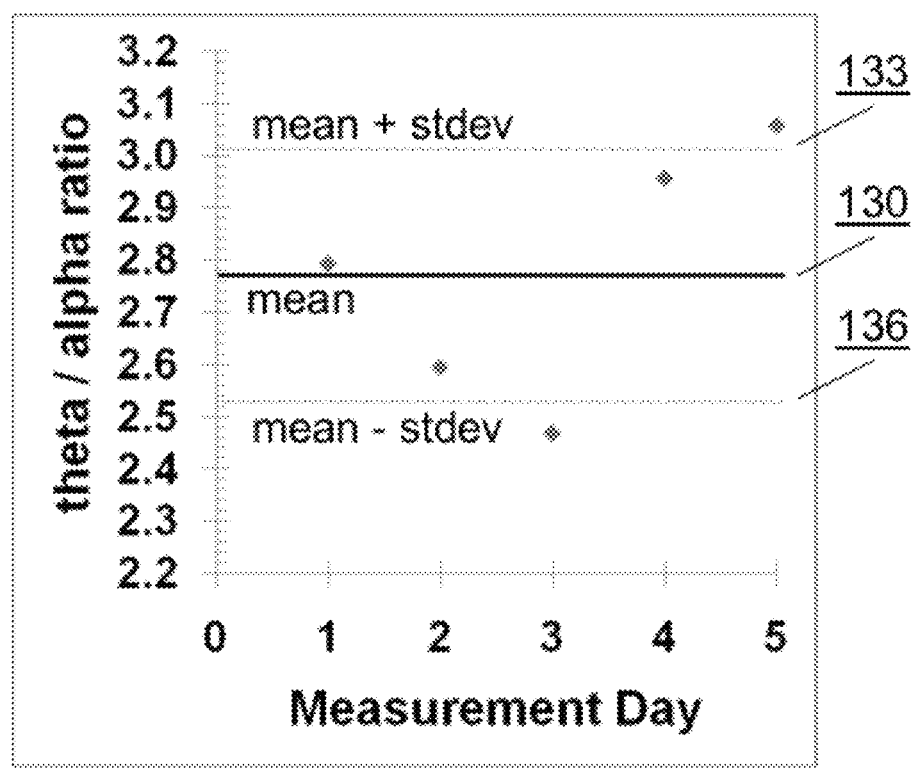
FIG. 10C is a graph showing interday variability over five days in the ratio of the relative power in the theta to alpha bands (theta/alpha ratio).

FIG. 10C presents an analysis of the relative interday variability in a single 44 year old male participant. The ratio of the relative power in the theta to alpha bands (theta/alpha ratio) is plotted on the y-axis from the relative Power Spectral Density (PSD) traces from five independent measurement days (along the x-axis). The group mean, as well as mean plus standard deviation and mean minus standard deviation are also plotted as horizontal lines for reference. The data show an 8.8% CV in the theta/alpha ratio across the five independent days.

According to the systems and methods of the present invention, the computer also facilitates the input of some of the test battery which will be administered to a subject, to include the administration of specific frequencies of sound/auditory information and specific frequencies of lights via the eye, or alternatively administrating the cognitive test battery.

Figure 11:
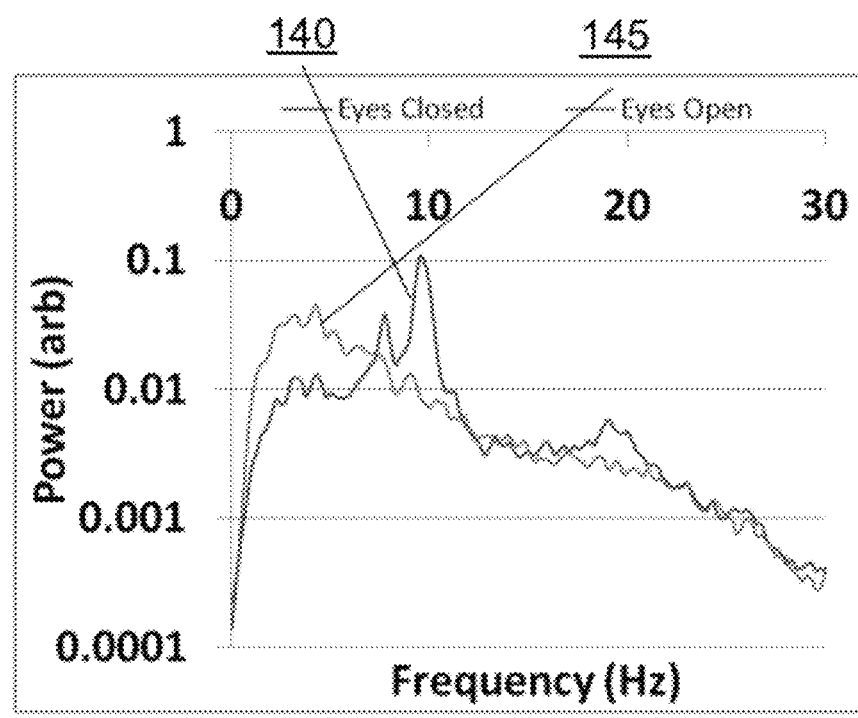
FIG. 11 is a graph showing a comparison of an Eyes Closed PSD trace and an Eyes Open PSD trace.

FIG. 11 presents a comparison of two Fast Fourier Transformed (FFT) absolute Power Spectral Density (PSD) traces of raw Fp1 EEG signals collected for three minutes in a resting Eyes Closed (EC) state 140 immediately followed by three minutes of resting Eyes Open (EO) EEG 145. The absolute power is shown on the y-axis in arbitrary units with frequency bins from 0 to 30 Hz along the x-axis. One can notice a prominent increase in the power of the peak near 10 Hz in the resting Eyes Closed (EC) state 140 indicative of increased alpha rhythm. Considering the logarithmic y-axis, the peak energy is quite prominent.

FIG. 12A presents the bin-wise ratio of the Eyes Closed (EC) divided by Eyes Open (EO) PSDs in a 44 year old male participant, showing an elevated alpha peak 160 greater than five-fold enhanced around 10 Hz. Note a value of unity (1.0) 165 represents no change in relative power from the EC to EO ratio. The EC/EO ratio is shown on the y-axis with frequency bins from 0 to 30 Hz along the x-axis.

FIG. 12B presents the bin-wise ratio of the Eyes Closed (EC) divided by Eyes Open (EO) PSDs in a 48 year old male participant, showing an elevated alpha peak 170 nearly five-fold enhanced around 10 Hz. Note a value of unity represents no change in relative power from the EC to EO ratio. The EC/EO ratio is shown on the y-axis with frequency bins from 0 to 30 Hz along the x-axis. It is important to note that the shape and magnitude of the alpha elevation in 12A and 12B appear different and represent unique biometric signatures of the brain physiology of each individual subject.

Another important aspect of the present invention is its ability to be conducted remotely. Thus, because of the simplicity and portability of the headset, it is possible to collect EEG data remotely using an internet connection to control the remote data collection PC while the headset rests on the test subject far away from the data collection specialist.

Figure 13:
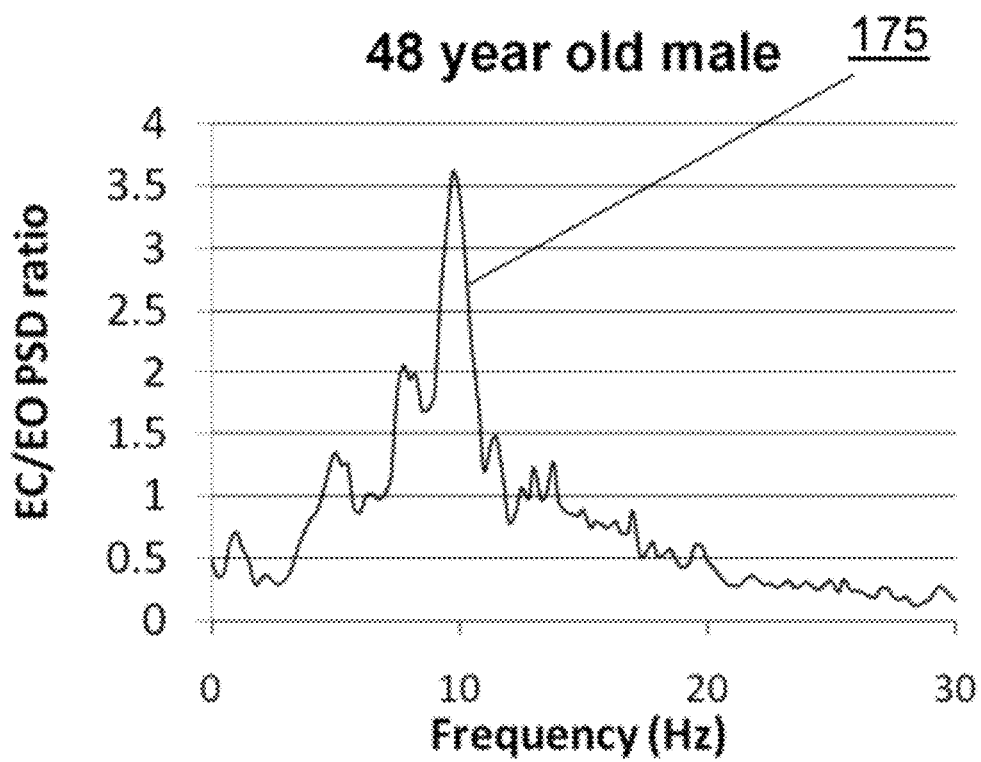
FIG. 13 is a graph showing a bin-wise ratio of EC divided by EO PSDs collected remotely from a subject in New York City by a test administrator near Philadelphia, Pa.

To present this point in explicit detail, FIG. 13 presents the bin-wise ratio of the Eyes Closed (EC) divided by Eyes Open (EO) PSDs in a 48 year old male participant who resided in Manhattan, NYC while the data collection specialist was remotely located near Philadelphia, Pa., demonstrating the ability to make real-time remote measurements through a network connection. Note the elevated alpha peak 175 nearly four-fold enhanced around 10 Hz. Note a value of unity represents no change in relative power from the EC to EO ratio. The EC/EO ratio is shown on the y-axis with frequency bins from 0 to 30 Hz along the x-axis.

Multiple Types of Sensory and Cognitive Stimuli

Rather than passively monitor the brain signals in isolation and in an uncontrolled manner, the methods of the present invention dynamically drive or stimulate the brain in a non-equilibrium or driven state, and compare the dynamical EEG response of the system to the quiescent resting (eyes closed) state. There are a multitude of possible stimuli, many of which have been used in the functional magnetic resonance imaging (fMRI) setting to look for the brain activity associated with various stimuli. As such, stimuli can be any one of the five senses, including visual or optical stimuli, auditory stimuli, olfactory stimuli, taste stimuli to the tongue or gastrological stimulation to the stomach, or touch stimuli to various components of the skin. Additionally, cognitive tasks are also part of the systems and methods of the present invention, in the form of stimuli provided to create functional EEG biometric brain health signatures.

Additionally, brain signals acquired with and without sensory input during spontaneously varying states of consciousness including all sleep stages, obtundation, and coma can be compared to such brain signals acquired during awake states. Other challenges include, without limitation, a $CO_2$ respiratory challenge, balance challenges on wobbly plates or with optical glasses that distort one's balance, or with virtual reality goggles that enable immersion into 3-dimensional worlds as they challenge the vestibular system.

Figure 14:
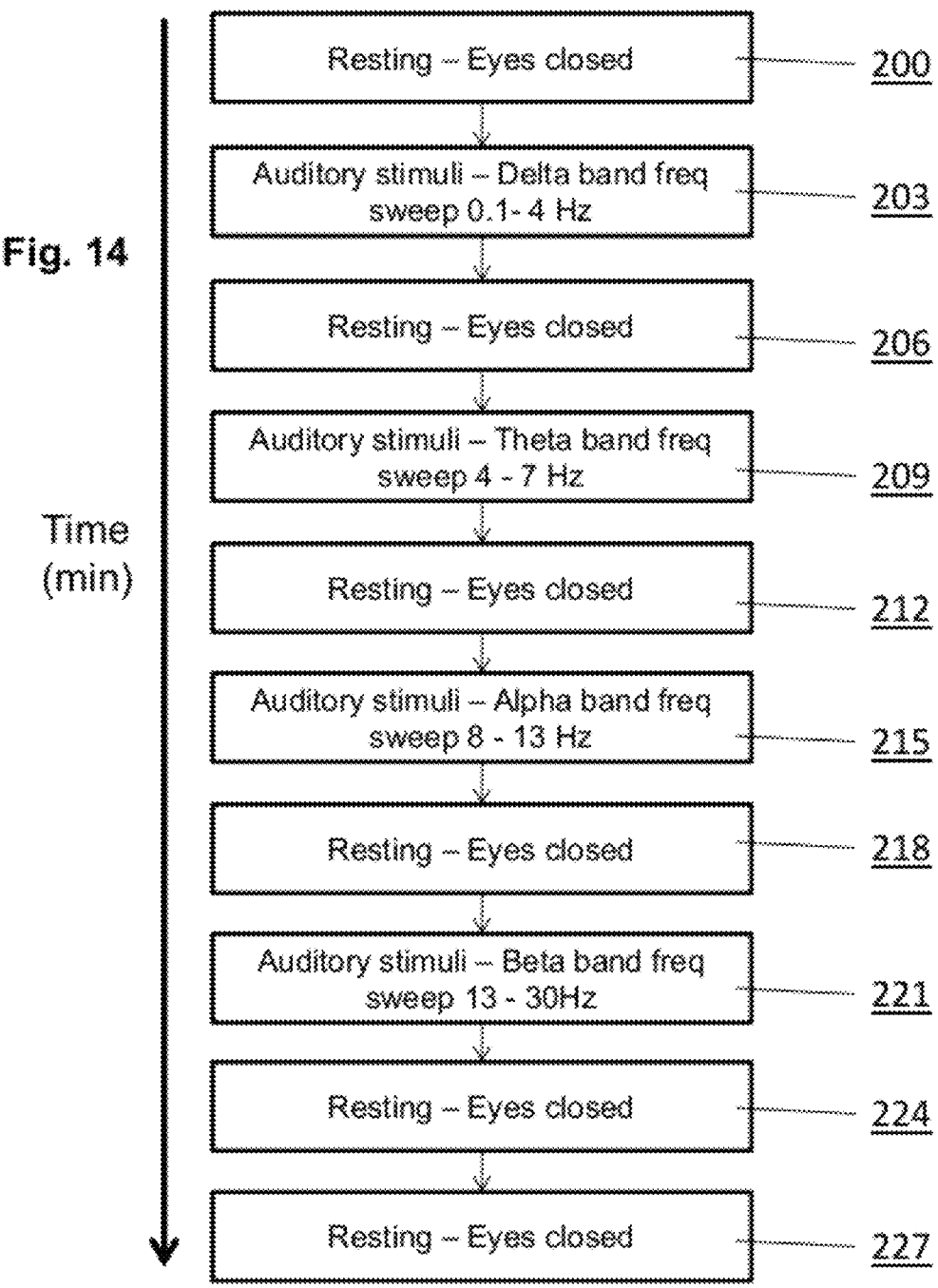
FIG. 14 is a block diagram illustrating a multiple input auditory stimulation data acquisition paradigm.

FIG. 14 illustrates an auditory stimulation data acquisition paradigm in which a number of tasks are conducted where auditory stimulation is provided to the subject in a prescribed sequence to collect auditory stimulation EEG data. As time moves downwards in the figure, each block represents two minute bins of data recording. The protocol starts collecting EEG data in a resting Eyes Closed state 200, followed by auditory stimulation in the delta band as a frequency sweep from 0.1 to 4 Hz 203, followed by a resting Eyes Closed 206, followed by auditory stimulation in the theta band as a frequency sweep from 4 to 7 Hz 209, followed by a resting Eyes Closed 212, followed by auditory stimulation in the alpha band frequency as a sweep from 8 to 13 Hz 215, followed by a resting Eyes Closed 218, followed by auditory stimulation in the beta band as a frequency sweep from 13 to 30 Hz 221, followed by a resting Eyes Closed 224, followed by a final resting Eyes Closed 227. This 10 task sequence takes 20 minutes.

One notes that the frequencies referred to in FIG. 14 are the beat frequencies of the auditory stimulation, not the pitch frequency which is often scaled from the beat frequency into the 100-400 Hz audio range.

Figure 15:
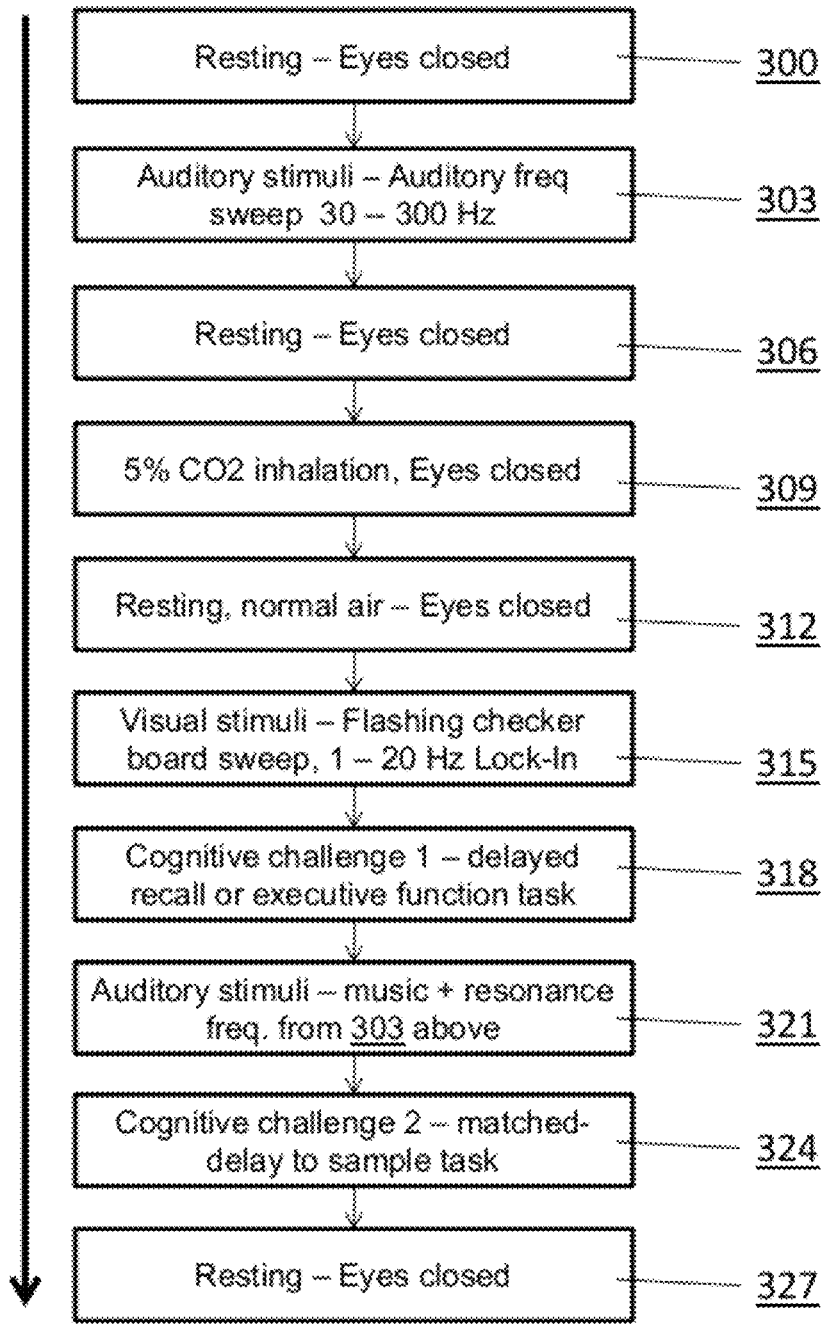
FIG. 15 is a block diagram illustrating a combined sensory stimulation and cognitive challenge data acquisition paradigm.

FIG. 15 illustrates a mixed sensory stimulation and cognitive challenge data acquisition paradigm in which a number of tasks are conducted in a prescribed sequence to collect dynamic EEG data. As time moves downwards in the figure, each block represents two minute bins of data recording. The protocol starts collecting EEG data in a resting Eyes Closed state 300, followed by auditory stimulation in the form of an auditory sweep in frequencies from 0.5 to 30 Hz over 2 minutes 303, followed by a resting Eyes Closed 306, followed by 5% $CO_2$ inhalation with Eyes Closed 309, followed by a resting Eyes Closed with normal air inhalation 312, followed by visual stimulation in the form of a flashing checker board sweep from 1 to 20 Hz 315, followed by a first cognitive challenge in the form of delayed word recall or executive function task 318, followed by auditory stimulation in the form of music superimposed with the frequency in the sweep that demonstrated the most response from the frequency sweep from 303 above 321, followed by a second cognitive challenge in the form of a delayed match to sample task 324, followed by a final resting Eyes Closed 327. This 10 task sequence takes 20 minutes.

One can see that the test battery described above, according to the systems and methods of the present invention, stimulate, activate or drive brain physiology in the hard wired, auditory pathway, and somato-sensory/pain pathway, and visual pathways. These pathways have various means of activation and each has been picked for specific neurobiological reasons.

Thus, even with a limited number of sensors that directly measure local cerebral cortex electrical activity, the systems and methods of analysis allow the monitoring of neurophysiology in a wide range of brain circuits including nerves, spinal cord, brain stem, thalamus and other deep and surface brain structures.

Preferred embodiments are tailored for each particular task or utility on a case by case basis. For instance, it may be preferable to utilize a four task battery for one disease state diagnostic, a five task battery that may include one cognition task for a second disease state, and a six task battery for a third disease state of interest. To monitor compound effects in investigational clinical trials, it may be preferable to include a seven task battery or eight task battery, depending on the physiological circuits to be probed and how the be classifiers and signatures can be created and utilized. Preferred embodiments look at each situation on a case by case basis and determine what works well for each situation. Thus there are multiple systems and multiple methods of the present invention.

Use of a Respiratory $CO_2$ Challenge

An additional embodiment of the present invention employs a resting state respiratory carbon dioxide ($CO_2$) challenge. It is contemplated that it would be best to conduct this stimulation at the end of the battery, since one would not want to interfere with the baseline levels. The idea is quite simple and yet very effective. One can deliver via a face mask or breathing tube 5% $CO_2$ in air and take an EEG or MEG recording over a 5 minute epoch; once the $CO_2$ has achieved the desired level in the end-tidal $CO_2$ (i.e. what you are breathing out reaches 5%), one can record for 5 min of EEG. In an alternate embodiment of the present invention, one can deliver air/co2/air/co2/air such that the subject will not know what he or she is receiving, again in 5 minute epochs. Other non-limiting maneuvers could include inhaled general anesthetics, like nitrous oxide or halothane, in low doses to assure that the subject remain conscious. The aim is to show EEG signal changes before drowsiness appears in the human subject.

The $CO_2$ challenge can affect brain function in at least two ways: This maneuver is used routinely to increase cerebral blood flow since the cerebral vasculature is directly sensitive to $CO_2$. This aspect of the challenge can be used to observe changes in brain cortical activity under resting state and stimulus-driven states for disorders associated with reduced cerebral blood flow, to include but not limited to Alzheimer's disease and cerebrovascular disease.

Moreover, using a DC coupled EEG amplifier and DC-stable electrode sensors to record slow EEG signals, the respiratory $CO_2$ challenge can also be used to measure cerebral blood flow and cerebrovascular reserve (Voipio J, Tallgren P, Heinonen E, Vanhatalo S and Kaila K. Millivolt-Scale DC Shifts in the Human Scalp EEG: Evidence for a Nonneuronal Generator. J Neurophysiol 89:2208-2214, 2003. First published Dec. 11, 2002). These parameters are of important clinical value in cerebrovascular disorders and traumatic brain injury, as well as the early and late stages of Alzheimer's disease. These assessments are part of the systems and methods of the present invention.

The $CO_2$ challenge is also well known to differentially induce hyperventilation and anxiety in subjects with panic, bipolar, or major depression disorders. Although, actual attacks of panic or anxiety require longer exposures to higher concentrations of $CO_2$, the present invention utilizes the known responsiveness of EEG to hyperventilation, to capture distinctions in these disease states at much shorter and lower $CO_2$ exposure.

Pathway Activation

According to the systems and methods of the present invention, a key point is to activate pathways, rather than inhibit them. One wants to assess the brain's ability to react to stimuli, challenge, or test maneuvers. One enhances sensitivity by finding a way to calculate the change from baseline (i.e., from the eyes closed resting state EEG) and then compare with the sensory stimulus or cognitive challenge (e.g. auditory stimulation), and then identify the signature of what is the PSD change from baseline. For instance, a non-limiting example would be the PSD ratio of auditory to baseline; this could be an interesting signature, ultimately very sensitive and specific. If a given signature is changing or abnormal in a given subject, this could be observed and determined early, providing clinical utility to the patient, physician, and payor. Other means of plotting the data could be to look for coherence between two or more electrodes, power in various frequency bands, and basic PSD. More advanced algorithms including those derived from non-linear dynamical analysis and wavelet are part of the systems and methods of the present invention.

The test battery of the present invention provides for a means to create a generalized mental health assessment according to what is observed in an individual's functional biometric brain health signature. There is ample literature that shows that certain disease states characteristically alter EEG signals. The published literature documents various EEG disease state signatures, in particular how the PSD under the resting state condition is markedly altered from normal. Beyond disease states, the literature guides us in understanding that changes in the PSD are markedly altered under resting conditions or during working memory tasks. However, very few scientific publications address the issue of disease progression changes, as shown in EEG signatures, through the serial application of a test battery. Moreover, there is no literature that we are aware of regarding the much wider application of a test battery, looking at overall EEG changes when the test battery is administered consistently over time.

By analogy, when one goes for a cardiovascular assessment, one might take an echocardiogram (EKG) under resting conditions as well as while undergoing a variety of treadmill stress tests. Analogous to this, the methods of the present invention are test batteries for the brain and nervous system customized for EEG readouts. When someone is healthy, one can define normal BCI patterns and biometric signatures. The wider application of the quantitative BCI signature is in tracking disease by establishing a baseline "normal" EEG signature, then performing serial tests over time to monitor for progressive deterioration.

The present invention can, in a similar fashion, chart therapeutic response. For instance, there could be distinct clinical value in the case of acetyl cholinesterase inhibitors to determine which drug is best at what dose and timing. Thus if someone has a shifted EEG PSD to the left towards lower frequencies because of disease, and treatment normalizes the EEG back towards higher frequencies to the right, this could prove useful for drug optimization. There are several non-limiting examples in the literature in Alzheimer's and Parkinson's disease, specifically in the case of acetyl cholinesterase inhibitors, which support this line of reasoning.

Therapeutic reduction in states of consciousness, such as during treatment with inhalational or intravenous general anesthetics can be quantitatively tracked using the systems and methods described in the present invention. Alternatively, therapeutic enhancements of states of consciousness, such as emergence from general anesthesia or intoxication, or successful cardiopulmonary resuscitation can also be quantitatively tracked using the systems and methods described in the present invention.

Gastrological Stimulation as Part of the Present Invention

Additionally, one can view the brain and nervous system as a dynamical system and stimulate or activate it in other physiological ways as well. Various pharmaceutical and device-oriented treatments could lead to forces and perturbations on the brain in various interesting and important ways. For instance, the methods of the present invention comprise enhancing or reducing the amount of oxygen to the brain in order to assess its ability to adapt to changing oxygen content. Another embodiment of the present invention includes the use of fasted versus just-fed conditions with foods and liquids like Orange Juice (high in sucrose) or Jello-Brand Gelatin (also a fast absorber). The brain's EEG response and biometric brain health signature could be dramatically altered in response to rapid changes or slow shifts in overall biochemical supply of nutrients. Without limitation, other forms of dietary and nutritional perturbation are a part of the present invention. In particular, various vitamin components, including vitamins A, C, D, E, K, thiamin (81), riboflavin (82), 86, 812, Folic Acid, biotin or nutrients like iron, magnesium, are part of the methods of the present invention. In addition, specific caloric forms including carbohydrates, proteins, fats, ketone bodies, and alcohols are non-limiting gastrological stimulants of the present invention.

Olfactory Stimulation as Part of the Present Invention

Recently, Croy and colleagues (Croy I, et al, PTSD, but not childhood maltreatment, modifies responses to unpleasant odors, Int J. Psychophysiol. 2010 March; 75(3):326-31) found, using the "Sniffin' Sticks" threshold and identification test and analyzed chemosensory event-related potentials, that PTSD severity correlated significantly with odor identification scores and with parameters of event-related potentials in response to unpleasant stimuli. The results indicate preferential processing of unpleasant stimuli in PTSD patients irrespective of childhood history. With this, the systems and methods of the present invention include the use of olfactory stimulation, but rather than evaluate event-related potentials as Croy employed, the present invention aims to assess changes in state due to olfactory stimulation rather than sub second timing responses. This is very different than event related potentials. Nonetheless, Sniffin Sticks and the like are clearly important stimulants for evaluation of their effect on the PSD and other non-linear dynamics and wavelet biometrics in both healthy and disease or brain injured states.

Moreover, early deterioration and neurodegeneration in olfactory function has also been identified in Parkinson's and Alzheimer's disease and the detection of these abnormalities in the olfactory stimulated EEG signals are part of the systems and methods of the present invention.

Cognitive Tasks within the Present Invention

Additionally according to the systems and methods of the present invention, one can administer a working memory task, using the computer, for example delivering a series of X objects visually, and then asking the subject to keep them in memory, later asking for the proper sequence and identity. It is envisioned that one can sequentially increase the number of objects to be memorized from seven to as many as ten, without limitation. Many other cognitive tasks could also be used in the test battery, including other tests of distinct cognitive domains that focus on (i) attention, (ii) executive function, and (iii) short term memory, to name a few non-limiting examples. In a preferred embodiment, the cognitive tasks could be taken from a computerized test battery like the Cog State™ Ltd Research test battery. This would allow direct comparison of EEG data to the cognition battery results for comparison of both chronological age as well as cognitive age as assessed or scored by the computerized cognition battery. This cross-correlation method between the cognition data and the EEG data could enable discovery of EEG correlates to cognitive age or brain health, rather than simply chronological age of a subject based on time since birth.

Figure 16:
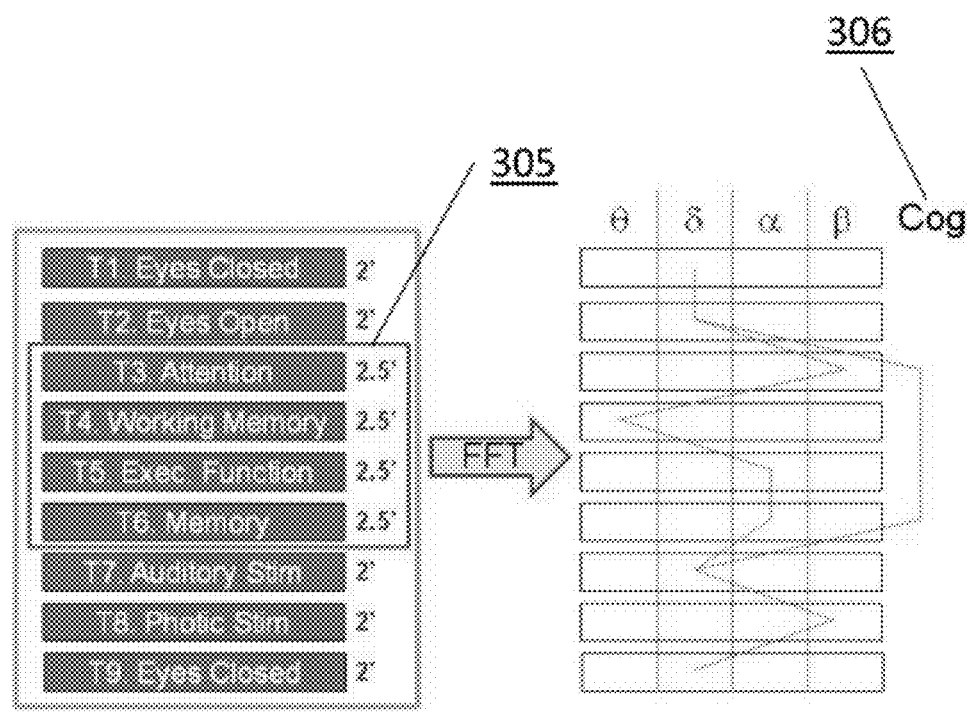
FIG. 16 is a block diagram illustrating a combined sensory and cognitive challenge data acquisition paradigm leading to a summary data table that includes both spectral EEG measures as well as cognitive variables like reaction time.

FIG. 16 illustrates a nine-task battery of cognitive and sensory stimulation from which simultaneous functional EEG data and its spectral properties is combined with computerized cognitive test measurements represented by 306 "Cog," including but not limited to reaction time and error/accuracy, to form multi-modal classifiers or discriminators of disease state (e.g. AD vs MCI vs control), injury state (mTBI vs control), or compound activated state (e.g. target engagement or pharmacodynamic end points). Task T3 Attention 305 could be the Identification task of the CogState Research Battery.

Figure 17:
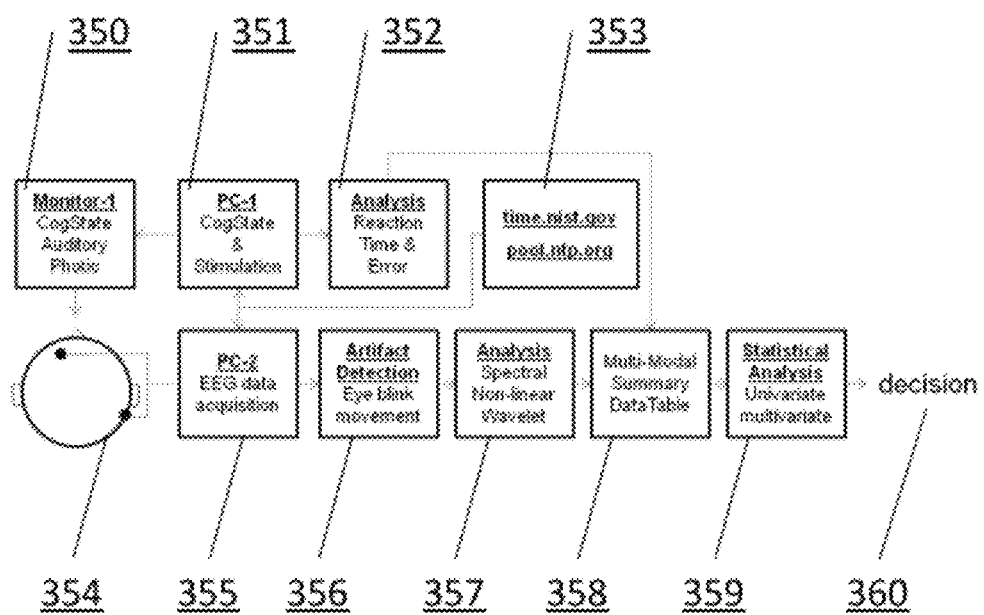
FIG. 17 is a block diagram illustrating a system capable of simultaneous cognitive testing and auditory/visual stimulation with functional EEG data stream recording on two synchronized computers.

FIG. 17 illustrates the CogScope™ block diagram using two independent computers, one for cognitive testing 351 and auditory/visual stimulation on a monitor 350 while the other PC 355 records the functional EEG data stream from the Bluetooth™ enabled EEG headset and electrodes 354. Both computers are synchronized 353 to within a second through the governmental time clock available at time.nist.gov through the internet. Analysis of the CogState data takes place on PC-1 352 while displayed on monitor 350. EEG data stored on PC 355 will be examined for artifacts on 356 and spectral, non-linear dynamics, and wavelet transform.

FIG. 18 shows a PSD taken during an Attention task on the CogState™ Research battery called Identification where the question "Is it red?" is asked for each trial playing card which is revealed. Events (either keystrokes or mouse clicks) are recorded and reaction times and error rates produced.

Figure 19:
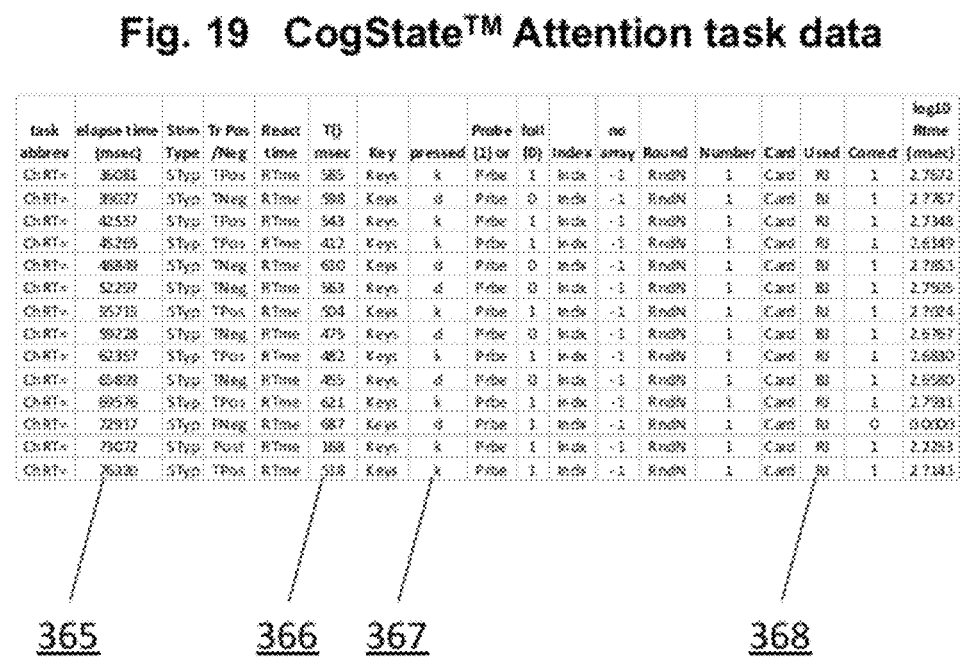

FIG. 19 illustrates a data table produced from the Cog State™ Research battery Identification task as an element of "Attention", showing the reaction time in milliseconds and whether the individual correctly identified the color of the playing card.

Figure 20:
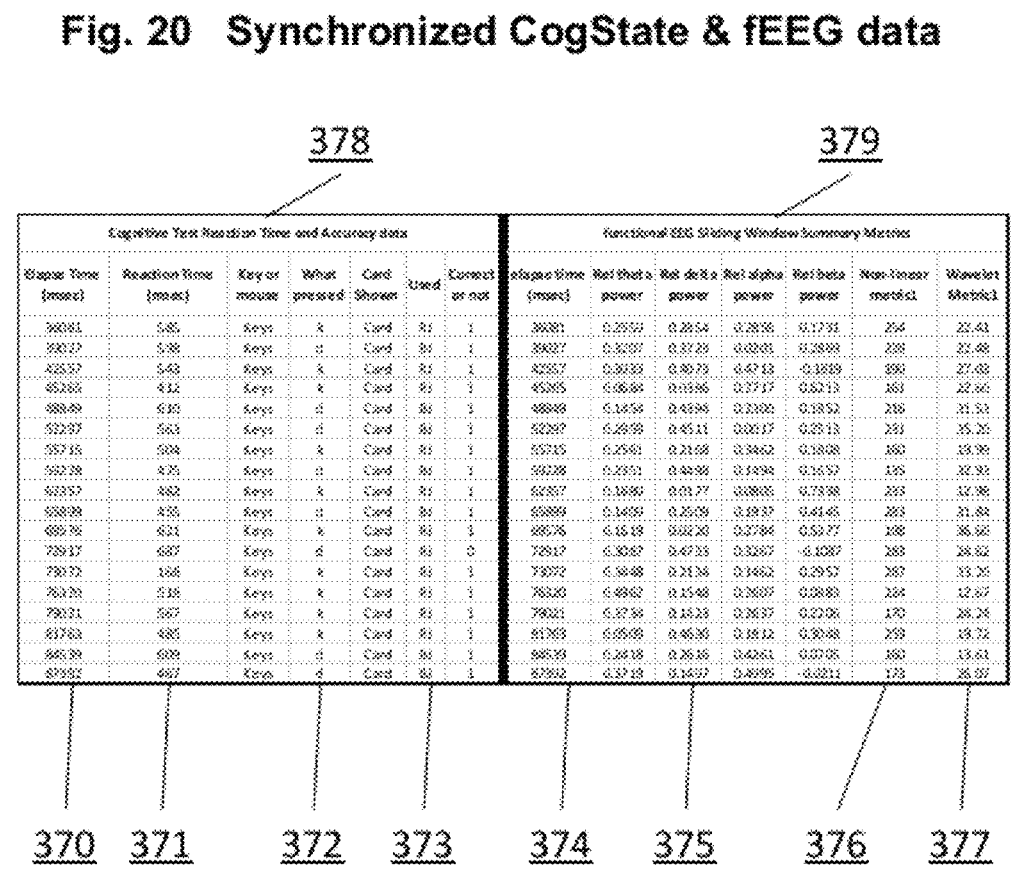

FIG. 20 illustrates a data table produced from the Cog State™ Research battery Identification task showing reaction time in milliseconds and error data synchronized with spectral, non-linear dynamical and wavelet summary metrics of the same period of simultaneous EEG while the trial was being conducted. This can enable trial dependent correlations and other global statistical metrics to be created, enabling multi-modal classifiers to be assessed in disease states, injury states, sleep states and compound states.

FIG. 21 illustrates the PasatScope™ block diagram using two independent computers, one for PASAT cognitive testing and auditory/visual stimulation while the other records the functional EEG data stream from the Bluetooth™ enabled EEG headset. Both computers are synchronized to less than a second through the governmentally available clock service at the time.nist.gov website.

FIG. 22 shows the time averaged PSD calculated from a 105 seconds Eyes Open data file acquired in a resting quiescence state versus in an Eyes Open activated state during the PASAT memory trial. This data was recorded using the University of Victoria, Department of Neuropsychology computerized PASAT™ at speed 2.4, then 2.0 and finally 1.6.

FIG. 23 shows the number of correct scores received by a 45 year old male volunteer at each of these three speeds.

FIG. 24 illustrates an audio track analysis of the composite audio from both the computerized program soundtrack that states the series of numbers to be serially added and the test subject who is being cognitively evaluated. The reaction times T1, T2, T3 are calculated as the interval of quiet from the last number stated by the computerized program soundtrack. These data were recorded into an Olympus™ VN-960PC digital voice recorder and then transferred by USB cable to the PC. Reaction times and accuracy are immediately extractable from the audio track analysis proposed herein.

Many other non-limiting computer cognition tests are contemplated as part of the present invention and include but are not limited to ImPACT, CogState™ Ltd's Research or Sport battery, PASAT (Paced Auditory Serial Addition Task), Drug Research Cognition Automated Test Battery, CAMCI (Computer Assessment of Mild Cognitive Impairment), Mindstream's™ computerized tests, Computerized Performance Testing Services' Computer Cognitive Testing Battery, Cambridge Cognition's CANTAB, Automated Neuropsychological Assessment Metrics (ANAM) of US Army, computerized versions of the Military Acute Concussion Evaluation (MACE), CDR Computerized Assessment System (CDR System, now acquired by United BioSource Corporation).

Photic Stimulation in the Present Invention

The present invention leverages photic stimulation as one element of the sensory and cognitive challenge battery within the systems and methods of the present invention. Using the methods and system of the present invention, we sought to demonstrate the ability to entrain the brain using photic stimulation at stimulus frequency F. Using either virtual reality display visors or LED goggles, the present invention is able to produce flashing light or checkerboards of light changing at a fixed or variable programmed frequency for a controllable period of time. The subject sits with eyes closed and light pulses flash on the eyes with very clear perception and mind alteration of the effect. Stimulation with light representing distinct colors of the visible, as well as infrared and ultraviolet spectrum is envisioned as part of the methods of the present invention.

One can stimulate the brain using white light photons at frequencies above the natural alpha rhythm of an individual or below at slower frequencies to induce the brain to take on temporal dynamics it is not normal accustomed to. Thus, stimulation frequencies of 12 to 20 Hz above the alpha rhythm have a different effect than photic stimulation at 5-8 Hz, where the light will pull the PSD of the volunteer leftwards to slower frequencies. It should be interesting to probe a brain and nervous system of a subject by applying photic stimulation at the natural alpha frequency of each personalized individual system.

In an alternate embodiment of the present invention, the alpha frequency of the individual is measured in a resting eyes closed state, and then the personalized peak alpha frequency is determined and used to set the frequency of the photic stimulation, using either percentages above or below, perhaps fold differences. In this way, each stimulation paradigm is personalized to each individual, a so-called personalized diagnostics analogous to personalized medicine.

In an alternate embodiment, the photic stimulation could be adjusted or swept from low to high frequency to evaluate a subject to see where their most responsive "resonant" like frequency is identified. Clearly, the frequency sweep could be from high to low as well. The stimulation could be in phase between the two eyes, out of phase, or the photic stimulation isolated to just one eye at a time, to probe brain circuits that emanate from the visual cortex but are observed in cortical structures distant from but connected with the visual cortex.

The ability to measure a response to the photic stimulation enables one to include this task into the battery of tasks to be conducted for brain state and functional analysis. This could include but is not limited to use in detecting, identifying, or monitoring diseased brain states like Alzheimer's disease or Schizophrenia, detecting, identifying, or monitoring injured brain states such as mild traumatic brain injury or stroke, or detecting, identifying, or monitoring brains under the influence of both legal and illegal drugs in an emergency room context where a patient presents with issues but is unconscious or uncooperative or in a clinical trial process of drug discovery in the pharmaceutical industry.

FIG. 25 shows the calculated PSD in an Eyes Closed but awake brain state when a pair of LED goggles are flashing through both eyelids in phase and entrain the brain's EEG cycle. One can see a primary peak 540 in the PSD at the frequency of flashing light (F=10 Hz) as well as the first harmonic 550 (F=20 Hz), indicating there are probably non-linear dynamics involved in the process.

FIG. 26 shows the calculated PSD in an Eyes Closed but awake brain state when a pair of LED goggles are flashing through both eyelids in phase and entrain the brain's EEG cycle. One can see a primary peak 560 in the PSD at the frequency of flashing light (F=12 Hz) as well as the first harmonic (F=24 Hz) 570, indicating there are probably non-linear dynamics involved in the process. It would be interesting to observe higher frequencies where three times the stimulation frequency F is prominent as a peak an individual PSD.

Auditory Stimulation in the Present Invention

The auditory stimulation includes but is not limited to isochronic tones, binaural beats, or monaural beats, in addition to direct pure tones. In each case, there is an opportunity to stimulate and probe various parts of not only the auditory cortex, but also larger regions of cortical matter and circuits based on the fact that we are recording signals at Fp1 on the forehead. This can be done with various software programs like Neuroprogrammer3, Rutgers University Beats, and MATLAB™.

Isochronic tones can be output from a PC soundcard with beat frequency ranging from 1 to 30 Hz, often in the range of 2 to 20 Hz and most preferably in the range 6 to 18 Hz. This corresponds to optimized pitch frequencies from software programming of from 147 Hz to 200 Hz. Parameters of the isochronic tones included square waves, 90 degree phase, sine pitch, with 1-20 Hz corresponding to 100-200 Hz pitch. Monaural beats can be output from the PC soundcard with beat frequency ranging from 10 to 20 Hz in 2.5 Hz steps, which corresponded to optimized pitch frequencies from the NP3 program of from 147 Hz to 200 Hz central frequency with beat frequency symmetric. For example, a 20 Hz beat corresponded to a central pitch of 200 Hz, with tone 1 and tone 2 corresponding to 190 Hz and 210 Hz respectively. The amplitude was put on full both at the Windows7™ soundcard driver as well as within the NP3 program. The sound can be relayed through the Bluetooth™ interface to the audio speakers built into the Mind Set Pro™ headsets. Lastly, binaural beats can be output from the PC soundcard with beat frequency ranging from 10 to 20 Hz, which corresponded to optimized pitch frequencies from NP3 of 10 Hz to 200 Hz.

Figure 33:
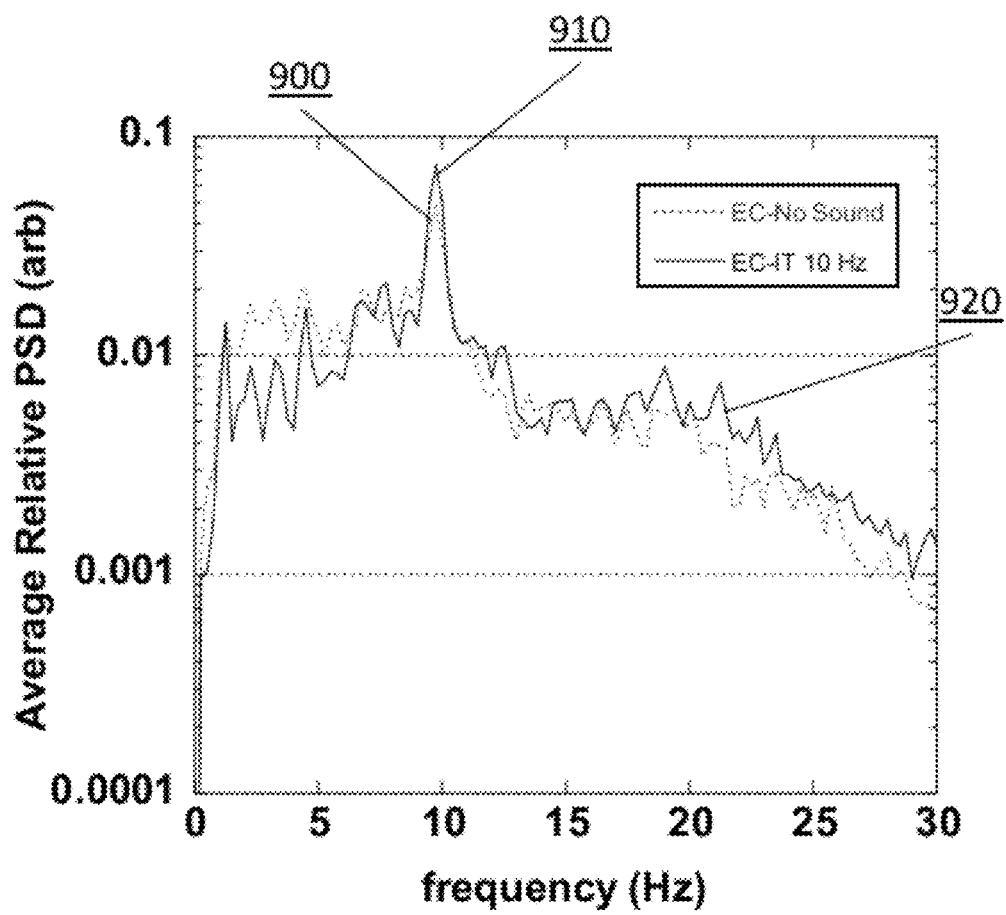
FIG. 33 is a graph comprised of two traces showing time averaged relative PSDs for isochronic tones comparing Eyes Closed no tone (dotted line) versus 10 Hz beat frequency isochronic tones (solid line).

FIG. 33 compares the averaged relative PSD comparing an Eyes Closed no sound stimulation state to an F=10 Hz isochronic tone stimulation state with pitch approximately 140 Hz. The Eyes Closed no sound trace 900 shows modest alpha power at 10 Hz; however upon 10 Hz isochronic tone stimulation with Neuroprogrammer3 software, there is an enhancement in the alpha rhythm 910 and there appears extra power around 20 Hz at 920, consistent with a harmonic like appearance of 2F in the power spectrum. The effect in the PSD is more subtle than the photic stimulation.

Alpha Rhythm Monitoring as a Means to Monitor the Brain and Nervous System

One of the earliest observed dynamic changes in the human scalp EEG was the marked enhancement of the alpha (8-12 Hz) band upon closing of the eyes. This enhancement of alpha rhythm in Eyes Closed vs. Eyes Open state is most prominent over the occipital scalp. However, we show that this phenomenon can be observed over the scalp of the forehead as well (FIGS. 11, 145 and 140). The magnitude and exact frequency band for the alpha response to eyes closing may be different in different individuals, but we show it to be a reproducible personal biometric feature (FIG. 10A). The induced alpha band is believed to be an "idling" rhythm during conscious states that reports a state of readiness of the thalamocortical system for input of sensory information (Paiva S, Paiva J M. New vistas for alpha-frequency band oscillations. Trends Neurosci. 2007 April; 30(4):150-8). In the Eyes Closed state, the alpha rhythm can be attenuated by the onset of sleepiness, i.e. reduced readiness of the thalamus to sensory input, or by sensory input itself (transitioning of the brain from idling to perceiving mode) (Paiva and Paiva, 2007). The attenuation of the alpha rhythm by perception of stimuli is embodied in the systems and methods of the present invention as a means for testing the integrity of neuroanatomical pathways, which convey the presented stimulus. A non-limiting test contemplated as part of the present invention involves the peripheral application of a temperature stimulus, such as an ice cube or milder non-painful temperature stimulus, to the right hand. In an awake individual with eyes closed, this stimulus produces a suppression of the alpha rhythm (FIG. 27B relative to FIG. 27A) in the Fp1 electrode over the forehead. This test signifies the intactness of temperature receptors, specific types of nerve fibers in peripheral nerves, specific spinothalamic spinal cordtracts, brainstem pathways, and thalamic pathways conveying the temperature sensation information from the right hand. One can imagine applying the same test approach to the left hand, right or left lower extremities, or to the whole body in a dermatomal mapping approach to document the health of nervous system circuits. Likewise, other sensory modalities such as vibration and proprioception can be used with the alpha attenuation paradigm to determine intactness of the specific nerve fibers and neuroanatomical pathways involved.

Driving Force F Monitoring as a Means to Monitor the Brain and Nervous System

The application of specific sensory stimuli at pre-specified frequencies F constitutes another aspect of the systems and methods of the present invention for testing the integrity of neuroanatomical pathways. Non-limiting examples of this approach involve the delivery of visual or auditory stimuli to a subject at specific oscillating frequencies F during simultaneous measurement of scalp potentials and observation of the EEG response for accentuation at the stimulus frequency or harmonics thereof. FIG. 25 shows an example of photic stimulation at 10 Hz frequency, where the response of the brain at the stimulation frequency F is seen as 540 with a super-harmonic of 20 Hz as 550. A second example is shown in FIG. 26 with frequency F 560 and harmonic 570. Unlike brain region specific time-locked sensory evoked potentials, the enhancement of the EEG at the "driving" stimulus frequency can be detected over many scalp areas as this phenomenon involves the whole brain. This facilitates the utilization of this approach for examining and monitoring the brain and nervous system. As in the case of the alpha attenuation approach described above, the stimulus frequency F driving approach can be applied to multiple neuroanatomical pathways and can utilize multiple types of stimuli.

Thermal Grill and Pain Circuit Analysis

The simplest procedure in the test battery is to sit with "eyes open" or "eyes closed" to collect EEG data and form a baseline PSD. After being put through a fundamental or baseline assessment, the test battery is begun where a subject experiences a flash of light at the spectrum of frequencies of interest while wearing special goggles. The test battery can stimulate visually either eye alone or both together, with phase difference controlled as needed. The same stimulation paradigm can occur using sound, where one delivers auditory tones through headphones on the subject. Finally, one can use a thermal grill to deliver spatially alternating hot and cold information. The thermal grill is an array of alternating metal or glass bars, with the hot bars fixed at 40 deg C. and the colder bars fixed at 20 deg C. The grill is an alternating 40/20/40/20/40 deg C. array of bars about the size of a hardcover book upon which one places one's hand. Each bar width is typically 5 mm within the thermal grill, but larger and smaller sizes are also acceptable. With the thermal grill, one can compare right hand vs. left hand. Alternatively, one can place a cold or hot temperature in one hand and look for changes in the EEG signatures as a function of temperature-induced pain states. This was successfully demonstrated in FIG. 27B with an ice cube squeezed in the hand for 60 seconds compared to a room temperature computer mouse as control FIG. 27 A. The pain associated with the extreme cold of the ice cube significantly diminished the alpha rhythm typically observed in a resting Eyes Closed state.

Alternate embodiments of the present invention include all other means to make cold and warm temperatures, including without limitation, cool air, ethanol evaporation, peltier element with driving current, dimethyl ether and propane in a pressurized can.

FIG. 27B presents data collected from the analysis of pain in the hand from an ice cube for 60 seconds as a surrogate marker for a thermal grill of alternating temperatures in an interwoven fashion. One can see the prominent alpha peak 580 at 10 Hz in the upper trace FIG. 27A with Eyes Closed while holding a room temperature mini-computer mouse versus the significantly diminished peak 590 in the "ice cube in the left hand" trace, as shown in FIG. 27B. Notice as well the shift in low frequency delta from the norm 600 to the prominent 610 power in relative delta.

Figure 28:
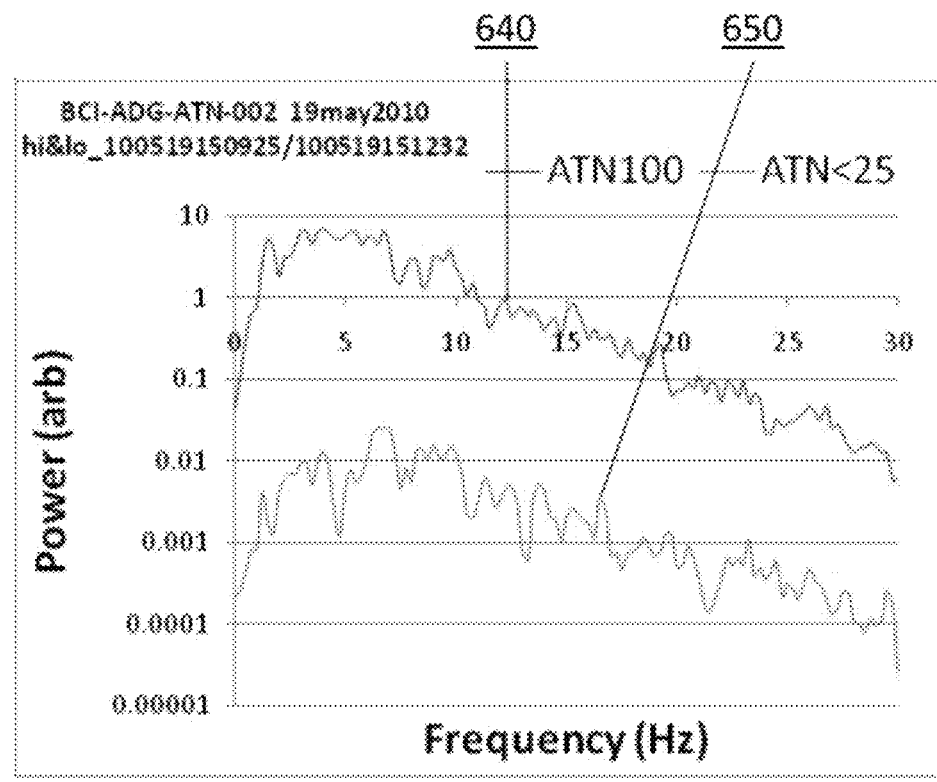
FIG. 28 is a graph showing averaged relative PSD during either (i) attentive or (ii) inattentive states.

FIG. 28 compares the averaged relative spectral power of a 48 year old male achieved while focusing his attention with his Eyes Open versus while working hard to remain in as inattentive a state as possible with Eyes Open. Notice the dramatically different overall power and other features different between the two states of attention, as evidenced by the time averaged relative PSD.

Pharmaceutical Compound Evaluation and Monitoring

The systems and methods of the present invention are very well suited to the evaluation and assessment of medical therapies, including drug therapy candidates and investigational compounds and agents. Using a test battery of three or more sensory and cognitive challenges, one could assess in a short 15-20 battery multiple sets of circuits to arrive at a broader assessment of compound effect centrally. For instance, as a non-limiting example, a pharmaceutical company could choose to run a battery of sensory and challenge tasks before a compound is administered to subjects in a phase 1 or phase 2 clinical trial. Then, during exposure to varying doses of a drug vs. placebo, the EEG-based battery of sensory and cognitive tasks could again be applied to delineate a pharmacodynamic effect of a drug. This information could be obtained in normal volunteers during early phase drug studies to facilitate internal decision making about a drug's dose-responsive effect on the brain. Alternatively, the same approach can be used in later stage clinical studies within patient populations, wherein a similar approach could not only demonstrate pharmacodynamic responses unique to individual patients or to patient populations, but could also demonstrate a correction of diseased brain function for proof of concept studies. Moreover, the convenience, portability, and remote monitoring allowed for by the present invention, lends the described approach to be included in phase 3 registration studies to continue monitoring of signals observed in earlier phase studies. As described previously, the described systems and methods of the invention also allow for post-marketing titration and optimization of drug therapy as well as the tracking of safety signals.

As a non-limiting example of the systems and methods of the present invention working with known brain and nervous system compounds, FIG. 29A presents the averaged relative PSD from a 48 year old male during an Eyes Open task immediately before taking a 0.5 mg dose of Klonopin (Clonazepam) compared to his averaged relative PSD 80 minutes after the dose shown in FIG. 29B. One can observed enhanced spectral beta post pill 680 compared to pre pill 670. The emergence of an alpha wave peak 690 is observed as well. A statistically significant elevation in the relative beta ($p<0.019$) and the 10 second sliding window absolute beta ($p<0.021$) was observed 80 minutes post the 0.5 mg Klonopin dose.

Figure 30A:
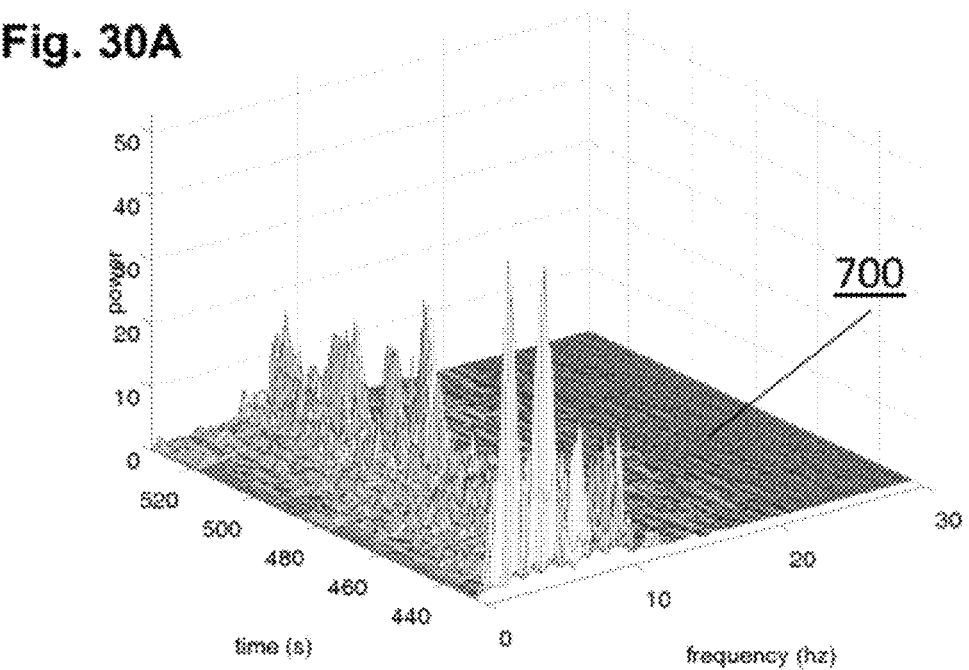
FIG. 30A is a 3-D graph of an Eyes Closed absolute power spectral density sliding window plot before taking a 25 mg dose of Histamine receptor H1 receptor antagonist Benadryl.
Figure 30B:
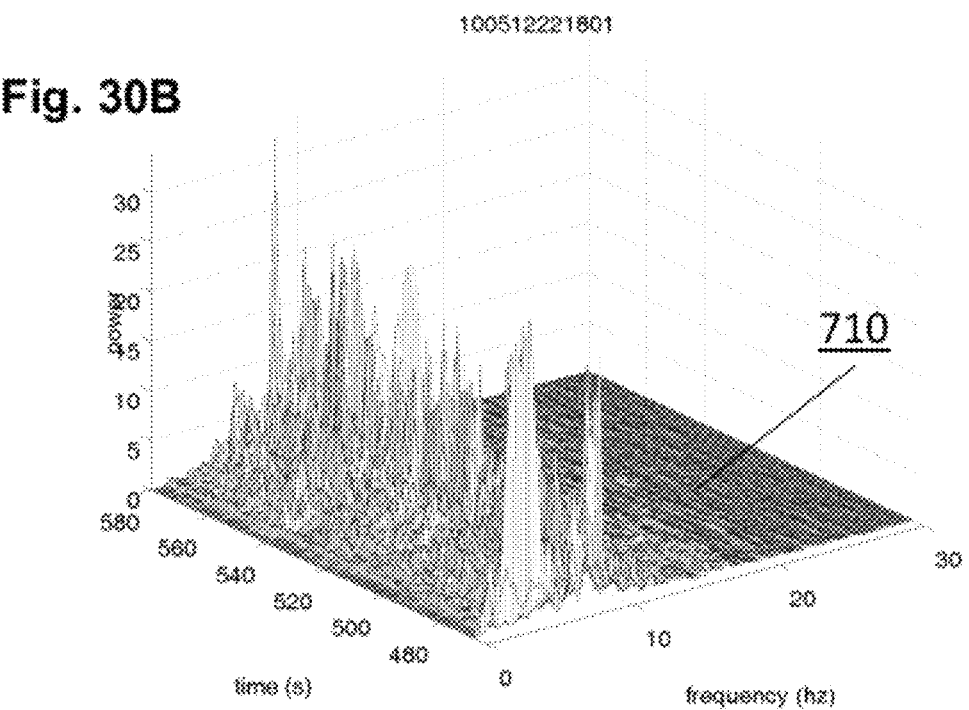
FIG. 30B is a 3-D graph of Eyes Closed absolute power spectral density 60 minutes after taking a 25 mg dose of Histamine receptor H1 receptor antagonist Benadryl.

As a second non-limiting example of the systems and methods of the present invention successfully working, FIG. 30 presents the comparison between 10 second sliding window averaged absolute PSD from a 48 year old male during a resting Eyes Open task immediately before taking a 25 mg dose of Benadryl (Diphenhydramine hydrochloride) in FIG. 30A compared to his similarly calculated PSD 65 minutes after the dose. Pre pill there is little absolute beta 700 versus 65 minutes post pill, one observes significantly more spectral beta 710 ($p=0.029$). This comparison again shows a difference observable by central nervous system acting pharmaceutical agents.

Analysis of Sleep and States of Alertness

Figure 31:
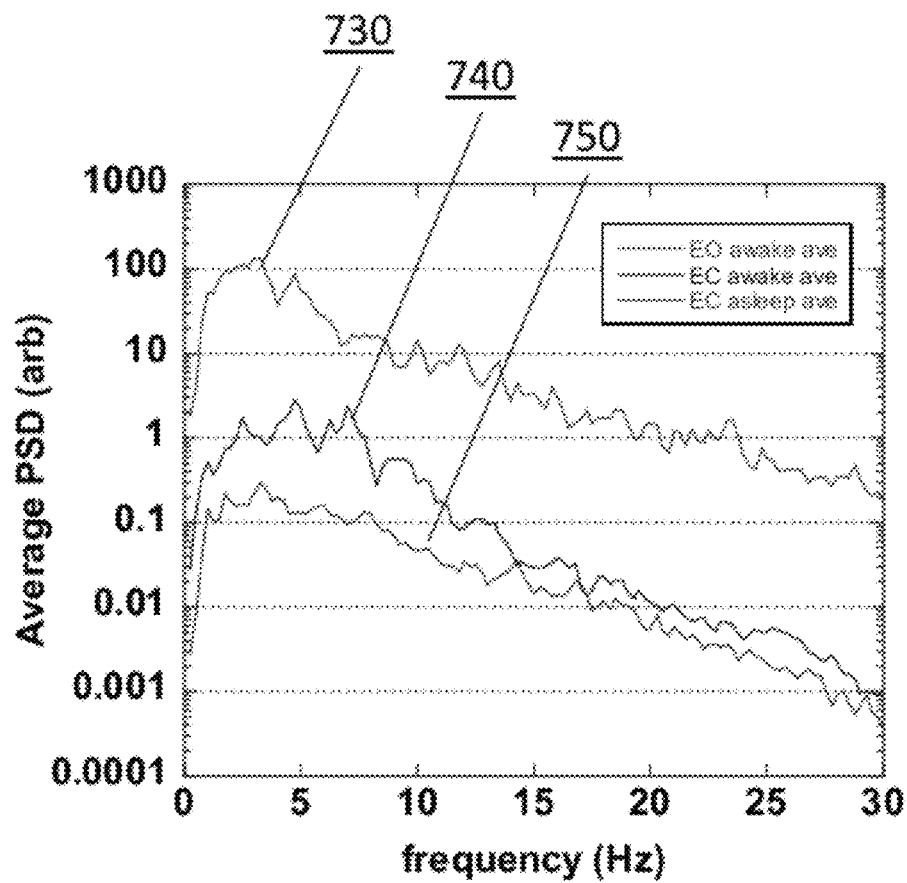
FIG. 31 is a graph showing calculated PSD during the following alertness states: Eyes Open awake, Eyes Closed awake, Eyes Closed asleep.

FIG. 31 presents the different averaged relative PSD from a 48 year old male during various states of sleep videotaped at home while recording his EEG. In the first state, the subject is Eyes Open and awake 730; in the second, the subject has Eyes Closed (EC) but remains awake 740 as evidenced by his finger motion indicative of his counting on his fingers. Thirdly, the subject is fully asleep with EC 750, as snoring was recorded and an involuntary sleep twitch observed on the recorded video tape. Not only are the relative power observed in the averaged relative PSDs clearly different, there is debate and disagreement between regarding the various structures within the PSD. Nonetheless, the systems and methods of the present invention have shown the ability to distinguish different states of alertness through the acquisition of state based PSD.

Novel Headsets to Present Sensory and Cognitive Challenges Simultaneously with the Ability to Record EEG Signals and Data The systems and methods of the present invention also include electronic devices which comprise electronic systems for the presentation of sensory and cognitive challenges. In addition, the same device headset has the functionality to record from at least one EEG sensor relative to ground sensor. The ground and reference sensors or electrodes are typically located behind the ear whenever possible.

Figure 32:
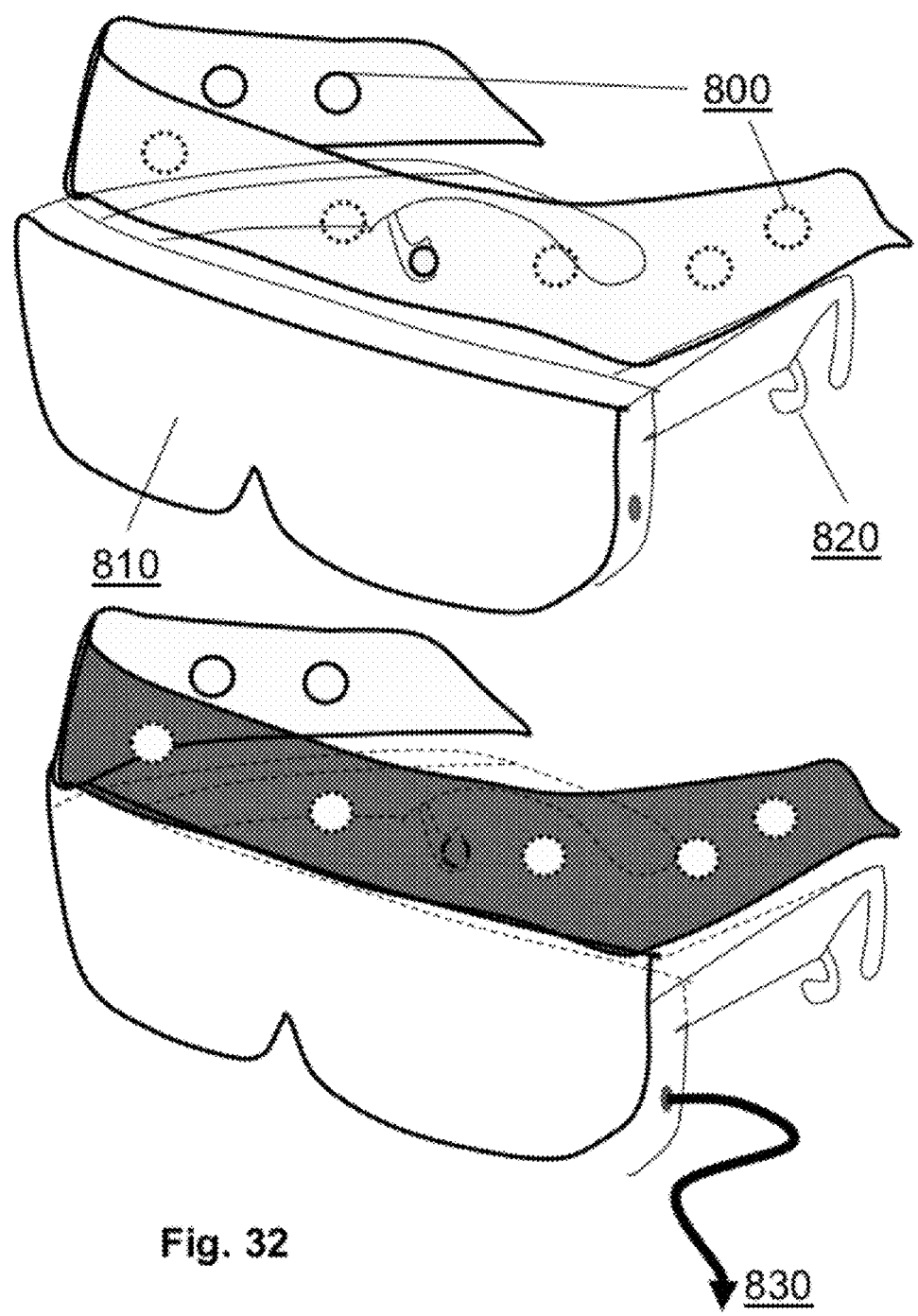
FIG. 32 illustrates a novel headset that integrates the capability to both stimulate the subject with audio and visual stimulation as well as record EEG with sensors and electrodes.

FIG. 32 illustrates an embodiment of a novel headset that combines elements of stimulation including audio ear buds 820, virtual reality screen or LED for photic or visual stimulation 810, with integrated EEG sensor(s) 800 to record EEG signals including both Ground (GND) and Reference (Rrf) electrodes, with signals transferred through either wireless or wired 830 means.

Data Acquisition, Signal Analysis, and Classifier Identification

Finally, the systems and methods of the present invention include post data acquisition and signal analysis, presentation, and interpretation. The classic methods of evaluating power in specific bands (alpha, beta, etc.) or processing via FFT for a power spectrum are well known in the art. Since there is data to support the fact that each person's power spectral density is reproducible and unique to them, one could imagine using this biometric fingerprint or signature of the individual to monitor each person individually, with increased sensitivity and specificity. Since there is a well-known power reduction of approximately 1/f(Hz), the power spectrum is typically shown on a log plot to enable observation of the higher frequency components (beyond 15 Hz typically).

Standard spectral analysis is clearly a part of the rich data tables available after artifact detection and raw signal processing. Moreover, in addition to non-limiting alpha and beta bands, one can look at the raw signal using non-linear dynamics and determinate computationally the Lyapanov exponent, fractal dimension, and other nonlinear properties of the time series. These additional variables can be used to create additional biometric properties of each data block as additional variables to be added to the summary data table for each experiment. Moreover, wavelet analysis where the range of temporal wavelength used in the transformation process is varied. Gabor analysis is another possibility. The whole aim is to take as many analytic approaches as possible to generate as rich a summary data table as possible. Subjects and tasks would be entered as individual rows, then each variable would be entered as a column in the summary data table.

After inclusion of sensory stimuli and cognitive data in the data table, perhaps with the addition of the temperature and other sensor data, statistical analysis can take place. Standard uni-variate analysis can take place on each variable under the present invention. More interesting however is the notion of using the various techniques of multi-variate analysis to combine variables to find the best classifier or discriminant function. Linear discriminant analysis in its various incarnations is a part of the present invention on summary data tables generated from sensory and cognitive challenge data. So are tree based methods like Random Forest or shrunken centroids.

Another aspect of the present invention is the quantitative analysis of the eye blink within the EEG traces. It has long been reported that eye blink is an artifact. An alternate perspective is that identification and quantization of the eye blink rate is another opportunity to create analysis routines that identify eye blinks and note their timestamp within a time series. From this data, one can note their time within an elapsed time challenge or task. Eye blinks can be correlated with other time series information available to provide clues as to why someone eye blinks. They can be used as a biometric or variable for classification of disease states, brain injury, aging etc., in both univariate and potentially multi-variate classifiers.

An important element of the present invention is the creation of unique summary data tables from the multiple tasks that are conducted in a test battery. In particular, if a subject undergoes 9 tasks of 2 minutes duration each in a test battery, then there are really 17 different periods of time that can be analyzed. There are the nine 2 minute blocks of each of the individual tasks. These can be averaged in a time averaged fashion over the course of the full two minutes or they can analyzed with a sliding window of five to 30 seconds duration, preferably five to 20, and most preferably 5 to 10 seconds, although a sensitivity analysis which shows results equivalent to times in these windows are also considered part of the present invention. But there are also the 8 transition periods where the subject moves from one task to the next. It is part of the systems and methods of the present invention that these transient state changes can be analyzed for temporal changes transiently. For instance, it may be that Alzheimer's subjects have a difficult time moving from a card flip task to a light flashing task, that is their brain does not synchronize with the flashing light until 15 or 20 seconds into the photic stimulation task. In this case, measuring the time of onset of brainwave entrainment to the stimulus frequency F relative to the beginning of the task could be an excellent variable to measure as a subject switches from task to task. Thus, the transition zones of data, those which exist between each pair of tasks, represent additional blocks of raw data to analyze for transient variables like the one identified above. It could be that the order of tasks could affect the variables which are measured. In this fashion, a task A followed by B could yield different information than task B followed by A, especially in the transition zones.

Recapitulation

The invention concerns systems and methods for monitoring brain health by creating a personalized physiological brain health bio-signature that will allow monitoring of disease onset and progression, drug therapy, and biofeedback. The approach relies upon the use of portable EEG technology to acquire quantitative EEG data during several physiological states, which collectively represent a unique set of signature data regarding a given individual's nervous system health. The states during which EEG recordings are taken are chosen to allow assessment of many brain circuits. These states include resting awake, drowsy and sleep states with minimal external stimuli (eyes closed, quiet, unstressed). Power spectral analysis of EEG traces recorded during these states show excellent test-retest reliability (FIG. 10).

Maneuvers such as opening of the eyes induce a different brain state that can be reliably measured using even a single EEG lead placed over the forehead (FIGS. 11, 12, 13). Scalp EEG electrodes typically pick up the activity of only approximately one cm² of cerebral cortex lying directly beneath the electrode, scalp and skull. Thus, while the classical change in EEG response to eyes opening and closing is well known over the occipital scalp (which overlies the visual cortex), the systems and methods of the present invention to measure this response over the forehead scalp (which overlies the frontal cortex) suggest that the present invention assesses the integrity of many widespread anatomical brain tracts and circuits. In the frontal response to eyes opening and closing, shown in FIG. 11, the neuronal structures assessed would include the retina, optic nerves, thalamus, optic tracts and visual cortex, as well as brain tracts that connect the visual cortex and thalamus to the frontal cortex. By establishing a reliable baseline for such a response in a given healthy individual, the present invention should allow detection of alterations in the health and function of these brain structures and circuits in conditions including but not limited to normal aging, blindness, stroke, trauma, demyelinating disease, infection, inflammation, neoplasm or intoxication. The enhanced alpha rhythm band (10 Hz) promoted by eyes closing is believed to represent a "readiness state" of the brain mediated by brainstem arousal centers, thalamus, and cortex (Paiva and Paiva, 2007). Although the exact frequencies and magnitude of alpha rhythm change produced by eyes opening and closing may vary between individuals, by establishing a baseline for a given individual, this response can serve as a personalized check of the neuroanatomical physiology described above. Unlike evoked scalp potentials, which have previously also attempted to investigate the health of specific circuits, the present invention leverages the induction of a state sustained over several minutes, which alters the frequency domain of the scalp EEG rather than the temporal stimulus-locked EEG change seen with evoked potentials. Using retinal input of flashing light at specific frequencies (FIGS. 25 & 26) we also show that, using a single EEG lead over the forehead, such a flashing photic input state can demonstrate entrainment of brain circuits at the driving photic frequency as well as displaying additional EEG harmonics of the input frequency, evidence of non-linear interactions within the nervous system. This ability to entrain brain circuits serves as another functional check of multiple brain pathways, which is not possible with simple evoked electrical responses and which would be expected to be highly sensitive to the pathologies and perturbations included in the description above.

Similar sensory input approaches can also be taken for other categories of sensory information such as sound, smell, taste, touch, and balance. As such, a broad and comprehensive neuroanatomical assessment of nervous system health can be carried out using the systems and methods of the present invention. Moreover, the brain response to each sensory modality can be fine-tuned by examining the effects of a wider perceptual array of inputs such as different spectral colors, unique odorants and tastes, and different sound frequencies. As a non-limiting example, consider touch sensation, where several different modalities, such as temperature, sharp sensation, dull sensation, and vibration at different frequencies, can be evaluated.

These inputs can also be selectively applied to either of the two eyes, ears, nostrils, and various parts of the tongue and skin. Such assessments further expand the ability of the present invention to monitor nervous system symmetry or aberrations thereof.

An illustrative example of how such a systems and methods can be utilized is demonstrated in FIG. 27A and FIG. 27B using a temperature stimulus to the left hand. In this example, we show that holding an ice cube in the left hand significantly attenuates the alpha enhancement response to eyes closing. This may result from a change in thalamo-cortical interaction to replace the brain readiness state typically attributed to the enhanced alpha rhythm with a state reflecting awareness of the ice cube temperature sensation in one hand. Such a response measured with the present invention can thus confirm the intactness of specific neuroanatomical connections between the right hand and the brain (peripheral nerve, spinal cord, brainstem, thalamus, limbic system and cerebral cortex). By applying the same approach to the right hand, or right and left legs, one can use the attenuation of the alpha signal to confirm the intactness of several neurological pathways and structures.

A much wider array of neuroanatomical circuits can also be assessed by varying the delivery of sensory input so as to create sensory illusions. Illusions are distortions of sensory perception that can reveal how the brain normally organizes and interprets sensory stimulation. While illusions distort reality, they are generally shared by most people, as they reflect the function of brain circuits common to our species. One such illusion is constituted by auditory binaural beats. In this illusion, when sound tones presented to both ears are varied by a difference of a specific pitch frequency (i.e. a sound tone of 400 Hz in one ear and a tone of 415 Hz in the other ear to yield a differential of 15 Hz), the illusion of a rhythmic beating sound at the differential frequency is perceived (i.e. 15 Hz). [G. Oster (1973) Auditory beats in the brain. Scientific American, v229, p 94-102]. This illusion is also reported to be accompanied by the entrainment of scalp EEG at the differential frequency which reflects involvement of a much broader set of brain structures (including the brainstem inferior olivary nucleus) than just those involved in sound perception (Cai H, Carney L H, Colburn H S. 1998. A model for binaural response properties of inferior colliculus neurons. I. A model with interaural time difference-sensitive excitatory and inhibitory inputs. J Acoust Soc Am. 1998 January; 1 03(1):475-93.).

Another such sensory illusion is known as Thunberg's thermal grill (Craig A D, Bushnell M C. The thermal grill illusion: unmasking the burn of cold pain. Science. 1994 Jul. 8; 265(5169):252-5) which present juxtaposed metal cylindrical bars (2-15 bars) of cool (20QC), warm (40° C.), or alternating cool and warm temperatures (Craig and Bushnell, 1994). Only when the warm and cool bars are alternated sequentially, a subject placing a hand on such a grill setup will experience the illusion of pain rather than warmth or coolness. This alternating warm-cool touch maneuver has been shown to activate pain circuits in the brain by functional magnetic resonance imaging (Craig A D, Reiman E M, Evans A, Bushnell M C. Functional imaging of an illusion of pain. Nature. 1996 Nov. 21; 384(6606):258-60.) and should induce a unique functional EEG differentiable brain state vs. the warm or cool stimulus alone. Again, unlike simple sensory input, objective responses to such a pain illusion can assess the health of a set of brain regions (i.e. limbic system) that is much wider than just the temperature sensing pathways.

Distinct brain circuits and structures are also known to underlie cognitive processes. Historically, the reliable testing of individual human cognition in health and disease has been a challenge. This is remarkable given the central role of cognition as a measure of brain health. Crude population-based normative indices such as intelligent quotients (IQ) are still used today to define levels of cognitive performance. Such outdated and imprecise "brain numbers" need to be replaced with more objective and neurophysiology-based measures in order to improve health management. Computerized cognitive tests for unique cognitive domains have made important advancements in this regard. By developing unique standardized tests for attention, working memory, memory entrainment and retrieval, visuospatial function, and executive function, computerized test batteries such as the CogState cognition battery can quantitatively interrogate specific neurological circuits and brain structures. Such tests have been widely used in tracking disease and treatment responses. However, the concept of cognitive domains being mediated by selective circuits would be greatly enhanced by simultaneous assessment of brain neurophysiology during the cognitive tasks. Since performance on cognitive tests is dependent on individual effort and cooperation, adding an objective passive measurement such as functional qEEG to such tests can also help qualify the performance of such cognitive tests in subjects and patients who may not be cooperating or are unable to give sufficient effort. At the least, relating cognitive performance to the objective health of brain circuits could lead to the development of new classifiers or discriminant functions to serve as better biomarkers of brain health.

The systems and methods of the present invention lend themselves to the development of such classifiers by allowing convenient quantitative EEG measurements that can be related to performance on cognitive domain-specific tasks done alongside or simultaneously with the EEG measurements. The ability to create mixed modality biometric signatures including both cognitive variables with EEG variables will significantly enhance the clinical utility and accuracy of the computer cognition tests. An example of this application is shown in FIGS. 16, 17, 18, 19, and 20, using the CogState "Identification" task (which asks the test subject "Is it Red?" when a new playing card flips) which assess the Attention cognitive sub-domain. As FIG. 16 illustrates conceptually and FIG. 20 shows an embodiment of a mixed modality computer cognitive task plus functional EEG data table from which mixed modality signatures and classifiers can be derived.

The systems and methods of the present invention are not limited to the CogState Identification task or research battery. Any other clinically validated cognitive tests that measure several cognitive functions simultaneously can also be included within the present invention, preferentially in a computerized format but not necessarily. The Paced Auditory Serial Addition Task (PASAT) is a serial-addition task used to assess rate of information processing, sustained attention, and working memory (Tombaugh T N. A comprehensive review of the Paced Auditory Serial Addition Test (PASAT). Arch Clin Neuropsychol. 2006 January; 21 (1):53-76.). In addition, since this task requires the comprehension and utterance of numbers, it also tests language function. Again, the addition of functional EEG measurements during the PASAT test or a correlation of performance on the PASAT test to the personalized neurophysiological biometric signature determined through the present invention can create new classifiers for tracking brain health and treatment response. FIG. 21 shows averaged relative power PSD during the PASAT task compared to a resting Eyes Open state. FIG. 23 shows the present system of PASAT scoring which relies only on the total number of correct answers provided and ignores the rich temporal information contained in the reaction times. FIG. 24 shows the system and method of the present invention whereby auditory signals collected by a microphone can be digitized and analyzed for reaction time and speech to text conversion for automated scoring. Most importantly, they can be combined with the functional EEG data and metrics to provide more sensitive and specific classifiers and signatures.

The ability of the systems and methods of the present invention to investigate the health of brain circuits mediating sensory experience and cognition can also be expanded to the assessment of behavioral disorders such as anxiety, panic disorder, depression, bipolar illness and post-traumatic stress disorder. Subjects suffering from these disorders are known to respond and react to certain sensory stimuli differently than normal subjects. For example, visual stimuli depicting pictures of threatening or depressing stimuli are known to elicit differential emotional responses from patients with anxiety and depressive disorders versus normal healthy subjects (see for example Bishop S J. Neurocognitive mechanisms of anxiety: an integrative account. Trends Cogn Sci. 2007 July; 11 (7):307-16.).

The systems and methods of the present invention of brain health assessment can be utilized to either identify unique EEG signatures observed during such emotional responses to visual scenes or can utilize multi-modal combinations of the personalized EEG biometric signatures with performance on the respective emotional visual analog scales to create new classifiers of brain function.

The systems and methods of the present invention can be similarly applied to other forms of challenge stimuli such as auditory, olfactory, gustatory, and tactile stimuli. Specific examples of how challenge tests can be combined with the functional EEG measurement systems and methods described herein to help diagnose disease can be found in the lactate infusion and carbon dioxide ($CO_2$) inhalation tests. These tests are best known for their proclivity for inducing states of hyper-arousal such as panic and anxiety attacks in subjects prone to anxiety and panic disorders (Keck M E, Strahle A. Challenge studies in anxiety disorders. Handb Exp Pharmacal. 2005; (169):449-68.). Although the best known readouts for these challenge tests are behavioral scores, these tests also have physiological readouts, which show differential responses in normal healthy subjects vs. disease populations. For example, hyperventilation in response to hypercapnia ($CO_2$ challenge) is accentuated in subjects with anxiety, phobia, and panic disorders, while it is diminished in patients with depression (Keck and Strahle, 2005; Monkul E S, Onur E, Tural U, Hatch J P, Alkln T, Yucel B, Fidaner H. History of suffocation, state-trait anxiety, and anxiety sensitivity in predicting 35% carbon dioxide-induced panic. Psychiatry Res. 2010 May 16. EEG performed during the $CO_2$ challenge is also known to change in normal subjects (Burykh E A. Interaction of hypocapnia, hypoxia, brain blood flow, and brain electrical activity in voluntary hyperventilation in humans. Neurosci Behav Physiol. 2008 September; 38(7):647-59.) and would be expected to show differential features in behavioral disorders (Lopes F L, Oliveira M M, Freire R C, Caldirola D, Perna G, Bellodi L, Valenga A M, Nascimento I, Piedade R A, Ribeiro P, Zin W A, Nardi A E. Carbon dioxide-induced panic attacks and quantitative electroencephalogram in panic disorder patients. World J Bio Psychiatry. 2010 March; 11 (2 Pt 2):357-63.). Thus, by combining the emotional scale, ventilatory, and EEG responses to a brief $CO_2$ challenge, the systems and methods of the present invention can provide novel, and potentially more sensitive classifiers for diagnosing behavioral and neurological disorders.

Provocative challenge tests in normal subjects, such as the ones described above, have also long been performed with pharmacological agents to model cognitive disease processes. Drugs such as scopolamine, clonazepam, or Benadryl™ can be used to manipulate specific neurochemical pathways such as the cholinergic, GABAergic and histaminergic neurotransmission systems, respectively. Since changes in these and other neurotransmitter systems are known to underlie the cognitive dysfunction observed in many neurological diseases, a demonstration of the ability to monitor the effect of such specific pharmacological provocative challenges using the present invention would support the notion that this approach could also track disorders, which manifest via changes in these neurotransmitter systems. FIGS. 29 and 30 show prominent changes in the resting EEG power spectra detected by the present invention after administration of clonazepam and Benadryl™. These sedative agents are well known to impair cognitive performance, and a combination of the cognitive performance on computerized cognition tests under the influence of these agents, along with the EEG response could lead to a new classifier of brain health. Such a classifier can be of utility in tracking drug responses during clinical drug trials as well as in tracking the early onset and progression of dementia disorders. Moreover, they could be useful to monitor patients already using pharmaceutical and other therapies.

As a non-limiting illustrative example, among the major impediments to the design of clinical trials for the prevention of Alzheimer's disease, the most critical is the lack of validated biomarkers, assessment tools, and algorithms that would facilitate identification of asymptomatic individuals with elevated risk who might be recruited as study volunteers. By establishing a baseline personalized biometric signature of brain health, our approach can detect subtle changes in an individual's brain function due to the compromise of specific neuronal circuits and neurotransmitter systems, thus identifying prodromal subjects more sensitively and specifically for potential enrollment in clinical treatment trials or for lifestyle modification approaches.

Such personalized monitoring may be specifically valuable for individuals with known disease susceptibilities such as those expressing the APOE4 genotype or those known to have familial predilection for Alzheimer's disease or Huntington's disease. This approach can also apply to those with familial Parkinson's disease or those working in occupations which carry risk for developing Parkinson's disease or neuropathies (neurotoxin exposure). Occupations at risk for developing hearing disorders due to loud noise exposure or concussion (e.g. military service and contact sports professions) would also benefit from establishing personalized brain biometric signature baselines using the systems and methods of the present invention for longitudinal personalized tracking over time. In this way, the present invention can serve as a broadly applicable new generation of brain biomarkers much the way that blood pressure and cholesterol level monitoring serve in aiding early detection of cardiovascular and metabolic disease. The data shown in FIGS. 29 and 30 supports construct validity of the present invention by demonstrating expected differences in EEG by perturbation of specific neurochemical systems (Fink M. Remembering the lost neuroscience of pharmaco-EEG. Acta Psychiatr Scand. 2010 March; 121 (3): 161-73.).

Many neurological diseases are insidious and once diagnosed can progress at unpredictable rates with differential response to therapies. By allowing assessment of a wide variety of neurological circuits, the present invention can be customized to track progression and treatment response of a wide variety of disorders to include peripheral nervous system disorders such as neuropathies, retinal dysfunction, hearing disorders as well as many central nervous system disorders, which include but are not limited to multiple sclerosis, myelopathies, cranial nerve disorders, spinal cord and brain trauma, stroke, epilepsy, dementia, and schizophrenia.

Moreover, by allowing convenient remote monitoring using the present invention, the tracking of and treatment adjustment for such disorders can be undertaken much less expensively than the present status.

EXAMPLES

While the above description contains many specifics, these specifics should not be construed as limitations on the scope of the invention, but merely as exemplifications of the disclosed embodiments. Those skilled in the art will envision many other possible variations that are within the scope of the invention. The following examples will be helpful to enable one skilled in the art to make, use, and practice the present invention.

Implementation Details
1. Standard Hardware and Software for EEG

Standard EEG equipment (FIG. 2 42) can be used such as hardware by Compumedics Neuroscan (http://www.com.Qumedics.com/) or VIASYS Healthcare's Nicolet (http://www.viasyshealthcare.com/). In particular there are favorable single electrode EEG headsets by NeuroSky (http://www.neurosky.com/) such as the MindSet Pro. Amplifiers such as Compumedics Siesta or NuAmps (http://www.compumedics.com %) can be used (FIG. 4 85). Software such as EEGLab (http://sccn.ucsd.edu/eeglab/) can be used from within a MATLAB environment (httg://www.mathworks.com) or Compumedics Neuroscan SCAN 4.5.

Implementation Details
2. Means to Record and Digitally Transmit Signals

Standard hardware can be employed to record scalp electrode EEG signals. Typical instrumentation amplifiers like a Burr-Brown INA326 or INA333 (http://www.burrbrown.com/), or alternatively Analog Devices AD8220 (http://www.analog.com/en/index.html) can be configured as shown in FIG. 4 or 61 FIG. 3. Typically, a scalp electrode potential is referenced to a reference electrode on the ear or other non-brain coupled location. Often, a third electrode is used to subtract a DC bias from the potential measured on the scalp in order to force the EEG signal to be AC-coupled rather DC-coupled to the amplifier. The analog output from the instrument amplifiers can be filtered using standard low-pass, high-pass and band-pass filters to select frequencies of interest and remove interference from the 60 Hz line frequency (e.g. via a notch filter) 62. The output of the filter can be passed through an analog-to-digital converter (ADC) 63 which feeds a digital signal processor (DSP) 64 as offered by Analog Devices and Burr-Brown, among others. The DSP output can be streamed into a wired or wireless transmitter 65 (e.g. Bluetooth™ device) or other network interface device for transmission via any one of the means shown, but not limited, to those in FIG. 5. The transmitted data can be received by a matched wired or wireless receiver 70 or other network interface receiving device (e.g. iPhone™ or BlackBerry™, FIGS. 7A, 7B) and stored on a mass storage device such as a hard disk drive or flash memory module 71. The data can then be analyzed in a central processing unit (CPU) with predefined analytical algorithms 72 which create an index or multi-variate output 73 for visual display 74 and interpretation. The data can be further transmitted via broadband network 80 like cellular telecom or the Internet to remote servers 81 for database creation and storage. Group and meta analysis 82 can be done remotely in batch 83 and individual modes for enhanced group and personalized medicine results 84.

Implementation Details
3. Novel EEG Form Factors to Collect EEG Signals and Common Means to Display the Data One can imagine incorporation of dry scalp electrodes into several form factors different from those previously embodied. One can incorporate the EEG electrodes and signal electronics into a baseball cap, beach hat, military helmet, or other equivalent form factor to conceal the electrodes while in contact with the scalp and provide space, typically although not required, at the top of the form factor for the signal electronics including wireless transmission interface like Bluetooth™ among other non-limiting examples. Headband 86 of FIG. 6 can hold electrodes 92 to scalp 94, providing wired signals along support 88 to electronics module 90. In addition to a computer, a PDA or data enabled smartphone (see FIG. 7), could be held in the user's hand and preloaded with software designed to receive the transmitting device data stream and compute pre-loaded algorithms on the data. The data could be visually presented both before and after post processing on the device before being relayed to a central server or database via cellular telecomm network. Given a proper visual display like the NeuroSky "Meditation" scale, this could enable someone to relax on a routine basis while walking around with a novel EEG form factor and handheld device like an iPhone.

Example 1

BCI Signatures with Neurosky™ Mind Pro Headset with Neuroview™ Software

Using a NeuroSky™ MindSet™ Pro headset with NeuroView v2.4.2 software, we recorded bio-electrical EEG signals from the subject's forehead, located mid-way up the forehead above his left eye at International 10-20 Standard position Fp1. As shown in FIG. 8, the raw signal was streamed to the laptop PC computer via a Bluetooth™ dongle provided by NeuroSky with the MindSet Pro™ headset. Configuration was done according to NeuroSky instructions on a Compaq™ EvoN620c laptop PC running Microsoft Windows XP™ SP3. Through the serial Comm8 port of the PC, the headset was paired and data streamed in the NeuroView software after the command set "0x11" was sent to the headset, which turned on the raw data stream to the PC. In the upper left panel of the image 100, one can see the collected raw signal from the device after the subject blinked his eyes twice in succession 101 and 102, demonstrating the large "artifact" creation effect that eye blinking has on a forehead-recorded EEG signal. The ground electrode relative to the forehead electrode was built into the left ear cup of the headset using a conductive fabric. A third electrode, also placed into the fabric of the left ear cup, was used to establish the DC electrode offset potential of the individual during recording, and permitted the creation of a pure AC signal for pre-amplification, signal condition, conversion, and transmission. In the upper right panel of FIG. 8 at 105, one can see the filtered EEG signal recorded after the DSP employed proprietary NeuroSky filtering algorithms to reduce eye blinks to 101 and 102 to small blips 106 and 107. Finally, in the FIG. 8 lower center panel 110, one can see the power spectral density of frequencies that made up the components of the EEG signal after spectral decomposition via Fast Fourier Transform (FFT) was performed in the DSP of the headset and displayed in the NeuroView software.

Example 2

Raw Signals and Computation of Power Spectral Densities

FIG. 9A shows a 30-second epoch of data collected at 128 samples per second with 12-bit dynamic range, reflecting over 23,000 data points of EEG. Five additional epochs of 30 seconds each were accumulated to create a 3-minute raw EEG trace from which the Fast Fourier Transform was performed into the frequency domain and the Power Spectral Density (PSD) plotted as a function of frequency from zero to 30 Hz. FIG. 9B shows a resting Eyes Closed (EC) PSD collected on a 44 year old male participant. One can see a clear alpha rhythm peak at 115.

Example 3

Analysis of Interday Variability and Eyes Closed (EC) to Eyes Open (EO) Ratios within Subjects FIG. 10 shows an analysis of the variability of the PSD for a 44 year old male over the course of five (5) independent days. Data was recorded from the same clinical protocol on each of five (5) days at approximately 9 am each morning. The subject sat in a quiet room with lights dimmed with eyes closed for three minutes, then opened his eyes for three minutes while recording the eyes open EEG test, and then repeated the process two more times for a total of 18 minutes of recorded EEG data. The resting Eyes Open relative PSD traces were computed from the raw EEG signals and plotted on the same graph (FIG. 10). The geometric mean of the five traces is shown as the bold black line in FIG. 10A. The computed coefficients of variation (CV) for each of the delta, theta, alpha and beta bands are shown in the inset towards the bottom of FIG. 10A, all showing % CV less than or equal to 25. The absolute PSD traces on each of the five days show greater variability, as shown in FIG. 10B. Finally, ratios of band power like the theta/alpha ratio were calculated, as shown in FIG. 10C for the five different days. The theta/alpha ratio was quite stable with interday CV of just less than 9%. The mean is shown horizontally by 130 with a single standard deviation above and below indicated by 133 and 136 respectively.

In FIG. 11, one can see the acquired Eyes Closed (EC) 140 and Eyes Open (EO) 130 PSD traces on the same graph. Taking a bitwise ratio of the EC divided by the EO trace for each frequency bin in the PSD, one can see in FIG. 12A the EC/EO ratio of data similar to that shown in FIG. 11. The same data acquisition protocol was conducted on a 48 year old male participant, and his EC/EO ratio is presented in FIG. 12B, again showing excellent alpha rhythm elevation with eyes closed 170 but with a different structure to this subject's alpha peak.

Finally, the clinical data acquisition protocol was amended to include the collection of data remotely through an Internet web meeting connection (Adobe ConnectNow™ was used but Web Ex™ or GoToMeeting™ Internet protocols could equivalently be employed). A third male, also 48 years old, was seated in Manhattan in New York City with an EEG headset on, while the data collection specialist sat in his office near Philadelphia, Pa. Through a remote Internet connection and simultaneous telephone call, the data collection specialist was able to remotely collect data, controlling the local PC in Manhattan and guide the participant through the data collection paradigm. In FIG. 13, one can see the elevated alpha peak 175 around 10 Hz for this participant in his EC/EO PSD ratio. Again, the exact structure of the PSD appears to be an excellent biometric signature for each individual.

Example 4

Multi-Task Sensory Stimulation and Cognitive Challenge Data Collection Paradigms The clinical protocol of example 6 above was simplified to include only resting Eyes Closed versus resting Eyes Open tasks and EEG recordings. However, according to the systems and methods of the present invention, much more dynamic and rich clinical protocols can be achieved. For instance, FIG. 14 illustrates an auditory stimulation data acquisition paradigm in which a number of three or more tasks are conducted in a prescribed sequence to collect auditory stimulation EEG data. As time moves downwards in the figure, each block represents two minute bins of data recording in this example, whereas the Example 6 above employed three minute bins of data per task. The protocol begins by collecting EEG data in a resting Eyes Closed state 200, auditory stimulation in the delta band (as a frequency sweep from 0.1 to 4 Hz) follows 203, then a resting Eyes Closed 206 follows, then an auditory stimulation to the ears with frequencies found in the theta band (as a frequency sweep from 4 to 7 Hz) follows 209, then another resting Eyes Closed follows 212, then an auditory stimulation in the alpha band frequency (as a sweep from 8 to 13 Hz) follows 215, then a resting Eyes Closed follows 218, then an auditory stimulation in the beta band (as a frequency sweep from 13 to 30 Hz) follows 221, concluding with a pair of resting Eyes Closed 224 and 227. Since it is known that hearing loss is more pronounced in some specific subpopulations, like the elderly in the case of dementia or AD monitoring and diagnosis, this illustrator auditory stimulation protocol would need to be adapted in the frequencies stimulated. For instance, the stimulation could be adjusted to begin sweeping from 20-100 Hz, then look from 100-400 Hz, then from 400-2000 Hz, and concluding with stimulation in the 2000-5000 Hz frequency range. This 10 task sequence could take 20 minutes to perform.

Alternatively, FIG. 15 illustrates a mixed sensory stimulation and cognitive challenge data acquisition paradigm in which a number of tasks are conducted in a prescribed sequence to collect dynamic EEG data. As time moves downwards in the figure, each block represents two minute bins of data recording; although not all tasks need to be the same length, some could be longer and others shorter. Of particular interest are those data collection paradigms or batteries that comprise three or more tasks for comparison rather than just two states, like eyes open versus closed or traumatic images versus neutral. The protocol starts collecting EEG data in a resting Eyes Closed state 300, followed by auditory stimulation in the form of an auditory sweep in frequencies from 30 to 300 Hz over 2 minutes 303, followed by a resting Eyes Closed 306, followed by 5% CO2 inhalation with Eyes Closed 309, followed by a resting Eyes Closed with normal air inhalation 312, followed by visual stimulation in the form of a flashing checker board sweep from 1 to 20 Hz 315, followed by a first cognitive challenge in the form of delayed word recall or executive function task 318, followed by auditory stimulation in the form of music superimposed with the frequency in the sweep that demonstrated the most response from the frequency sweep from earlier task 303 above 321, followed by a second cognitive challenge in the form of a delayed match to sample task 324, followed by a final resting Eyes Closed 327. This 10 task sequence would take 20 minutes.

Example 5

Baseline Assessment of Normal Healthy Individuals

Imagine a person who visits her doctor to establish a personal brain health biometric signature while she is well and healthy as a baseline. She could take the BCI test battery on a weekly basis or over three separate visits for good test-retest performance. Part of the test battery would include challenges as outlined according to the methods of the present invention using physiological stimuli as well as cognitive tasks, although these will probably exhibit lower test-retest reproducibility. Other stimuli should be usable to calibrate brain function. The leading application is to track changes in an individual from baseline. The potential therapeutic use of such information is that if someone notices their functional brain signature is changing, they can seek additional professional diagnosis. They can also use the information as a type of biofeedback mechanism to practice or perform cognitive therapy. One can engage in mental exercises to bring themselves back to a normal BCI signature. Uses generally include diagnosis, bio-signature, as an aid to guiding treatment, as well as treatment in itself through biofeedback.

Example 6

Alzheimer's Disease or Dementia More Generally

Using both the literature as a guide and an empirical approach, the brain health assessment system and methods of the present invention can be adapted to unique brain health assessments. For instance, in dementia, it has been reported in the literature that as one loses the higher frequency gamma, beta, alpha bands, a concomitant increase in delta and theta power ensues, i.e. the overall power shifts or moves leftward in the PSD graph. Persons with a family history of AD could monitor that movement or change leftward (to lower frequency), as a sensitive means to monitor movement into a state of mild cognitive impairment (MCI). One could arrange to create a PSD band ratio and put in the denominator that which is increasing (theta or delta) and use alpha, gamma, or beta as the numerator. The literature reports that one is losing high frequency power and gaining low frequency power. Thus, one can construct a leveraged and more sensitive metric by taking a ratio. In this way, the ratio amplifies that signature change as neurodegeneration occurs. Thus the invention can replicate the science and provide an early means of detection.

Example 7

Use in Schizophrenia

The possible use of the invention to diagnose Schizophrenia can be found from two important pieces of information. First, Schizophrenics have a problem with sensory information processing, in particular auditory. Thus one could ramp up the frequency, shifting tones every 5 Hz from 60 Hz, 55 Hz, 50 Hz, 45 Hz and look for spike there, or also look at other frequencies. Moreover, in Schizophrenics there are documented input problems. In the paper by Frankie et al, [ref] it was shown that Schizophrenics have a problem with EEG response to working memory load. In sum, Frankie's work showed that if one gives normal subjects several objects to hold in their working memory, the power in the gamma band goes higher and higher during the working memory task. However, in Schizophrenics, it was shown that the gamma power goes up from 1 to 2 objects but it quickly levels off. This could be directly measured in a BCI test battery for use with Schizophrenics.

Example 8

Use in Depression, Bipolar Disorder, and/or Anxiety

In Depression, Bipolar, and Anxiety disorders, there is a unique opportunity to use a $CO_2$ challenge test. It is known that when one gives a subject a lot of $CO_2$, such as 7 or 10% and for longer periods of 15-20 min, doing so can induce a panic or claustrophobic-like attack with anxiety-like feelings. In the past, some practitioners screened patients for Anxiolytics. In disorders like depression, bipolar, or anxiety, it is known that patients are much more sensitive to the $CO_2$ challenge and often develop panic, claustrophobic or anxiety attacks at much shorter times and with lower concentrations of $CO_2$ compared to normal people. It is the opposite situation in the case of depression, where patients demonstrate a higher threshold than normal for $CO_2$ induced behavioral phenomena. Imagine giving a subject 5% $CO_2$ for 5 min and observing both the behavioral and the EEG signals. One should be able under these conditions to observe a robust shift or change in EEG signature before the patient feels anxiety or panic. Low doses of 5% $CO_2$ for 5 min have been observed to exhibit robust EEG signatures. We believe this is a much more robust way to pick up $CO_2$ response. This behavioral exhibited disease performance can translate or enable our more subtle $CO_2$ signature to track and diagnose all types of disease. Thus there is a baseline battery of diseases where one can watch where brain problems appear.

Example 9

Pain Disorders

Another indication where the BCI bio-signature of brain health could be very useful is chronic pain. It is known that chronic pain patients are much more sensitive than normals to the behavior response of the thermal grill, i.e. feeling greater pain to the thermal grill. The idea is simply to assess changes in EEG signature when applying the thermal grill and examine if a heightened response is experienced by chronic pain patients, indicating in those a true sensitization and response to the thermal grill. The alternating pattern of warm (40 deg C.) and cool (20 deg C.) produces a sensation of pain in working brain circuits. There exists robust neurobiology behind the thermal grill. In particular, a normal person reports a low score to the amount of pain felt, whereas someone sensitive to neuropathic pain would report a high score. This test would be useful to assess if someone truly has neuropathic pain. The pain experience is often overlaid in anxiety, and our approach gets around the subjective reporting of pain to a more objective measure of the activation of the pain pathways. The EEG bio-signature based thermal grill challenge would provide an objective measure of the pain pathway. Those truly sensitive would have a higher EEG response to the thermal grill, providing more confidence to the physician in the diagnosis. In addition, after injury to a limb, it is well known that the pain intensifies over time. The bio-signature EEG could track this painful response more objectively and quantitatively.

Example 10

Use as a Remote Device for Home Based Measurements

With proper placement of a cell phone or PDA interface in close proximity to the scalp electrodes, opportunities arise to conduct the brain health assessment remotely, such that an individual could have the proper components present in the home and administered by a physician, taking the patient through the various tests, with the results then transmitted by a cell phone network to a central server for immediate availability to a doctor or nurse. Thus, the systems and methods of the present invention become convenient and practical. Patients would not have to come into a clinical setting to get wired in for an EEG, it could be done weekly at home to obtain much tighter data to average and monitor closely for subtle changes. One can imagine a Facebook-like web page for an individual's EEG data. The subject could upload the data regularly and the doctor could review monthly to monitor the patient's data. Smart cell phones allow bidirectional communication of the test battery and the test results. Thus anywhere a patient has a headset and smart cell phone, she can conduct a BCI like test battery. This test battery could consist of any combination of sensory and cognitive challenges.

Example 11

Use in Head Injury Monitoring and Post Traumatic Stress Disorder

Another disease area where this invention is useful is head injury and Traumatic Brain Injury (TBI). Imagine a high school football player has a mild head injury from a head-on collision on a football field (or from a vehicle accident). Now imagine the player is rushed off the field and given a BCI brain health assessment to determine if they are suitable to go back on the field or should be transported to a hospital for further neuropsychological evaluation. If such individual's brain shows signs of not functioning properly, he would not be permitted to go back into the game and may instead need to go to the hospital. Imagine a similar scenario on a military battlefield or military hospital. After a blast or vehicle accident, one can quickly assess if a solider gets shipped back home or back out into battle. Significant changes from a soldier's normal brain health biometric signature (for example, taken during basic training) will likely result from such head trauma.

The literature has reported several EEG signatures associated with both mild TBI and Post Traumatic Stress Disorder (PTSD). One can envision multi-step sensory and cognitive stimulation brain assessment paradigms tuned to each condition. In the case of mTBI where it is reported that a significant percentage of TBI victims have auditory dysfunction, an auditory stimulation component is indicated, in addition to resting eyes closed and eyes open. Since the scientific literature indicates damage often to the vasculature of the retina in TBI, it is within the systems and methods of the present invention to include a visual stimulation task as well to monitor the EEG response and look for shortcomings or differences due to reduced visual acuity.

In the case of PTSD, a comparison of the EEG of an individual when presented with neutral images (like flowers, the beach, and mountains) versus traumatic images (like photographs of war, soldiers dismembered, vehicles in major crashes) can be tuned to sensitively and specifically identify those with PTSD by monitoring their visually stimulated EEG response.

Example 12

Use of a BCI Test Battery of Sensory and Cognitive Challenges for Relaxation, Meditation, and Reduced Hypertension Through Neurobiofeedback Another disease area where the systems and methods of the present invention could be useful is in assessing hypertension, along with its corollaries, relaxation, and meditation. Imagine a system comprised of an EEG brain cap, in a normal form factor like a baseball cap (illustrated in FIG. 6), and a wireless receiver like those illustrated in FIG. 7. EEG signals from the cap would be transmitted to the client device and data like the NeuroSky "meditation" index or other indicator of relaxation states displayed on the screen. The subject would focus on the real-time adjustment to their signals, thus creating a discrete neuro-biological feedback system. This system could be used to calm the minds of children and adults with Attention Deficit Disorder, as well as those with anxiety or panic disorders.

Example 13

EEG Baseball Cap or Hat with iPhone

Again, consider the same system comprising an EEG brain cap, in a normal form factor like a baseball cap, and a wireless receiver like those indicated in FIG. 7. Imagine that the receiver device is connected to earphones such that the auditory stimulation signals are swept from low (1 Hz) to high (20 kHZ) and response monitored, then refocused between 20 Hz to 1000 Hz or alternatively 20 Hz to 200 Hz. The EEG response in the form of overall PSD power, power in certain bands like alpha or theta, or discrete and specific frequencies could be measured and a response curve for each subject could be created where their PSD or portion of PSD is integrated to form a power measure. Once the response curve for each subject is mapped out, the device could return to the peak response frequency from the scan and superimpose this frequency on top of music signals that the person is choosing to listen to (selected from their favorite MP3 music library selections). Thus in addition to listening to their music, they would get a maximal stimulation or enhancement of the relaxation frequency they were most responsive to during the calibration phase. This could retune between songs from time to time where a frequency sweep is conducted around the previous maximally responsive auditory driving frequency to confirm that the person's response function is still maximally stimulated in a resonance like fashion. If not still in tune, a new superimposed relaxation frequency could be superimposed; if confirmed, this would be the frequency as before. This aspect of the system and method of the present invention represents a real-time frequency test using standard lock-in amplification techniques to increase the gain to the exact frequency of auditory stimulation for maximal auditory response for each individual person. This would be a customized relaxation algorithm tuned to each person's response curve.

Example 14

Use with a Stimulus Battery to Monitor the Brain and Nervous System: Olfactory Response and Food Response The EEG signals from the methods of the present invention could be used to monitor the olfactory response of an individual to various odors, as well as to other consumables such as foods or nutraceuticals. The response to beneficial food components like omega 3-fatty acids, antioxidants, ginko biloba, etc. could be determined. In particular, it is noted that the olfactory bulb of individuals undergoing neurodegeneration, like those folks suffering from Alzheimer's disease, is one of the first areas to lose capacity. Olfactory EEG stimulation tasks as part of a multi-step dynamic data collection paradigm could provide the early indicators necessary to diagnose Mild Cognitive Impairment (MCI) and prodromal Alzheimer's disease from normal controls, mild AD and other non-related dementias.

Example 15

The Effect of GABA_A Receptor Agonist Clonazepam on EEG

The GABA_A receptor agonist Clonazepam (under trade name Klonopin from Roche), a member of the benzodiazepine family, has been reported in the literature to increase the relative power in spectral beta relative to other sub bands. To assess this with the systems and methods of the present invention, an Eyes Closed (EC)/Eyes Open (EO) resting state assessment was conducted on a 48 year old male subject. Four tests of 3-minutes each in an alternating pattern (EC/EO/EC/EO) were taken using a NeuroSky MindSet Pro headset (serial number NS-MS1-00273), sampling at 128 Sam/sec with 12 bit precision. Traces were recorded to a SONY Viao (VGN-FZ1 OE) laptop PC using Neuroview 4.2.2 software in the early evening. After the initial sequence, one pill of 0.5 mg dose Klonopin was taken orally with water. The 48 year male volunteer rested quietly with the lights off 80 minutes postdose, data was again collected using the exact same sequence of four 3-minute resting state assessment tests (EC/EO/EC/EO), recorded to the laptop PC. The data files and testing record files were immediately transferred following the second series of tests.

An hour later, the EEG data was loaded into MATLAB using custom-written proprietary software for spectral FFT analysis. Time averaged PSD plots were generated from 0 to 30 Hz with log power on the y-axis (in MATLAB) and the results archived in both a PowerPoint file and comma separated value (CSV) files for further analysis in statistics (JMP by SAS) and graphical software (KaleidaGraph by Synergy Software) packages. FIG. 29 shows in the upper panel the resting Eyes Open average relative PSD. Notice the relatively well behaved 1/f fall off in the PSD as a function of the frequency. The beta region 670 is clearly falling off in the semi-log plot. In comparison, 80 minutes after 0.5 mg Klonopin, one observes an elevated beta 680 and even more pronounced alpha rhythm 690 emerging from the Clonazepam. Individual relative and absolute power in each of the spectral delta, theta, alpha, and beta bands was calculated and a pair-wise t-Test of each power was compared pre-pill versus post-pill. There was no statistical difference in the time averaged relative power in the delta, theta and alpha bands, with p-values ranging from 0.51 to 0.99, all non-significant. In contrast, the time averaged relative beta band power was statistically significantly elevated ($p=0.019$, $N=4$ traces in each comparison) showing meaningful elevations in relative beta power upon Clonazepam administration. Moreover, the absolute power showed statistically meaningful differences 80 minutes post-dose relative to pre-dose levels also ($p=0.021$, $N=4$ traces of three minute duration per state).

Example 16

The Effect of Histamine H1 Receptor Antagonist Benadryl on EEG

The Histamine H1 receptor antagonist "Benadryl" (Diphenhydramine HCl) is known to cause drowsiness. 25 mg of Benadryl equivalent (CVS Generic Brand—"Compare to Benadryl Allergy"), was assessed with the methods and systems of the present invention in a similar study to the Clonazepam study above. The same 48 year old male subject conducted six tests of 2-minutes each in an alternating pattern (EC/EO/EC/EO/EC/EO) taken using a NeuroSky MindSet Pro headset (serial number NS-MS1-00273), sampling at 128

Sam/sec with 12 bit precision. Traces were recorded to the same SONY Viao (VGN-FZ1 OE) laptop PC using Neuroview 4.2.2 software. At the end of the first sequence, one pill of Diphenhydramine HCl 25 mg was taken orally with water. The subject rested quietly with the lights off 65 minutes post-dose, EEG data was again collected using the exact same sequence of six 2-minute resting state assessment tests (EC/EO/EC/EO/EC/EO) and recorded to the laptop PC. The data files and testing record file were transferred to the signal analyst.

The EEG data was loaded into MATLAB using custom-written proprietary software for spectral FFT analysis. Time averaged PSD plots were generated from 0 to 30 Hz with log power on the y-axis (in MATLAB) and the results archived in both a PowerPoint file (see FIG. 30) and comma separated value (CSV) files for further analysis in statistical (JMP by SAS) and graphical software packages (KaleidaGraph by Synergy Software). Individual relative and absolute power in each of the spectral delta, theta, alpha, and beta bands was calculated. A pair-wise t-Test of each power was compared pre-pill versus post-pill. Interestingly, the absolute beta sub-band power (FIG. 30) was statistically significantly elevated in the post Benadryl blocks of data compared to the pre-pill (p=0.02).

These examples show the ability of the single lead Mind-Scope™ systems and methods to detect EEG traces at electrode position Fp1 that are equivalent to those of much more expensive and cumbersome 10-20 International standard EEG rigs in an Eyes Closed/Eyes Open protocol. The systems and methods of the present invention can be leveraged to further refine the signatures and classifiers of compound effects when assessed under sensory and cognitive challenges. In subsequent studies, the EEG data can serve as objective evidence for investigational compound target engagement, serving to assist in dosing ranging studies, and ultimately be useful in personalized medicine studies where an individual's pharmacokinetics are correlated with their personal pharmacodynamic endpoints, including the metrics and classifiers derived from the systems and methods of the present invention. The data can also be expressed as graphic biometric "signatures" in the form of spider plots or other multivariate representations.

Example 17

Using the System to Monitor States of Attentiveness

An additional use of the systems and methods of the present invention is to control the output of certain EEG signals by a user of the system. This control was demonstrated by a 48 year old male subject, using the algorithms present in NeuroSky's Neuroview™ software, interfacing with Neuro-Sky's MindSet Pro™ headset (serial number 25 NS-MS1-00273), sampling at 128 Sam/sec with 12 bit precision. Traces were recorded to a SONY Viao (VGN-FZ1 OE) laptop PC using Neuroview 4.2.2 software. Three tests of approximately 1-minute each were conducted in an eyes open (EO) resting state. The NeuroSky software comes with an "Attention Meter", which is graphically displayed as a tachometer with an analog needle that moves from the 8 o'clock position on the clock face to the 5 o'clock position in increments of 1 percent, from a possible low of 0 percent to a high of 100 percent, with a simultaneous numerical score displayed as well.

The subject was asked to maximize the Attention meter at 100 percent and, if possible, to keep it there for 10 seconds. The collected data was analyzed for PSD properties as described earlier and can be seen in FIG. 28.

The high attention task 640 is significantly elevated in overall power during the Attention related task. In contrast, when the subject attempted to pin the meter to zero, he was only able to get it below 20 for at least 10 seconds, as shown in trace 650. The output from the low ATTENTION meter trace is also visible in FIG. 28. One can clearly see the difference in overall power in an attentive state compare to an inattentive state of mind. This demonstrates the systems and methods of the present invention to characterize states of attentiveness for the purpose to monitor the brain and nervous system of a subject.

Example 18

To Monitor and Characterize States of Alertness Ranging from Asleep to Awake

An additional use of the systems and methods of the present invention is monitor sleep states. This was demonstrated by a 48 year old male subject, interfacing with Neu-roSky's MindSet Pro headset (serial number NS-MS1-00273), sampling at 128 Sam/sec with 12 bit precision. Traces were recorded on a SONY Viao (VGN-FZ1 OE) laptop PC using Neuroview 4.2.2 software. At the same time that the data was being recorded, the session was being filmed using a Sony HDV Handycam digital video tape recorder mounted on a tripod.

The internal clocks of the Sony video camera and the Sony VAIO laptop synchronized with an offset differential of 2 seconds, with the laptop being 2 seconds ahead. The subject was tape recorded while going through the following resting states during an afternoon nap: (1) Eyes Open awake; (2) Eyes Closed awake; and (3) Eyes Closed asleep (as evidenced by noises and twitches). The total recording time of the study was approximately 12.5 minutes. The data files and testing record file were transferred to the signal analyst.

The following day the EEG data was loaded into MATLAB using custom-written proprietary software for spectral FFT analysis. Time averaged relative power spectra were generated from 0 to 30 Hz with log power on the y-axis for 60 sec states of the data reflective of each of the observed awake states listed above. The results can be seen in the PSD plots of FIG. 31. 730 shows the PSD for an Eyes Open awake state, in comparison to an Eyes Closed awake state 740, finally compared to an Eyes Closed asleep state with even less overall power.

Example 19

Photic Stimulation at Driving Frequency F Leads to Brainwave Entrainment as a Monitoring Tool Using the methods and system of the present invention, we sought to demonstrate the ability to entrain the brain using photic stimulation. Using a MindPlace Procyon AVS unit with LED goggles, we programmed the goggles to flash the LEOs at full intensity with Red=255, Green=255, Blue=255 amplitude for maximum light output via the USB port of a Compaq Eva N620c laptop PC and the downloadable Procyon AVS software from the MindPiace.com website. A 45 year old male volunteer sat in a quiet room with the lights off. Two minute traces were collected in each of the following conditions at high photic stimulation intensity: EC no photic stimulation, 10 Hz, 12 Hz, 14 Hz, 16 Hz, 18 Hz, and 20 Hz photic stimulation for 2 minutes. fEEG data was collected at 128 Sam/sec with a MindSet Pro headset using Neuroview 4.2.2 software on a Dell Inspiron laptop running Windows?. Both eyes were stimulated simultaneously in phase in order to assess the largest effect size possible.

Data was stored on the Dell laptop and then analyzed for spectral content after data were loaded into MATLAB running proprietary BCILAB software. The software performed standard Hanning windowing and Fast Fourier Transform of the data. Power spectral density plots were generated in log scale from 0 to 30 Hz.

One can see the results of the study in FIG. 25 for 10 Hz and FIG. 26 for 12 Hz where there is a prominent peak in the PSD at the stimulation frequency F 540 and 560 as well as the first harmonic (2° F.) 550 and 570, evidence of some nonlinearity in the system. The EC no photic stimulation state is plotted below for comparison purposes.

The ability to measure a response to the photic stimulation enables one to include this task into the battery of tasks to be conducted for brain state and functional analysis. This could include but is not limited to use in detecting, identifying, or monitoring diseased brain states like Alzheimer's disease or Schizophrenia, detecting, identifying, or monitoring injured brain states such as mild traumatic brain injury or stroke, or detecting, identifying, or monitoring brains under the influence of both legal and illegal drugs in an emergency room context where a patient presents with issues but is unconscious or uncooperative or in a clinical trial process of drug discovery in the pharmaceutical industry.

Example 20

Auditory Stimulation at Driving Frequency F Leads to Brainwave Entrainment as a Monitoring Tool Using the methods and system of the present invention, we sought to demonstrate the ability to entrain the brain using auditory stimulation. Using a Neuroprogrammer 3 (NP3) software from Transparent Corp, we programmed sessions where we could output pure isochronic tones, monaural beats and binaural beats through the soundcard of a Dell Vostro 1520 laptop PC. A 45 year old male volunteer sat in a quiet room with the lights off 90 second traces were collected in each of the following conditions at 128 Sam/sec with 12-bit dynamic range. Data was collected in both an Eyes Open and Eyes Closed state for all conditions tested on a Dell Inspiron laptop PC using the standard Bluetooth dongle and Neuroview 4.2.2 software.

Isochronic tones were output from the PC soundcard with beat frequency ranging from 10 to 20 Hz in 2.5 Hz steps, which corresponded to optimized pitch frequencies from the program of from 147 Hz to 200 Hz. Parameters of the isochronic tones included square waves, 90 degree phase, sine pitch, with 1-20 Hz corresponding to 100-200 Hz pitch. The amplitude was put on full both at the Windows7 soundcard driver as well as within the NP3 program. The sound was relayed through the Bluetooth interface to the audio speakers built into the MindSet Pro headsets.

Monaural beats were output from the PC soundcard with beat frequency ranging from 10 to 20 Hz in 2.5 Hz steps, which corresponded to optimized pitch frequencies from the program of from 147 Hz to 200 Hz central frequency with beat frequency symmetric. For example, a 20 Hz beat corresponded to a central pitch of 200 Hz, with tone 1 and tone 2 corresponding to 190 Hz and 210 Hz respectively. The amplitude was put on full both at the Windows7 soundcard driver as well as within the NP3 program. The sound was relayed through the Bluetooth interface to the audio speakers built into the MindSet Pro headsets.

Binaural beats were output from the PC soundcard with beat frequency ranging from 10 to 20 Hz, which corresponded to optimized pitch frequencies from the program of from 10 Hz to 200 Hz. The amplitude was put on full both at the Windows7 soundcard driver as well as within the NP3 program. The sound was relayed through the Bluetooth interface to the audio speakers built into the MindSet Pro headsets.

Data was stored on the Dell Inspiron laptop and then analyzed for spectral content after data were loaded into MATLAB running proprietary BCILAB software. The software performed standard Hanning windowing and Fast Fourier Transform of the data. Power spectral density plots were generated in log scale from 0 to 30 Hz. Both 10 second sliding window absolute power PSD and time averaged relative PSD were produced.

One can see the results of a study in FIG. 33 for 15 Hz Isochronic tones in an Eyes Closed state. The effect in the PSD is more subtle than the photic stimulation.

Example 21

Cog Scope™ Non-Invasive Multi-Modal Assessment

Using the methods and system of the present invention, we sought to demonstrate the ability to simultaneously record EEG data while taking a computerized cognition test. In particular, we loaded the CogState Research battery from CogState Ltd. onto a Dell Vostro 1520 laptop PC (like FIG. 17 351). We configured the test to only administer the "Identification" task as a proof of concept Attention task (FIG. 16 305) demonstration that we could generate meaningful data from both the cognitive test and the simultaneous EEG signals (FIG. 16, where Cog 306 is, without limitation, the reaction time of the individual trials). The Identification task asks the test subject to press the D key if a black card is flipped and the K key if a red card is flipped from a deck of playing cards on a solid background, or to click the left mouse if a black card is flipped or the right mouse button if a red card is flipped, depending on the color of the next playing card which is flipped over from a deck on the computer screen. Cards are turned every few seconds and the response of the individual monitored by the program for reaction time to the trial and accuracy, among other things.

In addition, while the test was taking place, we simultaneously recorded EEG from a MindSet Pro to a Dell Inspiron laptop PC via standard conditions listed in examples above. The Identification task took approximately 105 seconds to complete approximately 40 trials. The CogState Analysis Guide recommends that one evaluate the log of the reaction time for those correct trials of an individual. As one ages or shows dementia, the ability to stay attentive decreases, and therefore the average log 10 10 reaction time increases.

The schematic of the system can be seen in FIG. 17. The two PCs were synchronized to within a second before the study began at time.nist.gov 353. EEG data was stored on the Dell Inspiron laptop 355 and then analyzed for spectral content after data were loaded into MATLAB running proprietary BCILAB software 357. The software performed standard Hanning windowing and Fast Fourier Transform of the data. Power spectral density plots were generated in log scale from 0 to 30 Hz. FIG. 18 is the time averaged relative PSD during the Cog State™ Identification task.

The CogState data was analyzed according their research manual. Results were uploaded to the DataPoint™ website and raw data observed via the web portal. Raw data were copied to MS Excel with full detail as shown in FIG. 19 from the study, including the elapsed time 365, reaction time 366, key pressed 367, and card flipped 368. EEG data could be added to the data table for construction of a summary data table with the EEG biometric data from the spectral analysis and the reaction time and accuracy data, as shown in FIG. 20.

The ability to simultaneously measure cognition task data, both computerized and otherwise, and EEG data represents a large advance. The tests take no more time than a straight cognition test but now provide a whole new realm of biometric variables to construct classifiers from in combination with the cognition data. This multi-modal classifier is an important aspect of the present invention. This has application in dementia testing with the CogState battery and concussion testing with the CogSport battery.

Example 22

PASAT+fEEG Assessment of Cognition

Using the methods and system of the present invention, we sought to demonstrate the ability to simultaneously record functional EEG (fEEG) data while taking a second computerized cognition test. In particular, we purchased the Paced Auditory Serial Addition Test (PASAT) from the University of Victoria, Dept. of Neuropsychology. The schematic of the PasatScope™ system can be seen in FIG. 21. We loaded and activated the PASAT software onto a Dell Vostro 1520 laptop PC (FIG. 21 391). We configured the PASAT test as a second proof of concept cognitive task demonstration that we could generate simultaneous data from both a cognitive test and EEG signals (FIG. 16, where Cog 306 is, without limitation, the reaction time of the individual trials). The PASAT task asks the test subject to listen carefully to a series of auditory numbers spoken a fixed interval, say every three seconds. The subject is to listen to each new number and indicate the sum of the new number to the preceding number. Thus if the test computer voice speaks "1", "3", then the test subject should say "4" before the next number is spoken by the test computer voice. If the computer voice says "4" next, the test subject should add the "4" to the previous "3" and say "7". A test administrator sits next to the test subjects and records their responses for later scoring off paper. We chose to automate the process and utilized an Olympus VN-960PC Digital Voice Recorder next to the laptop speaker to record both the computer voice saying the numbers and the test subject's responses. In this system, the Monitor-1 390 is an audio monitor in the form of the digital voice recorder. The data from the voice recorder was recorded in HQ at 22,050 Sam/sec and transferred to PC-1 391 after the test task was completed as .wav file. Audacity software (www.audacity.com) was downloaded for free and the .wav opened as an element of the analysis package 392. Using the cursor, one could quantitatively measure the reaction time between each new number spoken by the computer voice and the test subject's response. In this way, we have refined the scoring nature of the PASAT by extracting reaction time information as well accuracy information. This will enable analysis similar in spirit to the CogScope example just above.

In addition, while the test was taking place, we simultaneously recorded EEG from a MindSet Pro to a Dell Inspiron laptop PC-2 395 via standard conditions listed in examples above. At speed 2.4, the PASAT task took approximately 105 seconds to complete the 60 trials. The PASAT software has four possible speeds, indicated by 2.4, 2.0, 1.6 and 1.2 from slowest to fastest. The PASAT Scoring portion of the program takes the raw score correct out of a possible 60 and based on age range, calculates the z-score and percentile based on published literature validating the instrument in a normative sense. As one ages or shows dementia, the ability to correctly add the scores, remember the previous and speak the response is impaired. It is very difficult to do well as the speed moves to 1.6 let alone 1.2. Another person sat by the test subject and recorded to paper with pencil both the computer voice series of test numbers as well as the test subject's responses. This enabled paper determination of the correct number of trials, as shown in FIG. 23.

The schematic of the PasatScope system can be seen in FIG. 21. The two PCs PC-1 391 and PC-2 395 were synchronized to within a second before the study began at time.nist-.gov 393. EEG data was stored on the Dell Inspiron laptop 395 and then analyzed for spectral content after data were loaded into MATLAB running proprietary BCILAB software 397. The software performed standard Hanning windowing and Fast Fourier Transform of the data. Power spectral density plots were generated in log scale 20 from 0 to 30 Hz. FIG. 22 is the time averaged relative PSD during the PASAT 405 versus a resting Eyes Open baseline 410. Notice again the large amount of power during the cognitive task in comparison to a resting Eyes Open baseline.

The PASAT data was analyzed according their scoring software functionality (FIG. 23). First the age range 420 was selected. Then the individual raw scores out of 60 trials for each speed of the 2.4 425, 2.0 430 and 1.6 435 were input. The PASAT software calculated the yellow boxes showing the Z score 440 and percentile 445 from the published normative data.

Rather than stop the analysis with the PASAT scoring software, as is presently done in the field, we analyzed the voice recording in Audacity 1.2.6, free Digital Audio Editor software (audacity.sourceforge.net1). The digital recorded audio .wav file was loaded into Audacity (FIG. 24 450). By zooming in, one could isolate 12 seconds of recording and see bursts of intensity that corresponded to either the computer test administrator voice 451 or the test subject's voice 452 in the audio file. There were periods of silence 453 between the two voices. One could deduce that the number "2" was spoken by the computer administrator voice at 455, the number "7" at 465, the 5 number "5" at 475, and the number "1" at 485. The test subject 452 responded "9" at 470, "12" at 480, and "6" at 490. By measuring the periods of silence between the last new number and the test subject's response 500, 510, 520, we calculated the response time for each trial T1 500, T2 510, T3 520. Using voice recognition algorithms, some of which are now built into Windows Vista and Windows?, one could automate the scoring as well, although we haven't done this yet. Nonetheless, we did measure the reaction times between trials of new numbers and test subject's responses. Using the cursor bar, regions of silence between the last number and the subject's response were measured and recorded in the table 530.

The ability to simultaneously measure cognition task data, both computerized and otherwise, and EEG data represents a large advance for not only the PASAT, but all other computerized cognition tests. Since the simultaneous cognition+ fEEG tests take no more time than a straight cognition test, but now provide a whole new realm of objective independent biometric variables to construct classifiers from in combination with the cognition data. This multi-modal classifier method is an important aspect of the present invention.

Example 23

Probing Pain Circuit Analysis with an Ice Cube in Lieu of a Thermal Grill

Using the methods and system of the present invention, we sought to demonstrate the ability to detect EEG differences while a volunteer was in a pain state much like the alternating temperature conditions of the thermal grill. In this instance, a 45 year old male volunteer held either a room temperature mini computer mouse as a control or a wet ice cube in his hand, both left and right at different times, for 60 seconds. In each instance, the room temperature computer mouse was held first as a control, then the wet ice cube. Each condition, mini-mouse and ice cube, right hand and left hand, Eyes Open and Eyes Closed was conducted for a total of eight blocks of data.

While the test was taking place, we simultaneously recorded EEG from a MindSet Pro to a Dell Inspiron laptop PC via standard conditions listed in examples above. The computer was controlled by someone else in Manhattan via a web interface GoToMeeting. The EEG data was analyzed for spectral content after data were loaded into MATLAB running proprietary BCILAB software. The software performed standard Hanning windowing and Fast Fourier Transform of the data. Power spectral density plots were generated in log scale from 0 to 30 Hz. FIG. 27 A and FIG. 278 are a pair of time averaged relative PSD during the ice cube holding task with Eyes Closed in the left hand. One can observe the prominent alpha rhythm peak 580 in the room temperature mini mouse task with is significantly diminished 590 when holding an ice cube for 60 seconds. Additional features appear to be quite different including low theta regional power 600 appearing elevated while holding an ice cube. This demonstrates the alpha rhythm monitor approach to probing circuits. It can be expanded to include many other circuit flows to monitor the brain and nervous system.

Example 24

Use of Tongue Restraint and Visual Objects to Minimize Dipolar Movement, Especially the Tip of the Tongue and Eye Movement Imagine an aspect of the systems and methods of the present invention to include a bite-plate like device which immobilizes the tongue to prevent tongue movement which could create artifacts for the recorded EEG signals. A tongue immobilizer would enable reduced artifacts and cleaner EEG data. Similarly, it is important to provide instructions on where the participant should be looking visually at all times during the battery or data collection paradigm so that eye movement is reduced to a minimum. Visual objects and targets are to be provided on the display screen at all times that the participant has their eyes open so that their eyes are not wandering around creating additional eye movement artifacts in the recorded EEG signals. It will be difficult to reduce eye blink completely, but by providing visual targets for the subject's eyes to fix and focus on is a method of the present invention to improve the signal quality recorded.

While the above description contains many specifics, these specifics should not be construed as limitations on the scope of the invention, but merely as exemplifications of the disclosed embodiments. Those skilled in the art will envision many other possible variations that are within the scope of the invention.

What is claimed:

1. A method to monitor a brain and nervous system of a subject during cognitive challenge tasks, comprising:
    a recording device recording an audio voice of a subject and an audio voice of a test administrator conducting a cognitive challenge task of the subject to create audio voice signal data;
    transferring the audio voice signal data to a microprocessor;
    digitally processing the audio voice signal data, using the microprocessor, to quantitatively measure features of the audio voice response of the brain and nervous system of the subject to the cognitive challenge task including reaction times determined from periods of silence between sequential audio voice prompts from the test administrator and corresponding audio voice responses of the subject in response to each respective audio voice prompt from the test administrator during the cognitive challenge task; and
    applying a medical therapy for the subject based on changes in the reaction times between administrations of the cognitive challenge task.

2. The method of claim 1, wherein the cognitive challenge task is the Paced Auditory Serial Addition Test (PASAT) task.

3. The method of claim 1, wherein the audio voice signal data recorded in the recording step is recorded in a hand held digital voice recorder or via a sound card with built in analog to digital converters.

4. The method of claim 1, wherein the digital signal processing step further measures the accuracy of a response using automated audio voice recognition techniques.

5. The method of claim 1, wherein using the reaction times to monitor the brain and nervous system of the subject comprises using the reaction times in at least one of the surveillance of normal health and aging of the subject, the early detection and monitoring of brain dysfunction of the subject, monitoring of brain injury and recovery of the subject, monitoring disease onset in the subject's brain, monitoring disease progression and response to therapy for the subject, measuring the discovery and optimization of treatment and drug therapies of the subject, and the monitoring of illegal substances and their presence or influence on the subject while driving, playing sports, or engaged in other regulated behaviors.

6. A system to monitor a brain and nervous system of a subject during cognition challenge tasks, comprising:
    means for conducting a cognitive challenge task of the brain and nervous system of a subject;
    means for recording an audio voice response of a subject and an audio voice of a test administrator conducting the cognitive challenge task of the subject to create audio voice signal data;
    processing means for processing the audio voice signal data to quantitatively measure features of the audio voice response of the brain and nervous system of the subject to the cognitive challenge task including reaction times determined from periods of silence between sequential audio voice prompts from the test administrator and corresponding audio voice responses of the subject in response to each respective audio voice prompt from the test administrator during the cognitive challenge task; and
    means for applying a medical therapy for the subject based on changes in the reaction times between administrations of the cognitive challenge task.

7. The system of claim 6, wherein the means for recording the audio voice response comprises a digital voice recorder.

8. The system of claim 6, wherein the monitoring means further determines accuracy of a brain and nervous system of a subject in response to the cognitive challenge tasks using automated audio voice recognition techniques.

9. The system of claim 6, wherein the cognitive challenge task is the Paced Auditory Serial Addition Test (PASAT) task.

10. The system of claim 6, wherein the cognitive challenge task is a computerized cognition test.

11. The system of claim 6, wherein the monitoring means uses the reaction times to monitor the brain and nervous system of the subject during at least one of the surveillance of normal health and aging of the subject, the early detection and monitoring of brain dysfunction of the subject, monitoring of brain injury and recovery of the subject, monitoring disease onset in the subject's brain, monitoring disease progression and response to therapy for the subject, measuring the discovery and optimization of treatment and drug therapies of the subject, and the monitoring of illegal substances and their presence or influence on the subject while driving, playing sports, or engaged in other regulated behaviors.

\* \* \* \* \*